US008795685B2

(12) United States Patent
Renard et al.

(10) Patent No.: US 8,795,685 B2
(45) Date of Patent: Aug. 5, 2014

(54) MUTATED HIV NEF FOR MODULATING IMMUNITY

(75) Inventors: Martial Renard, Paris (FR); Marianne Mangeney, Paris (FR); Thierry Heidmann, Paris (FR)

(73) Assignees: Institut Gustave Roussy, Villejuif (FR); Centre National de la Recherche Scientifique, Paris (FR); Universite Paris Sud XI, Orsay (FR)

( * ) Notice: Subject to any disclaimer, the term of this patent is extended or adjusted under 35 U.S.C. 154(b) by 1389 days.

(21) Appl. No.: 11/660,449

(22) PCT Filed: Aug. 17, 2005

(86) PCT No.: PCT/EP2005/008907
§ 371 (c)(1),
(2), (4) Date: Oct. 1, 2007

(87) PCT Pub. No.: WO2006/018289
PCT Pub. Date: Feb. 23, 2006

(65) Prior Publication Data
US 2008/0220008 A1    Sep. 11, 2008

(30) Foreign Application Priority Data
Aug. 17, 2004  (EP) .................................. 04292056

(51) Int. Cl.
*A61K 39/21*    (2006.01)
*C07K 14/16*    (2006.01)
*A61K 38/16*    (2006.01)

(52) U.S. Cl.
CPC .............. *A61K 39/21* (2013.01); *A61K 38/162* (2013.01); *A61K 2300/00* (2013.01); *C07K 14/161* (2013.01); *C07K 14/162* (2013.01); *C07K 14/163* (2013.01)
USPC .......................... 424/208.1; 530/350; 530/359

(58) Field of Classification Search
None
See application file for complete search history.

(56) References Cited

U.S. PATENT DOCUMENTS

| | | | | | |
|---|---|---|---|---|---|
| 5,079,342 | A | * | 1/1992 | Alizon et al. ................. | 530/324 |
| 5,221,610 | A | * | 6/1993 | Montagnier et al. ........... | 435/7.1 |
| 5,962,635 | A | | 10/1999 | Azad et al. | |
| 5,968,514 | A | | 10/1999 | Johnson et al. | |
| 2004/0037825 | A1 | | 2/2004 | Bond et al. | |

FOREIGN PATENT DOCUMENTS

| | | | |
|---|---|---|---|
| WO | WO 88/05440 | * | 7/1988 |
| WO | WO 90/12021 | * | 10/1990 |
| WO | 98/26075 | | 6/1998 |
| WO | 02/069691 | | 9/2002 |

OTHER PUBLICATIONS

Woodberry et al., Journal of Virology, 1999, 73(7):5320-5325.*
Oram et al., AIDS Res. Hum. Retroviruses, 1990, 6:1073-1078 with alignment.*
Franchini et al. alignment (1989).*
Hel et al., Vaccine, 2002, 20:3171-3186.*
Guo et al., Nature, 1991, 349: 745-746.*
Padua et al., Journal of General Virology, 2003, 84:1287-1299.*
Kang et al., Journal of Acquired Immune Deficiency Syndromes & Human Retrovirology, 1998, 17(1):58-68.*
"Broadly increased sensitivity to cytotoxic T lymphocytes resulting from Nef epitope escape mutations," Journal of Immunology, Ayub Ali et al., vol. 171, No. 8, Oct. 15, 2003, pp. 3999-4005, XP00231186.
"Evaluation of genetic diversity of human immunodeficiency virus type 1 nef gene associated with vertical transmission," Tobias Hahn et al., Journal of Biomedical Science, vol. 10, No. 4, pp. 436-450, XP002348903, (2003).
"Natural variation of the nef gene in human immunodeficiency virus type 2 infections in Portugal," Elizabeth Padua et al., Journal of General Virology, vol. 84, No. 5, May 2003, pp. 1287-1299, XP002348904.
"Conversation of the central proline-rich (PxxP) motifs of human immunodeficiency virus type 1 Nef protein during the disease progression in two hemophiliac patients," AK Asamitsu et al., FEBS Letters, vol. 459, No. 3, Oct. 15, 1999, pp. 399-404, XP004375868.
"Prolonged survival of rat liver allograft with adenoviral gene transfection of human immunodeficiency virus type 1 nef," Masayuki Fujino et al., Liver Transplantation, Official Publication of The American Association for the Study of Liver Diseases . . . , vol. 9, No. 8, Aug. 2003, pp. 805-813, XP009041657.
Mutation of a conserved residue (D123) required for oligomerization of human immunodeficiency virus type 1 Nef protein abolishes interaction with human thioesterase and results in impairment of Nef biological functions, Lang Xia Liu et al., Journal of Virology, vol. 74, No. 11, Jun. 2000, pp. 5310-5319, XP002348905.
"The human thioesterase II protein binds to a site on HIV-1 Nef critical for CD3 down-regulation," George B. Cohen et al., Journal of Biological Chemistry, vol. 275, No. 30, Jul. 28, 2000, pp. 23097-23105, XP002348906.
"In vivo mutational analysis of the N-terminal region of HIV-1 Nef reveals critical motifs for the development of an AIDS-like disease in CD4C/HIV transgenic mice," Zaher Hanna et al., Virology, vol. 327, No. 2, Oct. 1, 2004, pp. 273-286, XP002311184.
"Antibody-dependent cellular cytotoxicity via humoral immune epitope of Nef protein expressed on cell surface," Takeshi Yamada et al., Journal of Immunology, Feb. 15, 2004, vol. 172, No. 4, pp. 2401-2406, XP002311185.
"Phylogenetic analysis of the Nef gene reveals a distinctive monophyletic Clade in Korean HIV-1 cases," Mi Ran Kang et al., Journal of Acquired Immune Deficiency Syndromes and Human Retrovirology, vol. 17, No. 1, pp. 58-68, XP009041552, (1998).
HLA-dependent variations in human immunodeficiency virus Nef protein alter peptide/HLA binding, Isabelle Couillin et al., European Journal of Immunology, vol. 25, No. 3, 1995, pp. 728-732, XP009041575.

(Continued)

*Primary Examiner* — Nicole Kinsey White
(74) *Attorney, Agent, or Firm* — Young & Thompson

(57) ABSTRACT

Described is the use of a mutation of at least one amino acid in the immunosuppressive domain of a HIV or SIV accessory protein, for modulating the immunosuppressive property of the protein.

7 Claims, 8 Drawing Sheets

(56) References Cited

OTHER PUBLICATIONS

"Impaired cytotoxic T lymphocytes recognition due to genetic variations in the main immunogenic region of the human immunodeficiency virus 1 NEF protein," Isabelle Couillin et al., Journal of Experimental Medicine, vol. 180, No. 3, 1994, pp. 1129-1134, XP000572554.

"Analysis of the SH3-Binding Region of HIV-1 Nef: Partial Functional Defects Introduced by Mutations in the Polyproline Helix and the Hydrophobic Pocket," H. M. Craig et al., Virology, vol. 262, No. 1, Sep. 15, 1999, pp. 55-63, XP0044389819.

"Antiangiogenic effects of a novel HIV-1 nef cytotoxic peptide on the growth of primary and metastatic colorectal cancer," HL Bumpers, Proceedings of The AACR, vol. 45, Mar. 2004, XP002311241.

* cited by examiner

```
NEF_HIV1U4    MGGKWSKKSRVEWPEVRKRMRETP---AAAK----------GVGAVSQ-----DLDKYG-
NEF_HIV1EL    MGGKWSKSSIVGWPAIRERIRRTN---PAAD----------GVGAVSR-----DLEKHG-
NEF_HIV1ZH    MGNKWSK----GWPAVRERIRQTPPAPPAAE----------GVGAASQ-----DLAKHG-
NEF_HIV112    MGGKWSKSSVVGWPAVRERMRRAE---PAAD----------GVGAASR-----DLEKHG-
NEF_HIV1B1    MGGKWSKSSVVGWPTVRERMRRAE---PAAD----------GVGAASR-----DLEKHG-
NEF_HIV1SC    MGGKWSKRSVVGWPTVRERMRKTE---PAAD----------GVGAASR-----DLEKHG-
NEF_HIV1JR    MGGKWSKHSVPGWSTVRERMRRAE---PATDRVRQTEPAAVGVGAVSR-----DLEKHG-
NEF_HIV1MA    MGGKWSKSSIVGWPKIRERIRRTP---PTET----------GVGAVSQDAVSQDLDKCG-
NEF_SIVCZ     MGTKWSKSSLVGWPEVRRRIREAP---TAAE----------GVGEVSK-----DLERHG-
NEF_SIVS4     MGGAISKKQYKRGGNLRERLLQARGETYGRLWEGLEEGYSQSLGASGKGLSSLSCEPQKY
NEF_SIVM1     MGGAISKKRSKPPRDLRQRLLRARGENYGRLFKGVEDGSSQSLGGLDKGLSSLSCEGQKY
NEF_HIV2SB    MGASGSKKRSRPSRGLQERLLRARGGACGGLWDESEGGYSQFHEGSGREQKLPSCEGQRY
NEF_HIV2RO    MGASGSKKHSRPPRGLQERLLRARAGACGGYWNESGGEYSRFQEGSDREQKSPSCEGRQY
NEF_HIV2ST    MGASGSKKRSEPSRGLRERLLQTPGEASGGHWDKLGGEYLQSQEGSGRGQKSPSCEGRRY
NEF_HIV2CA    MGASGSKKRSRPLQGLQERLLRARAGTCGECYNALEGESLRSQEGSDREQNSLSCEGQRY
NEF_HIV2BE    MGASGSKKLSKHSRGLRERLLRARGDGYGKQRDASGGEYSQFQEESGREQNSPSCEGQQY
NEF_HIV2D2    MGSAGSKKRSERQQGLREKLLRVPERPYGRLSGERREQSSRSPGESDKDLNSPSCEGQ--
NEF_SIVAI     MGSSNSKRQQQGLLKLWRGLRGKPGADWVLLSDPLIGQSSTVQEECGKALKKSWGK----
NEF_SIVA1     MGLGSSKPQHKKQLTIWRALHATRHTRYGLLADPLIGQSSTLQEECDKGLRKSLIRKRN-
NEF_SIVGB     MGSSQSKKRSEAWVRYSSALRQLVGG-------PVTPDGYKQIESSQGAEKQSLLRGRAY
                **   **                  :

NEF_HIV1U4    ------------AVTSSNTSSTNASCAWLEAQEEGD-VGFPVRPQVPLRPMTYKAAFDLS
NEF_HIV1EL    ------------AITSSNTASTNADCAWLEAQEESDEVGFPVRPQVPLRPMTYKEALDLS
NEF_HIV1ZH    ------------AISSSNTATNNPDCAWLEAQEESEEVGFPVRPQVPLRPMTFKGAFDLS
NEF_HIV112    ------------AITSSNTAANNAACAWLEAQEEEK-VGFPVTPQVPLRPMTYKAAVDLS
NEF_HIV1B1    ------------AITSSNTAATNAACAWLEAQEEEE-VGFPVTPQVPLRPMTYKAAVDLS
NEF_HIV1SC    ------------AITSSNTPANNADCAWLEAQEEEE-VGFPVRPQVPLRPMTYKAAVDLS
NEF_HIV1JR    ------------AITSSNTAATNADCAWLEAYEDEE-VGFPVRPQVPLRPMTYKAAIDLS
NEF_HIV1MA    ------------AAASSSPAANNASC---EPPEEEEVGFPVRPQVPLRPMTYKGAFDLS
NEF_SIVCZ     ------------AITSRNTPETNQTLAWLEEMDNEE-VGFPVRPQVPTRPMTYKAAFDLS
NEF_SIVS4     SEGQYMNTPWRNPATERAKLGYRQQNMDDVDDEDDDLIGVSVHPRVPLRAMTYKLAIDMS
NEF_SIVM1     NQGEYMNTPWRNPAEERKKLPYRKQNIDDIDEEDDDLVGIPVEARVPLRTMSYKLAIDMS
NEF_HIV2SB    QQGDFMNTPWRTPATEKEKESYRQQNMDDVDSDDDDLVGVSDTSRVPLRAMTYRMAVDMS
NEF_HIV2RO    QQGDFMNTPWKDPAAEREKNLYRQQNMDDVDSDDDDQVRVSVTPKVPLRPMTHRLAIDMS
NEF_HIV2ST    QQGDFMNTPWRAPAE-GEKGSYKQQNMDDVDSDDDDLVGVPVTPRVPLREMTYRLARDMS
NEF_HIV2CA    QQGDFMNTPWRAPAAEGKKNAYRQQNMDDIDSDDDDLVGVPATPRVPLRTMTYKLAVDMS
NEF_HIV2BE    QQGEYMNSPWRNPATERQKDLYRQQNMDDVDSDDDDLIGVPVTPRVPRREMTYKLAIDMS
NEF_HIV2D2    --------------NARGAEGGGQQDADESD-EDDEVGAICKTPIVPLRPMTYKLAVDMS
NEF_SIVAI     -----------GKMTPDGRRLQEGDTFDEWDDDEEE-VGFPVQPRVPLRQMTYKLAVDFS
NEF_SIVA1     -----------GNMTPEGRRLQDGDQWDEWSDEEDE-VGFPVRPRVPLRQITYKLAVDFS
NEF_SIVGB     G----TYSEGLDKVQNDPLTKDEKLDLTQQDPEEEEVGFPVCRQVSLRVPSYKDLIDFS
                       .:  .          *. *   ::.  *:*
```

Figure 4

```
NEF_HIV1U4   FFLKEKGGLDGLIHSQKRQEILDLWVYHTQGFFPDWQNYTP--GPGIRYPLTFGWCYKLV
NEF_HIV1EL   HFLKEKGGLEGLIWSKKRQEILDLWVYNTQGIFPDWQNYTP--GPGIRYPLTFGWCYELV
NEF_HIV1ZH   FFLKEKGGLDGLIYSKKRQEILDLWVYHTQGFFPDWHNYTP--GPGTRYPLCFGWCFKLV
NEF_HIV112   HFLKEKGGLEGLIHSQRRQDILDLWIYHTQGYFPDWQNYTP--GPGIRYPLTFGWCYKLV
NEF_HIV1B1   HFLKEKGGLEGLIHSQRRQDILDLWIYHTQGYFPDWQNYTP--GPGVRYPLTFGWCYKLV
NEF_HIV1SC   HFLKEQGGLEGLITP--REDKISLICGSTTHKATSLIGRTTHQGQGSDIPLCFGWCFKLV
NEF_HIV1JR   HFLKEKGGLEGLIYSQKRQDILDLWIYHTQGYFPDWQNYTA--GPGVRFPLTFGWCFKLV
NEF_HIV1MA   HFLKEKGGLDGLVWSPKRQEILDLWVYHTQGYFPDWQNYTP--GPGIRFPLTFGWCFKLV
NEF_SIVCZ    HFLKEKGGLEGLVYSRRRQEILDLWVYHTQGFFPDWQNYTT--GPGTRFPLCFGWCFKLV
NEF_SIVS4    HFIKEKGGLEGIYYNERRHRILDMYLEKEEGIIPDWQNYTS--GPGIRYPMHYGWLWKLV
NEF_SIVM1    HFIKEKGGLEGIYYSARRHRILDIYLEKEEGIIPDWQIHS---GPGIRYLKMFGWLWKLI
NEF_HIV2SB   DLIKDKGGLEGMYYSERRHRILDIYLEKEEGIIPDWQNYTH--GLGVRYPMFFGWLWKLV
NEF_HIV2RO   HLIKTRGGLEGMFYSERRHKILNIYLEKEEGIIADWQNYTH--GPGVRYPMFFGWLWKLV
NEF_HIV2ST   HLIKEKGGLEGLYYSDRRRRVLDIYLEKEEGIIGDWQNYTH--GPGVRYPKFFGWLWKLV
NEF_HIV2CA   HFIKEKGGLEGLFYSERRHRILDIYLEKEEGIIADWQNYTS--GPGVRYPMFFGWLWKLV
NEF_HIV2BE   HFIKEKGGLQGMFYSRRRHRILDIYLEKEEGIIPDWQNYTH--GPGVRYPMYFGWLWKLV
NEF_HIV2D2   HFIKEQGGLEGMYYSERRHRILDTYFENEEGIVSGWQNYTH--GPGIRYPKYFGWLWKLV
NEF_SIVAI    HFLKSKGGLDGIYYSERREKILNLYALNEWGIIDDWQAYSP--GPGIRYPRVFGFCFKLV
NEF_SIVA1    HFLKEKGGLDGIYYSDRRNKILNLYALNEWGIIDDWNAWSK--GPGIRYPRCFGFCFKLV
NEF_SIVGB    HFIKEKGGLGGIYYSRRREEILDLYAENEWGFEPGWQQYTT--GPGTRYPKTFGFLFKLE
             ::*  :***  *:        *. :.          .   :    *  *    :*: ::*

NEF_HIV1U4   PVDPAEVEEAT--GGENNSLLHPICQHGVDD--EEKEVLMWKFDSTLALKHRAYELHPEF
NEF_HIV1EL   PVDPQEVEEDT--EGETNSLLHPICQHGMED--PERQVLKWRFNSRLAFEHKAREMHPEF
NEF_HIV1ZH   PVDPREVEEAN--TGENNCLLHPMSQHGMDD--DEREVLMWKFDSSLARKHLAREMHPEF
NEF_HIV112   PVEPEKLEEAN--KGENTSLLHPVSLHGMDD--PEREVLEWRFDSRLAFHHVARELHPEY
NEF_HIV1B1   PVEPDKVEEAN--KGENTSLLHPVSLHGMDD--PEREVLEWRFDSRLAFHHVARELHPEY
NEF_HIV1SC   PVKPEKIEEAN--EGENNSLLHPMSLHGMED--PEREVLEWRFDNRLAFHHMARDLHPEY
NEF_HIV1JR   PVDPEKVEEAN--EGENNCLLHPMSQHGMDD--PEKEVLVWKFDSKLALHHVARELHPEY
NEF_HIV1MA   PMSPEEVEEAN--EGENNCLLHPISQHGMED--AEREVLKWKFDSSLALRHIAREQHPEY
NEF_SIVCZ    PLTEEQVEQAN--EGDNNCLLHPLCQHGMED--EDKEVLVWRFDSRLALRHIAREQHPEY
NEF_SIVS4    PVDVSDEAQ----EDETHCLVHPAQTYQWDD--PWGEVLAWKFDPELAYSYKAFIKYPEE
NEF_SIVM1    PVNVSDEAQ----EDEEHYLVHPAQTSQWDD--PWGEVLAWKFDPTLAYTYEAYIRYPEE
NEF_HIV2SB   PVTVPQEGE----DTETLCLMHSAQVSRFDD--PHGETLVWKFDPMLAHEYTTFILYPEE
NEF_HIV2RO   PVDVPQEGE----DTETHCLVHPAQTSKFDD--PHGETLVWEFDPLLAYSYEAFIRYPEE
NEF_HIV2ST   PVDVPQEGD----DSETHCLVHPAQTSRFDD--PHGETLVWRFDPTLAFSYEAFIRYPEE
NEF_HIV2CA   PVDTSQEGEDTETDTETHCLLHPAQTSRHDD--MHGETLVWKFDSMLALKYEAFTRYPEE
NEF_HIV2BE   SVELSQEAE----EDEANCLVHPAQTSRHDD--EHGETLVWQFDSMLAYNYKAFTLYPEE
NEF_HIV2D2   PVEVPAATRE---EEETHCLMHPAQISSWDD--IHGETLIWQFDSLLAYDYVAFNRFPEE
NEF_SIVAI    PVDLHEEAR----NCERHCLMHPAQMGEDPDGIDHGEVLVWKFDPKLAVEYRP--DMFKD
NEF_SIVA1    PVALHEEAE----TCERHCLVHPAQLHEDPDGINHGEILAWKFDPMLAVQYDPSREYFTD
NEF_SIVGB    PVSRAIGDEY----AANNHLLHSSQLCPQED--PEGETLMWSGTLILPMTLQH-------
             .:             * *.     *  :    *  :   *  *.
```

Figure 4 Cont'd

```
NEF_HIV1U4    YKD-----------------------------------------------------------
NEF_HIV1EL    YKN-----------------------------------------------------------
NEF_HIV1ZH    YKD-----------------------------------------------------------
NEF_HIV112    FKNC----------------------------------------------------------
NEF_HIV1B1    FKNC----------------------------------------------------------
NEF_HIV1SC    YKDCLTSMCLQGTFRWGISREARLGGTGEWRALRCCI--------------------------
NEF_HIV1JR    YKDC----------------------------------------------------------
NEF_HIV1MA    YKDC----------------------------------------------------------
NEF_SIVCZ     YKD-----------------------------------------------------------
NEF_SIVS4     FGSKSGLSEEEVKRRLTARGLLKWLTRRKQAETAGTFHKGLSWEVLGRSWLERPLILCIN
NEF_SIVM1     FGSKSGLSEKEVKRRLAARGLLEMADRK---ETS-----------------------------
NEF_HIV2SB    FGHKSGMEEDDWKAKLKARGIPFS---------------------------------------
NEF_HIV2RO    FGHKSGLPEEEWKARLKARGIPFS---------------------------------------
NEF_HIV2ST    FGYKSGLPEDEWKARLKARGIPFS---------------------------------------
NEF_HIV2CA    FGHKSGLPEDEWKAKLKARGIPFS---------------------------------------
NEF_HIV2BE    FGHKSGLPEKEWKAKLKARGIPYSE--------------------------------------
NEF_HIV2D2    FGYQSGLPEEEWKARLKARGIPTD---------------------------------------
NEF_SIVAI     MHEHAKR--------------------------------------------------------
NEF_SIVA1     LYSTVGTGN------------------------------------------------------
NEF_SIVGB     ---------------------------------------------------------------

NEF_HIV1U4    ----------------  (SEQ ID NO : 275)
NEF_HIV1EL    ----------------  (SEQ ID NO : 276)
NEF_HIV1ZH    ----------------  (SEQ ID NO : 277)
NEF_HIV112    ----------------  (SEQ ID NO : 278)
NEF_HIV1B1    ----------------  (SEQ ID NO : 1)
NEF_HIV1SC    ----------------  (SEQ ID NO : 279)
NEF_HIV1JR    ----------------  (SEQ ID NO : 280)
NEF_HIV1MA    ----------------  (SEQ ID NO : 281)
NEF_SIVCZ     ----------------  (SEQ ID NO : 282)
NEF_SIVS4     TTAFRSVFSRSAERLAD (SEQ ID NO : 283)
NEF_SIVM1     ----------------  (SEQ ID NO : 284)
NEF_HIV2SB    ----------------  (SEQ ID NO : 285)
NEF_HIV2RO    ----------------  (SEQ ID NO : 286)
NEF_HIV2ST    ----------------  (SEQ ID NO : 287)
NEF_HIV2CA    ----------------  (SEQ ID NO : 288)
NEF_HIV2BE    ----------------  (SEQ ID NO : 289)
NEF_HIV2D2    ----------------  (SEQ ID NO : 290)
NEF_SIVAI     ----------------  (SEQ ID NO : 291)
NEF_SIVA1     ----------------  (SEQ ID NO : 292)
NEF_SIVGB     ----------------  (SEQ ID NO : 293)
```

Figure 4 Cont'd

SEQUENCE LISTING

<160> NUMBER OF SEQ ID NOS: 294

<210> SEQ ID NO 1
<211> LENGTH: 206
<212> TYPE: PRT
<213> ORGANISM: Human immunodeficiency virus type 1

<400> SEQUENCE: 1

Met Gly Gly Lys Trp Ser Lys Ser Ser Val Val Gly Trp Pro Thr Val
1               5                   10                  15

Arg Glu Arg Met Arg Arg Ala Glu Pro Ala Ala Asp Gly Val Gly Ala
            20                  25                  30

Ala Ser Arg Asp Leu Glu Lys His Gly Ala Ile Thr Ser Ser Asn Thr
        35                  40                  45

Ala Ala Thr Asn Ala Ala Cys Ala Trp Leu Glu Ala Gln Glu Glu Glu
    50                  55                  60

Glu Val Gly Phe Pro Val Thr Pro Gln Val Pro Leu Arg Pro Met Thr
65                  70                  75                  80

Tyr Lys Ala Ala Val Asp Leu Ser His Phe Leu Lys Glu Lys Gly Gly
                85                  90                  95

Leu Glu Gly Leu Ile His Ser Gln Arg Arg Gln Asp Ile Leu Asp Leu
            100                 105                 110

Trp Ile Tyr His Thr Gln Gly Tyr Phe Pro Asp Trp Gln Asn Tyr Thr
        115                 120                 125

Pro Gly Pro Gly Val Arg Tyr Pro Leu Thr Phe Gly Trp Cys Tyr Lys
    130                 135                 140

Leu Val Pro Val Glu Pro Asp Lys Val Glu Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
            180                 185                 190

His Val Ala Arg Glu Leu His Pro Glu Tyr Phe Lys Asn Cys
        195                 200                 205

<210> SEQ ID NO 2
<211> LENGTH: 206
<212> TYPE: PRT
<213> ORGANISM: Artificial sequence
<220> FEATURE:
<223> OTHER INFORMATION: E93R HIV-1 Nef mutant

<400> SEQUENCE: 2

Met Gly Gly Lys Trp Ser Lys Ser Ser Val Val Gly Trp Pro Thr Val
1               5                   10                  15

Arg Glu Arg Met Arg Arg Ala Glu Pro Ala Ala Asp Gly Val Gly Ala
            20                  25                  30

Ala Ser Arg Asp Leu Glu Lys His Gly Ala Ile Thr Ser Ser Asn Thr
        35                  40                  45

Ala Ala Thr Asn Ala Ala Cys Ala Trp Leu Glu Ala Gln Glu Glu Glu
    50                  55                  60

Glu Val Gly Phe Pro Val Thr Pro Gln Val Pro Leu Arg Pro Met Thr
65                  70                  75                  80

Tyr Lys Ala Ala Val Asp Leu Ser His Phe Leu Lys Arg Lys Gly Gly
                85                  90                  95

Leu Glu Gly Leu Ile His Ser Gln Arg Arg Gln Asp Ile Leu Asp Leu
            100                 105                 110

```
Trp Ile Tyr His Thr Gln Gly Tyr Phe Pro Asp Trp Gln Asn Tyr Thr
        115                 120                 125

Pro Gly Pro Gly Val Arg Tyr Pro Leu Thr Phe Gly Trp Cys Tyr Lys
    130                 135                 140

Leu Val Pro Val Glu Pro Asp Lys Val Glu Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
            180                 185                 190

His Val Ala Arg Glu Leu His Pro Glu Tyr Phe Lys Asn Cys
        195                 200                 205

<210> SEQ ID NO 3
<211> LENGTH: 16
<212> TYPE: PRT
<213> ORGANISM: Artificial sequence
<220> FEATURE:
<223> OTHER INFORMATION: Nef immunosuppressive domain consensus sequence
<220> FEATURE:
<221> NAME/KEY: MISC_FEATURE
<222> LOCATION: (2)..(2)
<223> OTHER INFORMATION: I, L, V, F or R
<220> FEATURE:
<221> NAME/KEY: MISC_FEATURE
<222> LOCATION: (4)..(4)
<223> OTHER INFORMATION: M, L, or F
<220> FEATURE:
<221> NAME/KEY: MISC_FEATURE
<222> LOCATION: (6)..(6)
<223> OTHER INFORMATION: H, D, or F
<220> FEATURE:
<221> NAME/KEY: MISC_FEATURE
<222> LOCATION: (7)..(7)
<223> OTHER INFORMATION: F or L
<220> FEATURE:
<221> NAME/KEY: MISC_FEATURE
<222> LOCATION: (8)..(8)
<223> OTHER INFORMATION: I or L
<220> FEATURE:
<221> NAME/KEY: MISC_FEATURE
<222> LOCATION: (10)..(10)
<223> OTHER INFORMATION: Any amino acid different from E
<220> FEATURE:
<221> NAME/KEY: MISC_FEATURE
<222> LOCATION: (11)..(11)
<223> OTHER INFORMATION: K, Q, or R
<220> FEATURE:
<221> NAME/KEY: MISC_FEATURE
<222> LOCATION: (13)..(13)
<223> OTHER INFORMATION: G or no amino acid
<220> FEATURE:
<221> NAME/KEY: MISC_FEATURE
<222> LOCATION: (15)..(15)
<223> OTHER INFORMATION: E, D, or R

<400> SEQUENCE: 3

Ala Xaa Asp Xaa Ser Xaa Xaa Xaa Lys Xaa Xaa Gly Xaa Leu Xaa Gly
1               5                   10                  15

<210> SEQ ID NO 4
<211> LENGTH: 43
<212> TYPE: DNA
<213> ORGANISM: Artificial sequence
<220> FEATURE:
<223> OTHER INFORMATION: PCR primer

<400> SEQUENCE: 4
atacatggcc cagccggccg gtggcaagtg gtcaaaaagt agt                       43
```

<210> SEQ ID NO 5
<211> LENGTH: 42
<212> TYPE: DNA
<213> ORGANISM: Artificial sequence
<220> FEATURE:
<223> OTHER INFORMATION: PCR primer

<400> SEQUENCE: 5
atacatggat ccacgcgttc agcagttctt gaagtactcc gg                       42

<210> SEQ ID NO 6
<211> LENGTH: 38
<212> TYPE: DNA
<213> ORGANISM: Artificial sequence
<220> FEATURE:
<223> OTHER INFORMATION: PCR primer

<400> SEQUENCE: 6
atacataccg gtatggagac agacacactc ctgctatg                            38

<210> SEQ ID NO 7
<211> LENGTH: 42
<212> TYPE: DNA
<213> ORGANISM: Artificial sequence
<220> FEATURE:
<223> OTHER INFORMATION: PCR primer

<400> SEQUENCE: 7
atacatggat ccacgcgttc agcagttctt gaagtactcc gg                       42

<210> SEQ ID NO 8
<211> LENGTH: 30
<212> TYPE: DNA
<213> ORGANISM: Artificial sequence
<220> FEATURE:
<223> OTHER INFORMATION: PCR primer

<400> SEQUENCE: 8
atacataccg gtatggagac agacacactc                                     30

<210> SEQ ID NO 9
<211> LENGTH: 37
<212> TYPE: DNA
<213> ORGANISM: Artificial sequence
<220> FEATURE:
<223> OTHER INFORMATION: PCR primer

<400> SEQUENCE: 9
atacatctta agaaagtggc taagatctac agctgcc                             37

<210> SEQ ID NO 10
<211> LENGTH: 33
<212> TYPE: DNA
<213> ORGANISM: Artificial sequence
<220> FEATURE:
<223> OTHER INFORMATION: PCR primer

<400> SEQUENCE: 10
atacatctta agcgaaaggg gggactggaa ggg                                 33

<210> SEQ ID NO 11
<211> LENGTH: 27
<212> TYPE: DNA
<213> ORGANISM: Artificial seuqence
<220> FEATURE:

<223> OTHER INFORMATION: PCR primer

<400> SEQUENCE: 11
atacatacgc gttcagcagt tcttgaa                                              27

<210> SEQ ID NO 12
<211> LENGTH: 50
<212> TYPE: DNA
<213> ORGANISM: Artificial sequence
<220> FEATURE:
<223> OTHER INFORMATION: PCR primer

<400> SEQUENCE: 12
atacatgtcg acccaactag aaccatgggt ggcaagtggt caaaaagtag                     50

<210> SEQ ID NO 13
<211> LENGTH: 27
<212> TYPE: DNA
<213> ORGANISM: Artificial sequence
<220> FEATURE:
<223> OTHER INFORMATION: PCR primer

<400> SEQUENCE: 13
atacatacgc gttcagcagt tcttgaa                                              27

<210> SEQ ID NO 14
<211> LENGTH: 5361
<212> TYPE: DNA
<213> ORGANISM: Artificial sequence
<220> FEATURE:
<223> OTHER INFORMATION: Nef expressing vector

<400> SEQUENCE: 14

| | | |
|---|---|---|
| gcggccgctc tagagagctt ggcccattgc atacgttgta tccatatcat aatatgtaca | 60 |
| tttatattgg ctcatgtcca acattaccgc catgttgaca ttgattattg actagttatt | 120 |
| aatagtaatc aattacgggg tcattagttc atagcccata tatggagttc cgcgttacat | 180 |
| aacttacggt aaatggcccg cctggctgac cgcccaacga cccccgccca ttgacgtcaa | 240 |
| taatgacgta tgttcccata gtaacgccaa tagggacttt ccattgacgt caatgggtgg | 300 |
| agtatttacg gtaaactgcc cacttggcag tacatcaagt gtatcatatg ccaagtacgc | 360 |
| cccctattga cgtcaatgac ggtaaatggc ccgcctggca ttatgcccag tacatgacct | 420 |
| tatgggactt tcctacttgg cagtacatct acgtattagt catcgctatt accatggtga | 480 |
| tgcggttttg gcagtacatc aatgggcgtg gatagcggtt tgactcacgg ggatttccaa | 540 |
| gtctccaccc cattgacgtc aatgggagtt tgttttggca ccaaaatcaa cgggactttc | 600 |
| caaaatgtcg taacaactcc gccccattga cgcaaatggg cggtaggcgt gtacggtggg | 660 |
| aggtctatat aagcagagct cgtttagtga accgtcagat cgcctggaga cgccatccac | 720 |
| gctgttttga cctccataga agacaccggg accgatccag cctccggtcg accgatcctg | 780 |
| agaacttcag ggtgagtttg ggacccttg attgttcttt cttttcgct attgtaaaat | 840 |
| tcatgttata tggagggggc aaagttttca gggtgttgtt tagaatggga agatgtccct | 900 |
| tgtatcacca tggaccctca tgataatttt gtttctttca ctttctactc tgttgacaac | 960 |
| cattgtctcc tcttattttc ttttcatttt ctgtaacttt tcgttaaac tttagcttgc | 1020 |
| atttgtaacg aattttaaa ttcacttttg tttatttgtc agattgtaag tactttctct | 1080 |
| aatcactttt ttttcaaggc aatcagggta tattatattg tacttcagca cagttttaga | 1140 |
| gaacaattgt tataattaaa tgataaggta gaatatttct gcatataaat tctggctggc | 1200 |

```
gtggaaatat tcttattggt agaaacaact acaccctggt catcatcctg cctttctctt    1260
tatggttaca atgatataca ctgtttgaga tgaggataaa atactctgag tccaaaccgg    1320
gcccctctgc taaccatgtt catgccttct tctctttcct acagctcctg ggcaacgtgc    1380
tggttgttgt gctgtctcat cattttggca aagaattcct cgacggatcc ctcgacccaa    1440
ctagaaccat ggggtgggag cagcatctcg agacctggaa aaacatggag caatcacaag    1500
tagcaataca gcagctacca atgctgcttg tgcctggcta aagcacaag aggaggagga    1560 ggtgggtttt ccagtcacac ctcaggtacc tttaagacca atgacttaca aggcagctgt    1620
agatcttagc cactttctta aggaaaaggg gggactggaa gggctaattc actcccaacg    1680
aagacaagat atccttgatc tgtggatcta ccacacacaa ggctacttcc ctgattggca    1740
gaactacaca ccagggccag gggtcagata tccactgacc tttggatggt gctacaagct    1800
agtaccagtt gagccagata aggtagaaga ggccaataaa ggagagaaca ccagcttgtt    1860
acaccctgtg agcctgcatg gaatggatga ccctgagaga gaagtgttag agtggaggtt    1920
tgacagccgc ctagcatttc atcacgtggc ccgagagctg catccggagt acttcaagaa    1980
ctgctgaacg cgtcaggtgc aggctgccta tcagaaggtg gtggctggtg tggccaatgc    2040
cctggctcac aaataccact gagatctttt tccctctgcc aaaaattatg gggacatcat    2100
gaagcccctt gagcatctga cttctggcta ataaaggaaa tttattttca ttgcaatagt    2160
gtgttggaat ttttgtgtc tctcactcgg aaggacatat gggagggcaa atcatttaaa    2220
acatcagaat gagtatttgg tttagagttt ggcaacatat gcccatatgc tggctgccat    2280
gaacaaaggt tggctataaa gaggtcatca gtatatgaaa cagccccctg ctgtccattc    2340
cttattccat agaaaagcct tgacttgagg ttagattttt tttatatttt gttttgtgtt    2400
atttttttct ttaacatccc taaaattttc cttacatgtt ttactagcca gattttttcct   2460 cctctcctga ctactcccag tcatagctgt ccctcttctc ttatggagat ccctcgacgg    2520
atcggccgca attcgtaatc atgtcatagc tgtttcctgt gtgaaattgt tatccgctca    2580
caattccaca acatacga gccgaagca taaagtgtaa agcctggggt gcctaatgag    2640
tgagctaact cacattaatt gcgttgcgct cactgcccgc tttccagtcg ggaaacctgt    2700
cgtgccagct gcattaatga atcggccaac gcgcggggag aggcggtttg cgtattgggc    2760
gctcttccgc ttcctcgctc actgactcgc tgcgctcggt cgttcggctg cggcgagcgg    2820
tatcagctca ctcaaaggcg gtaatacggt tatccacaga atcaggggat aacgcaggaa    2880
agaacatgtg agcaaaaggc cagcaaaagg ccaggaaccg taaaaaggcc gcgttgctgg    2940 cgttttttcca taggctccgc cccctgacg agcatcacaa aaatcgacgc tcaagtcaga   3000
ggtggcgaaa cccgacagga ctataaagat accaggcgtt tccccctgga agctccctcg    3060
tgcgctctcc tgttccgacc ctgccgctta ccggatacct gtccgccttt ctcccttcgg    3120
gaagcgtggc gctttctcat agctcacgct gtaggtatct cagttcggtg taggtcgttc    3180
gctccaagct gggctgtgtg cacgaacccc ccgttcagcc cgaccgctgc gccttatccg    3240
gtaactatcg tcttgagtcc aacccggtaa gacacgactt atcgccactg gcagcagcca    3300
ctggtaacag gattagcaga gcgaggtatg taggcggtgc tacagagttc ttgaagtggt    3360
ggcctaacta cggctacact agaagaacag tatttggtat ctgcgctctg ctgaagccag    3420
ttaccttcgg aaaaagagtt ggtagctctt gatccggcaa acaaaccacc gctggtagcg    3480
gtggtttttt tgtttgcaag cagcagatta cgcgcagaaa aaaaggatct caagaagatc    3540
```

-continued

| | |
|---|---|
| ctttgatctt ttctacgggg tctgacgctc agtggaacga aaactcacgt taagggattt | 3600 |
| tggtcatgag attatcaaaa aggatcttca cctagatcct tttaaattaa aaatgaagtt | 3660 |
| ttaaatcaat ctaaagtata tatgagtaaa cttggtctga cagttaccaa tgcttaatca | 3720 |
| gtgaggcacc tatctcagcg atctgtctat ttcgttcatc catagttgcc tgactccccg | 3780 |
| tcgtgtagat aactacgata cgggagggct taccatctgg ccccagtgct gcaatgatac | 3840 |
| cgcgagaccc acgctcaccg gctccagatt tatcagcaat aaaccagcca gccgaaggg | 3900 |
| ccgagcgcag aagtggtcct gcaactttat ccgcctccat ccagtctatt aattgttgcc | 3960 |
| gggaagctag agtaagtagt tcgccagtta atagtttgcg caacgttgtt gccattgcta | 4020 |
| caggcatcgt ggtgtcacgc tcgtcgtttg gtatggcttc attcagctcc ggttcccaac | 4080 |
| gatcaaggcg agttacatga tcccccatgt tgtgcaaaaa agcggttag ctccttcgt | 4140 |
| cctccgatcg ttgtcagaag taagttggcc gcagtgttat cactcatggt tatggcagca | 4200 |
| ctgcataatt ctcttactgt catgccatcc gtaagatgct tttctgtgac tggtgagtac | 4260 |
| tcaaccaagt cattctgaga atagtgtatg cggcgaccga gttgctcttg cccggcgtca | 4320 |
| atacggggata ataccgcgcc acatagcaga actttaaaag tgctcatcat tggaaaacgt | 4380 |
| tcttcggggc gaaaactctc aaggatctta ccgctgttga tccagttc gatgtaaccc | 4440 |
| actcgtgcac ccaactgatc ttcagcatct tttactttca ccagcgtttc tgggtgagca | 4500 |
| aaaacaggaa ggcaaaatgc cgcaaaaaag ggaataaggg cgacacggaa atgttgaata | 4560 |
| ctcatactct ccttttttca atattattga agcatttatc agggttattg tctcatgagc | 4620 |
| ggatacatat ttgaatgtat ttagaaaaat aaacaaatag gggttccgcg cacatttccc | 4680 |
| cgaaaagtgc cacctaaatt gtaagcgtta atattttgtt aaaattcgcg ttaaattttt | 4740 |
| gttaaatcag ctcattttt aaccaatagg ccgaaatcgg caaaatccct tataaatcaa | 4800 |
| aagaatagac cgagataggg ttgagtgttg ttccagtttg gaacaagagt ccactattaa | 4860 |
| agaacgtgga ctccaacgtc aaagggcgaa aaaccgtcta tcagggcgat ggcccactac | 4920 |
| gtgaaccatc accctaatca agttttttgg ggtcgaggtg ccgtaaagca ctaaatcgga | 4980 |
| accctaaagg gagcccccga tttagagctt gacggggaaa gccggcgaac gtggcgagaa | 5040 |
| aggaagggaa gaaagcgaaa ggagcgggcg ctagggcgct ggcaagtgta gcggtcacgc | 5100 |
| tgcgcgtaac caccacccc gccgcgctta atgcgccgct acaggcgcg tcccattcgc | 5160 |
| cattcaggct gcgcaactgt tgggaagggc gatcggtgcg ggcctcttcg ctattacgcc | 5220 |
| agctggcgaa aggggatgt gctgcaaggc gattaagttg ggtaacgcca gggttttccc | 5280 |
| agtcacgacg ttgtaaaacg acggccagtg agcgcgcgta atacgactca ctatagggcg | 5340 |
| aattggagct ccaccgcggt g | 5361 |

<210> SEQ ID NO 15
<211> LENGTH: 5361
<212> TYPE: DNA
<213> ORGANISM: Artificial sequence
<220> FEATURE:
<223> OTHER INFORMATION: E93R Nef mutant expressing vector

<400> SEQUENCE: 15

| | |
|---|---|
| gcggccgctc tagagagctt ggcccattgc atacgttgta tccatatcat aatatgtaca | 60 |
| tttatattgg ctcatgtcca acattaccgc catgttgaca ttgattattg actagttatt | 120 |
| aatagtaatc aattacgggg tcattagttc atagcccata tatggagttc cgcgttacat | 180 |
| aacttacggt aaatggcccg cctggctgac cgcccaacga cccccgccca ttgacgtcaa | 240 |

-continued

```
taatgacgta tgttcccata gtaacgccaa tagggacttt ccattgacgt caatgggtgg    300
agtatttacg gtaaactgcc cacttggcag tacatcaagt gtatcatatg ccaagtacgc    360
cccctattga cgtcaatgac ggtaaatggc ccgcctggca ttatgcccag tacatgacct    420
tatgggactt tcctacttgg cagtacatct acgtattagt catcgctatt accatggtga    480
tgcggttttg gcagtacatc aatgggcgtg gatagcggtt tgactcacgg ggatttccaa    540
gtctccaccc cattgacgtc aatgggagtt tgttttggca ccaaaatcaa cgggactttc    600
caaaatgtcg taacaactcc gccccattga cgcaaatggg cggtaggcgt gtacggtggg    660
aggtctatat aagcagagct cgtttagtga accgtcagat cgcctggaga cgccatccac    720
gctgttttga cctccataga agacaccggg accgatccag cctccggtcg accgatcctg    780
agaacttcag ggtgagtttg ggacccttga ttgttctttc tttttcgct attgtaaaat    840 tcatgttata tggaggggc aaagttttca gggtgttgtt tagaatggga agatgtccct    900
tgtatcacca tggaccctca tgataatttt gtttctttca ctttctactc tgttgacaac    960
cattgtctcc tcttattttc ttttcatttt ctgtaacttt ttcgttaaac tttagcttgc   1020
atttgtaacg aattttttaaa ttcacttttg tttatttgtc agattgtaag tactttctct   1080 aatcacttt tttcaaggc aatcagggta tattatattg tacttcagca cagttttaga   1140
gaacaattgt tataattaaa tgataaggta gaatatttct gcatataaat tctggctggc   1200
gtggaaatat tcttattggt agaaacaact acaccctggt catcatcctg cctttctctt   1260
tatggttaca atgatataca ctgtttgaga tgaggataaa atactctgag tccaaaccgg   1320
gcccctctgc taaccatgtt catgccttct tctctttcct acagctcctg ggcaacgtgc   1380
tggttgttgt gctgtctcat cattttggca aagaattcct cgacggatcc ctcgacccaa   1440
ctagaaccat ggggtgggag cagcatctcg agacctggaa aaacatggag caatcacaag   1500
tagcaataca gcagctacca atgtgcttg tgcctggcta gaagcacaag aggaggagga   1560
ggtgggtttt ccagtcacac ctcaggtacc tttaagacca atgacttaca aggcagctgt   1620
agatcttagc cactttctta agcgaaaggg gggactggaa gggctaattc actcccaacg   1680
aagacaagat atccttgatc tgtggatcta ccacacacaa ggctacttcc ctgattggca   1740
gaactacaca ccagggccag ggtcagata tccactgacc tttggatggt gctacaagct   1800
agtaccagtt gagccagata aggtagaaga ggccaataaa ggagagaaca ccagcttgtt   1860
acaccctgtg agcctgcatg gaatggatga ccctgagaga aagtgttag agtggaggtt   1920 tgacagccgc ctagcatttc atcacgtggc ccgagagctg catccggagt acttcaagaa   1980
ctgctgaacg cgtcaggtgc aggctgccta tcagaaggtg gtggctggtg tggccaatgc   2040
cctggctcac aaataccact gagatctttt tccctctgcc aaaaattatg gggacatcat   2100 gaagccccctt gagcatctga cttctggcta ataaggaaa tttattttca ttgcaatagt   2160
gtgttggaat tttttgtgtc tctcactcgg aaggacatat gggagggcaa atcatttaaa   2220
acatcagaat gagtatttgg tttagagttt ggcaacatat gcccatatgc tggctgccat   2280
gaacaaaggt tggctataaa gaggtcatca gtatatgaaa cagcccctg ctgtccattc   2340 cttattccat agaaaagcct tgacttgagg ttagattttt tttatatttt gttttgtgtt   2400
atttttttct ttaacatccc taaaattttc cttacatgtt ttactagcca gattttttcct   2460 cctctcctga ctactcccag tcatagctgt ccctcttctc ttatggagat ccctcgacgg   2520
atcggccgca attcgtaatc atgtcatagc tgtttcctgt gtgaaattgt tatccgctca   2580
```

```
caattccaca caacatacga gccggaagca taaagtgtaa agcctggggt gcctaatgag    2640
tgagctaact cacattaatt gcgttgcgct cactgcccgc tttccagtcg ggaaacctgt    2700
cgtgccagct gcattaatga atcggccaac gcgcgggag aggcggtttg cgtattgggc    2760
gctcttccgc ttcctcgctc actgactcgc tgcgctcggt cgttcggctg cggcgagcgg    2820
tatcagctca ctcaaaggcg gtaatacggt tatccacaga atcaggggat aacgcaggaa    2880
agaacatgtg agcaaaaggc cagcaaaagg ccaggaaccg taaaaaggcc gcgttgctgg    2940
cgtttttcca taggctccgc cccctgacg agcatcacaa aaatcgacgc tcaagtcaga    3000
ggtggcgaaa cccgacagga ctataaagat accaggcgtt ccccctgga agctccctcg    3060
tgcgctctcc tgttccgacc ctgccgctta ccggatacct gtccgccttt ctcccttcgg    3120
gaagcgtggc gctttctcat agctcacgct gtaggtatct cagttcggtg taggtcgttc    3180
gctccaagct gggctgtgtg cacgaacccc ccgttcagcc cgaccgctgc gccttatccg    3240
gtaactatcg tcttgagtcc aacccggtaa gacacgactt atcgccactg gcagcagcca    3300
ctggtaacag gattagcaga gcgaggtatg taggcggtgc tacagagttc ttgaagtggt    3360
ggcctaacta cggctacact agaagaacag tatttggtat ctgcgctctg ctgaagccag    3420
ttaccttcgg aaaaagagtt ggtagctctt gatccggcaa acaaaccacc gctggtagcg    3480
gtggtttttt tgtttgcaag cagcagatta cgcgcagaaa aaaggatct caagaagatc    3540
ctttgatctt ttctacgggg tctgacgctc agtggaacga aaactcacgt taagggattt    3600
tggtcatgag attatcaaaa aggatcttca cctagatcct tttaaattaa aaatgaagtt    3660
ttaaatcaat ctaaagtata tatgagtaaa cttggtctga cagttaccaa tgcttaatca    3720
gtgaggcacc tatctcagcg atctgtctat ttcgttcatc catagttgcc tgactccccg    3780
tcgtgtagat aactacgata cgggagggct taccatctgg ccccagtgct gcaatgatac    3840
cgcgagaccc acgctcaccg gctccagatt tatcagcaat aaaccagcca gccggaaggg    3900
ccgagcgcag aagtggtcct gcaactttat ccgcctccat ccagtctatt aattgttgcc    3960
gggaagctag agtaagtagt tcgccagtta atagtttgcg caacgttgtt gccattgcta    4020
caggcatcgt ggtgtcacgc tcgtcgtttg gtatggcttc attcagctcc ggttcccaac    4080
gatcaaggcg agttacatga tcccccatgt tgtgcaaaaa agcgggttag ctccttcggt    4140
cctccgatcg ttgtcagaag taagttggcc gcagtgttat cactcatggt tatggcagca    4200
ctgcataatt ctcttactgt catgccatcc gtaagatgct tttctgtgac tggtgagtac    4260
tcaaccaagt cattctgaga atagtgtatg cggcgaccga gttgctcttg cccggcgtca    4320
atacgggata ataccgcgcc acatagcaga actttaaaag tgctcatcat tggaaaacgt    4380
tcttcggggc gaaaactctc aaggatctta ccgctgttga tccagttc gatgtaaccc     4440
actcgtgcac ccaactgatc ttcagcatct tttactttca ccagcgtttc tgggtgagca    4500
aaaacaggaa ggcaaaatgc cgcaaaaaag ggaataaggg cgacacggaa atgttgaata    4560
ctcatactct ccttttttca atattattga agcatttatc agggttattg tctcatgagc    4620
ggatacatat ttgaatgtat ttagaaaaat aaacaaatag gggttccgcg cacatttccc    4680
cgaaaagtgc cacctaaatt gtaagcgtta atattttgtt aaaattcgcg ttaaattttt    4740
gttaaatcag ctcattttttt aaccaatagg ccgaaatcgg caaaatccct tataaatcaa    4800
aagaatagac cgagataggg ttgagtgttg ttccagtttg gaacaagagt ccactattaa    4860
agaacgtgga ctccaacgtc aaagggcgaa aaaccgtcta tcaggcgat ggcccactac    4920
gtgaaccatc accctaatca agttttttgg ggtcgaggtg ccgtaaagca ctaaatcgga    4980
```

-continued

```
acccuaaagg gagcccccga tttagagctt gacggggaaa gccggcgaac gtggcgagaa    5040
aggaagggaa gaaagcgaaa ggagcgggcg ctagggcgct ggcaagtgta gcggtcacgc    5100
tgcgcgtaac caccacaccc gccgcgctta atgcgccgct acagggcgcg tcccattcgc    5160
cattcaggct gcgcaactgt tgggaagggc gatcggtgcg ggcctcttcg ctattacgcc    5220
agctggcgaa aggggatgt gctgcaaggc gattaagttg ggtaacgcca gggttttccc    5280
agtcacgacg ttgtaaaacg acggccagtg agcgcgcgta atacgactca ctatagggcg    5340
aattggagct ccaccgcggt g                                              5361
```

<210> SEQ ID NO 16
<211> LENGTH: 10216
<212> TYPE: DNA
<213> ORGANISM: Artificial sequence
<220> FEATURE:
<223> OTHER INFORMATION: pDFG-expNef vector expressing Nef fused to an
      export signal sequence

<400> SEQUENCE: 16

```
ggatccgcgg gattagtcca atttgttaaa gacaggatat cagtggtcca ggctctagtt      60
ttgactcaac aatatcacca gctgaagcct atagagtacg agccatagat aaaataaaag     120
atttttattta gtctccagaa aaggggggga atgaaagacc ccacctgtag gtttggcaag     180
ctagcttaag taacgccatt tgcaaggca tggaaaaata cataactgag aatagagaag     240
ttcagatcaa ggtcaggaac agatggaaca gctgaatatg gccaaacag gatatctgtg     300
gtaagcagtt cctgccccgg ctcagggcca agaacagatg gaacagctga atatgggcca    360
aacaggatat ctgtggtaag cagttcctgc cccggctcag gccaagaac agatggtccc     420
cagatgcggt ccagccctca gcagtttcta gagaaccatc agatgtttcc agggtgcccc    480
aaggacctga aatgaccctg tgccttattt gaactaacca atcagttcgc ttctcgcttc    540
tgttcgcgcg cttctgctcc ccgagctcaa taaaagagcc cacaaccccct cactcggggc    600
gccagtcctc cgattgactg agtcgcccgg gtacccgtgt atccaataaa ccctcttgca    660
gttgcatccg acttgtggtc tcgctgttcc ttgggagggt ctcctctgag tgattgacta    720
cccgtcagcg ggggtctttc acatgcagca tgtatcaaaa ttaatttggt ttttttttcttt   780
aagtatttac attaaatggc catagtactt aaagttacat tggcttcctt gaaataaaca    840
tggagtattc agaatgtgtc ataaatattt ctaatttaa gatagtatct ccattggctt    900
tctactttt ctttttatttt ttttttgtcct ctgtcttcca tttgttgttg ttgttgtttg    960
tttgtttgtt tgttggttgg ttggttaatt tttttttaaa gatcctacac tatagttcaa   1020
gctagactat tagctactct gtaacccagg gtgaccttga agtcatgggt agcctgctgt   1080
tttagccttc ccacatctaa gattacaggt atgagctatc atttttggta tattgattga   1140
ttgattgatt gatgtgtgtg tgtgtgattg tgtttgtgtg tgtgattgtg tatatgtgtg   1200
tatgttgtg tgtgattgtg tgtatgtatg tttgtgtgtg attgtgtgtg tgtgattgtg   1260
catgtgtgtg tgtgtgattg tgtttatgtg tatgattgtg tgtgtgtgtg tgtgtgtgtg   1320
tgtgtgtgtg tgtgtgtgtg tgttgtgtat atatatttat ggtagtgaga ggcaacgctc   1380
cggctcaggt gtcaggttgg tttttgagac agagtctttc acttagcttg gaattcttga   1440
agacgaaagg gcctcgtgat acgcctattt ttataggtta atgtcatgat aataatggtt   1500
tcttagacgt caggtggcac ttttcgggga atgtgcgcg gaaccccctat ttgtttattt   1560
ttctaaatac attcaaatat gtatccgctc atgagacaat aaccctgata aatgcttcaa   1620
```

```
taatattgaa aaaggaagag tatgagtatt caacatttcc gtgtcgccct tattcccttt    1680
tttgcggcat tttgccttcc tgttttttgct cacccagaaa cgctggtgaa agtaaaagat   1740
gctgaagatc agttgggtgc acgagtgggt tacatcgaac tggatctcaa cagcggtaag   1800
atccttgaga gttttcgccc cgaagaacgt tttccaatga tgagcacttt taaagttctg   1860
ctatgtggcg cggtattatc ccgtgttgac gccgggcaac agcaactcgg tcgccgcata   1920
cactattctc agaatgactt ggttgagtac tcaccagtca cagaaaagca tcttacggat   1980
ggcatgacag taagagaatt atgcagtgct gccataacca tgagtgataa cactgcggcc   2040
aacttacttc tgacaacgat cggaggaccg aaggagctaa ccgcttttt gcacaacatg     2100 ggggatcatg taactcgcct tgatcgttgg gaaccggagc tgaatgaagc cataccaaac   2160
gacgagcgtg acaccacgat gcctgcagca atggcaacaa cgttgcgcaa actattaact   2220
ggcgaactac ttactctagc ttcccggcaa caattaatag actggatgga ggcggataaa   2280
gttgcaggac cacttctgcg ctcggccctt ccggctggct ggtttattgc tgataaatct   2340
ggagccggtg agcgtgggtc tcgcggtatc attgcagcac tggggccaga tggtaagccc   2400
tcccgtatcg tagttatcta cacgacgggg agtcaggcaa ctatggatga acgaaataga   2460
cagatcgctg agataggtgc ctcactgatt aagcattggt aactgtcaga ccaagtttac   2520
tcatatatac tttagattga tttaaaactt catttttaat ttaaaaggat ctaggtgaag   2580
atcctttttg ataatctcat gaccaaaatc ccttaacgtg agttttcgtt ccactgagcg   2640
tcagaccccg tagaaaagat caaaggatct cttgagatcc ttttttttct gcgcgtaatc   2700
tgctgcttgc aaacaaaaaa accaccgcta ccagcggtgg tttgtttgcc ggatcaagag   2760
ctaccaactc tttttccgaa ggtaactggc ttcagcagag cgcagatacc aaatactgtc   2820
cttctagtgt agccgtagtt aggccaccac ttcaagaact ctgtagcacc gcctacatac   2880
ctcgctctgc taatcctgtt accagtggct gctgccagtg gcgataagtc gtgtcttacc   2940
gggttggact caagacgata gttaccggat aaggcgcagc ggtcgggctg aacggggggt   3000
tcgtgcacac agcccagctt ggagcgaacg acctacaccg aactgagata cctacagcgt    3060
gagctatgag aaagcgccac gcttcccgaa gggagaaagg cggacaggta tccggtaagc   3120
ggcagggtcg gaacaggaga gcgcacgagg gagcttccag ggggaaacgc ctggtatctt   3180
tatagtcctg tcgggtttcg ccacctctga cttgagcgtc gatttttgtg atgctcgtca   3240 gggggggcgga gcctatggaa aaacgccagc aacgcggcct ttttacggtt cctggccttt   3300
tgctggcctt ttgctcacat gttctttcct gcgttatccc ctgattctgt ggataaccgt   3360
attaccgcct ttgagtgagc tgataccgct cgccgcagcc gaacgaccga gcgcagcgag   3420
tcagtgagcg aggaagcgga agagcgcctg atgcggtatt ttctccttac gcatctgtgc   3480
ggtatttcac accgcatata tggtgcactc tcagtacaat ctgctctgat gccgcatagt   3540
taagccagta tacactccgc tatcgctacg tgactgggtc atggctgcgc ccgacaccc     3600 gccaacaccc gctgacgcgc cctgacgggc ttgtctgctc ccggcatccg cttacagaca   3660
agctgtgacc gtctccggga gctgcatgtg tcagaggttt tcaccgtcat caccgaaacg   3720
cgcgaggcag ctgcggtaaa gctcatcagc gtggtcgtga agcgattcac agatgtctgc   3780
ctgttcatcc gcgtccagct cgttgagttt ctccagaagc gttaatgtct ggcttctgat   3840
aaagcgggcc atgttaaggg cggttttttc ctgtttggtc acttgatgcc tccgtgtaag   3900
ggggaatttc tgttcatggg ggtaatgata ccgatgaaac gagagaggat gctcacgata   3960
```

```
cgggttactg atgatgaaca tgcccggtta ctggaacgtt gtgagggtaa acaactggcg    4020
gtatggatgc ggcgggacca gagaaaaatc actcagggtc aatgccagcg cttcgttaat    4080
acagatgtag gtgttccaca gggtagccag cagcatcctg cgatgcagat ccggaacata    4140
atggtgcagg gcgctgactt ccgcgttttcc agactttacg aaacacggaa accgaagacc    4200
attcatgttg ttgctcaggt cgcagacgtt ttgcagcagc agtcgcttca cgttcgctcg    4260
cgtatcggtg attcattctg ctaaccagta aggcaacccc gccagcctag ccgggtcctc    4320
aacgacagga gcacgatcat gcgcacccgt ggccaggacc caacgctgcc cgagatgcgc    4380
cgcgtgcggc tgctggagat ggcggacgcg atggatatgt tctgccaagg gttggtttgc    4440
gcattcacag ttctccgcaa gaattgattg gctccaattc ttggagtggt gaatccgtta    4500
gcgaggtgcc gccggcttcc attcaggtcg aggtggcccg gctccatgca ccgcgacgca    4560
acgcggggag gcagacaagg tataggcgg cgcctacaat ccatgccaac ccgttccatg    4620
tgctcgccga ggcggcataa atcgccgtga cgatcagcgg tccagtgatc gaagttaggc    4680
tggtaagagc cgcgagcgat ccttgaagct gtccctgatg gtcgtcatct acctgcctgg    4740
acagcatggc ctgcaacgcg ggcatcccga tgccgccgga agcgagaaga atcataatgg    4800
ggaaggccat ccagcctcgc gtcgcgaacg ccagcaagac gtagcccagc gcgtcggccg    4860
ccatgccggc gataatggcc tgcttctcgc cgaaacgttt ggtggcggga ccagtgacga    4920
aggcttgagc gagggcgtgc aagattccga ataccgcaag cgacaggccg atcatcgtcg    4980
cgctccagcg aaagcggtcc tcgccgaaaa tgacccagag cgctgccggc acctgtccta    5040
cgagttgcat gataaagaag acagtcataa gtgcggcgac gatagtcatg ccccgcgccc    5100
accggaagga gctgactggg ttgaaggctc tcaagggcat cggtcgacgc tctcccttat    5160
gcgactcctg cattaggaag cagcccagta gtaggttgag gccgttgagc accgccgccg    5220
caaggaatgg tgcatgcaag gagatggcgc ccaacagtcc cccggccacg gggcctgcca    5280
ccatacccac gccgaaacaa gcgctcatga gcccgaagtg gcgagcccga tcttccccat    5340
cggtgatgtc ggcgatatag gcgccagcaa ccgcacctgt ggcgccggtg atgccggcca    5400
cgatgcgtcc ggcgtagagg atcgatccac aggacgggtg tggtcgccat gatcgcgtag    5460
tcgatagtgg ctccaagtag cgaagcgagc aggactgggc ggcggccaaa gcggtcggac    5520
agtgctccga gaacgggtgc gcatagaaat tgcatcaacg catatagcgc tagcagcacg    5580
ccatagtgac tggcgatgct gtcggaatgg acgatatccc gcaagaggcc cggcagtacc    5640
ggcataacca agcctatgcc tacagcatcc agggtgacgg tgccgaggat gacgatgagc    5700
gcattgttag atttcataca cggtgcctga ctgcgttagc aatttaactg tgataaacta    5760
ccgcattaaa gctttgctct taggagtttc ctaatacatc ccaaactcaa atatataaag    5820
catttgactt gttctatgcc ctaggggggcg ggggaagct aagccagctt tttttaacat    5880
ttaaaatgtt aattccattt taaatgcaca gatgttttta tttcataagg gtttcaatgt    5940
gcatgaatgc tgcaatattc ctgttaccaa agctagtata aataaaaata gataaacgtg    6000
gaaattactt agagtttctg tcattaacgt ttccttcctc agttgacaac ataaatgcgc    6060
tgctgagaag ccagtttgca tctgtcagga tcaatttccc attatgccag tcatattaat    6120
tactagtcaa ttagttgatt tttattttg acatatacat gtgaaagacc ccacctgtag    6180
gtttggcaag ctagcttaag taacgccatt ttgcaaggca tggaaaaata cataactgag    6240
agggccaaac aggatatctg tggtaagcag ttcatagaaa agttcagatc aaggtcagga    6300
acagatggaa cagctgaata tctgccccgg ctcagggcca agaacagatg gaacagctga    6360
```

-continued

```
atatgggcca aacaggatat ctgtggtaag cagttcctgc cccggctcag ggccaagaac    6420
agatggtccc cagatgcggt ccagccctca gcagtttcta gagaaccatc agatgtttcc    6480
agggtgcccc aaggacctga aatgaccctg tgccttattt gaactaacca atcagttcgc    6540
ttctcgcttc tgttcgcgcg cttctgctcc ccgagctcaa taaaagagcc cacaacccct    6600
cactcggcgc gccagtcctc cgattgactg agtcgcccgg gtacccgtgt atccaataaa    6660
ccctcttgca gttgcatccg acttgtggtc tcgctgttcc ttgggagggt ctcctctgag    6720
tgattgacta cccgtcagcg ggggtctttc atttgggggc tcgtccggga tcgggagacc    6780
cctgcccagg gaccaccgac ccaccaccgg gaggtaagct ggccagcaac ttatctgtgt    6840
ctgtccgatt gtctagtgtc tatgactgat tttatgcgcc tgcgtcggta ctagttagct    6900
aactagctct gtatctggcg gacccgtggt ggaactgacg agttcggaac acccggccgc    6960
aaccctggga gacgtcccag ggacttcggg ggccgttttt gtggcccgac ctgagtccaa    7020
aaatcccgat cgtttggac tctttggtgc accccctta gaggagggat atgtggttct    7080
ggtaggagac gagaacctaa aacagttccc gcctccgtct gaattttgc tttcggtttg    7140 ggaccgaagc cgcgccgcgc gtcttgtctg ctgcagcatc gttctgtgtt gtctctgtct    7200
gactgtgttt ctgtatttgt ctgaaaatat gggcccgccg cggcgggcca gactgttacc    7260
actcccttaa gtttgacctt aggtcactgg aaagatgtcg agcggatcgc tcacaaccag    7320
tcggtagatg tcaagaagag acgttgggtt accttctgct ctgcagaatg ccaacctttt    7380
aacgtcggat ggccgcgaga cggcacctt aaccgagacc tcatcaccca ggttaagatc    7440
aaggtctttt cacctggccc gcatggacac ccagaccagg tccctacat cgtgacctgg    7500 gaagccttgg cttttgaccc ccctccctgg gtcaagccct tgtacaccc taagcctccg    7560 cctcctcttc ctccatccgc cccgtctctc ccccttgaac ctcctcgttc gaccccgcct    7620
cgatcctccc tttatccagc cctcactcct tctctaggcg cccccatatg gccatatgag    7680
atcttatatg gggcacccc gccccttgta aacttccctg accctgacat gacaagagtt    7740
actaacagcc cctctctcca agctcactta caggctctct acttagtcca gcacgaagtc    7800
tggagacctc tggcggcagc ctaccaagaa caactggacc gaccggtatg gagacagaca    7860
cactcctgct atgggtactg ctgctctggg ttccaggttc cactggtgac gcggcccagc    7920
cggccggtgg caagtggtca aaaagtagtg tggttggatg gcctactgta agggaaagaa    7980
tgagacgagc tgagccagca gcagatgggg tgggagcagc atctcgagac ctggaaaaac    8040
atggagcaat cacaagtagc aatacagcag ctaccaatgc tgcttgtgcc tggctagaag    8100
cacaagagga ggaggaggtg ggttttccag tcacacctca ggtacctta agaccaatga    8160 cttacaaggc agctgtagat cttagccact ttcttaagga aaaggggga ctggaagggc    8220 taattcactc ccaacgaaga caagatatcc ttgatctgtg gatctaccac acacaaggct    8280
acttccctga ttggcagaac tacacaccag ggccagggt cagatatcca ctgacctttg    8340
gatggtgcta caagctagta ccagttgagc cagataaggt agaagaggcc aataaaggag    8400
agaacaccag cttgttacac cctgtgagcc tgcatggaat ggatgaccct gagagagaag    8460
tgttagagtg gaggtttgac agccgcctag catttcatca cgtggcccga gagctgcatc    8520
cggagtactt caagaactgc tgaacgcgtt gactcgagaa ttccggcccc tctccctccc    8580 cccccctaa cgttactggc cgaagccgct tggaataagg ccggtgtgcg tttgtctata    8640
tgttattttc caccatattg ccgtcttttg gcaatgtgag ggcccggaaa cctggccctg    8700
```

```
tcttcttgac gagcattcct aggggtctttt cccctctcgc caaaggaatg caaggtctgt   8760
tgaatgtcgt gaaggaagca gttcctctgg aagcttcttg aagacaaaca acgtctgtag   8820
cgacccttttg caggcagcgg aaccccccac ctggcgacag gtgcctctgc ggccaaaagc  8880
cacgtgtata agatacacct gcaaaggcgg cacaacccca gtgccacgtt gtgagttgga   8940
tagttgtgga aagagtcaaa tggctctcct caagcgtatt caacaagggg ctgaaggatg   9000
cccagaaggt accccattgt atgggatctg atctggggcc tcggtgcaca tgctttacat   9060
gtgtttagtc gaggttaaaa aacgtctagg ccccccgaac cacggggacg tggtttttcct  9120
ttgaaaaaca cgatgataat atggccacaa ccatggaaaa agcctgaact caccgcgacg   9180
tctgtcgaga agtttctgat cgaaaagttc gacagcgtct ccgacctgat gcagctctcg   9240
gagggcgaag aatctcgtgc tttcagcttc gatgtaggag ggcgtggata tgtcctgcgg   9300
gtaaatagct gcgccgatgg tttctacaaa gatcgttatg tttatcggca ctttgcatcg   9360
gccgcgctcc cgattccgga agtgcttgac attggggaat tcagcgagag cctgacctat   9420
tgcatctccc gccgtgcaca gggtgtcacg ttgcaagacc tgcctgaaac cgaactgccc   9480
gctgttctgc agccggtcgc ggaggccatg gatgcgatcg ctgcggccga tcttagccag   9540
acgagcgggt tcggcccatt cggaccgcaa ggaatcggtc aatacactac atggcgtgat   9600
ttcatatgcg cgattgctga tccccatgtg tatcactggc aaactgtgat ggacgacacc   9660
gtcagtgcgt ccgtcgcgca ggctctcgat gagctgatgc tttgggccga ggactgcccc   9720
gaagtccggc acctcgtgca cgcggatttc ggctccaaca atgtcctgac ggacaatggc   9780
cgcataacag cggtcattga ctggagcgag gcgatgttcg gggattccca atacgaggtc   9840
gccaacatct tcttctggag gccgtggttg gcttgtatgg agcagcagac gcgctacttc   9900
gagcggaggc atccggagct tgcaggatcg ccgcggctcc gggcgtatat gctccgcatt   9960
ggtcttgacc aactctatca gagcttggtt gacggcaatt cgatgatgc agcttgggcg   10020
cagggtcgat gcgacgcaat cgtccgatcc ggagccggga ctgtcgggcg tacacaaatc   10080
gccccgcagaa gcgcggccgt ctggaccgat ggctgtgtag aagtactcgc cgatagtgga   10140
aaccgacgcc ccagcactcg tccgagggga tcgggagatg ggggaggcta actgaaacac   10200
ggaaggagac aatacc                                                   10216
```

<210> SEQ ID NO 17
<211> LENGTH: 231
<212> TYPE: PRT
<213> ORGANISM: Artificial sequence
<220> FEATURE:
<223> OTHER INFORMATION: Nef fused to an export signal sequence

<400> SEQUENCE: 17

Met Glu Thr Asp Thr Leu Leu Leu Trp Val Leu Leu Leu Trp Val Pro
1               5                   10                  15

Gly Ser Thr Gly Asp Ala Ala Gln Pro Ala Gly Gly Lys Trp Ser Lys
            20                  25                  30

Ser Ser Val Val Gly Trp Pro Thr Val Arg Glu Arg Met Arg Arg Ala
        35                  40                  45

Glu Pro Ala Ala Asp Gly Val Gly Ala Ala Ser Arg Asp Leu Glu Lys
    50                  55                  60

His Gly Ala Ile Thr Ser Ser Asn Thr Ala Thr Asn Ala Ala Cys
65                  70                  75                  80

Ala Trp Leu Glu Ala Gln Glu Glu Glu Val Gly Phe Pro Val Thr
            85                  90                  95

Pro Gln Val Pro Leu Arg Pro Met Thr Tyr Lys Ala Ala Val Asp Leu
            100                 105                 110

Ser His Phe Leu Lys Glu Lys Gly Leu Glu Gly Leu Ile His Ser
        115                 120                 125

Gln Arg Arg Gln Asp Ile Leu Asp Leu Trp Ile Tyr His Thr Gln Gly
130                 135                 140

Tyr Phe Pro Asp Trp Gln Asn Tyr Thr Pro Gly Pro Gly Val Arg Tyr
145                 150                 155                 160

Pro Leu Thr Phe Gly Trp Cys Tyr Lys Leu Val Pro Val Glu Pro Asp
                165                 170                 175

Lys Val Glu Glu Ala Asn Lys Gly Glu Asn Thr Ser Leu Leu His Pro
            180                 185                 190

Val Ser Leu His Gly Met Asp Asp Pro Glu Arg Glu Val Leu Glu Trp
        195                 200                 205

Arg Phe Asp Ser Arg Leu Ala Phe His His Val Ala Arg Glu Leu His
    210                 215                 220

Pro Glu Tyr Phe Lys Asn Cys
225                 230

<210> SEQ ID NO 18
<211> LENGTH: 10216
<212> TYPE: DNA
<213> ORGANISM: Artificial sequence
<220> FEATURE:
<223> OTHER INFORMATION: pDFG-expNefE93R vector expressing the E93R Nef
      mutant fused to an export signal sequence

<400> SEQUENCE: 18
ggatccgcgg gattagtcca atttgttaaa gacaggatat cagtggtcca ggctctagtt      60
ttgactcaac aatatcacca gctgaagcct atagagtacg agccatagat aaaataaaag    120
attttattta gtctccagaa aaggggggga atgaaagacc ccacctgtag gtttggcaag    180
ctagcttaag taacgccatt ttgcaaggca tggaaaaata cataactgag aatagagaag    240
ttcagatcaa ggtcaggaac agatggaaca gctgaatatg gccaaacag gatatctgtg    300 gtaagcagtt cctgccccgg ctcagggcca agaacagatg aacagctga atgggcca    360 aacaggatat ctgtggtaag cagttcctgc cccggctcag ggccaagaac agatggtccc    420
cagatgcggt ccagccctca gcagtttcta gagaaccatc agatgtttcc agggtgcccc    480
aaggacctga atgaccctg tgccttattt gaactaacca atcagttcgc ttctcgcttc    540
tgttcgcgcg cttctgctcc ccgagctcaa taaagagcc cacaacccct cactcggggc    600
gccagtcctc cgattgactg agtcgcccgg gtacccgtgt atccaataaa ccctcttgca    660
gttgcatccg acttgtggtc tcgctgttcc ttgggagggt ctcctctgag tgattgacta    720
cccgtcagcg ggggtctttc acatgcagca tgtatcaaaa ttaatttggt ttttttcttt    780
aagtatttac attaaatggc catagtactt aagttacat ggcttccctt gaaataaaca    840
tggagtattc agaatgtgtc ataaatattt ctaattttaa gatagtatct ccattggctt    900 tctactttt cttttatttt ttttgtcct ctgtcttcca tttgttgttg ttgttgttttg    960 tttgtttgtt tgttggttgg ttggttaatt ttttttttaaa gatcctacac tatagttcaa    1020
gctagactat tagctactct gtaacccagg gtgaccttga agtcatgggt agcctgctgt    1080
tttagccttc ccacatctaa gattacaggt atgagctatc attttggta tattgattga    1140 ttgattgatt gatgtgtgtg tgtgtgattg tgtttgtgtg tgtgattgtg tatatgtgtg    1200

```
tatggttgtg tgtgattgtg tgtatgtatg tttgtgtgtg attgtgtgtg tgtgattgtg   1260
catgtgtgtg tgtgtgattg tgtttatgtg tatgattgtg tgtgtgtgtg tgtgtgtgtg   1320
tgtgtgtgtg tgtgtgtgtg tgttgtgtat atatatttat ggtagtgaga ggcaacgctc   1380
cggctcaggt gtcaggttgg tttttgagac agagtctttc acttagcttg gaattcttga   1440
agacgaaagg gcctcgtgat acgcctattt ttataggtta atgtcatgat aataatggtt   1500
tcttagacgt caggtggcac ttttcgggga aatgtgcgcg gaaccccctat ttgtttattt   1560
ttctaaatac attcaaatat gtatccgctc atgagacaat aaccctgata aatgcttcaa   1620
taatattgaa aaaggaagag tatgagtatt caacatttcc gtgtcgccct tattcccttt   1680
tttgcggcat tttgccttcc tgttttttgct cacccagaaa cgctggtgaa agtaaaagat   1740
gctgaagatc agttgggtgc acgagtgggt tacatcgaac tggatctcaa cagcggtaag   1800
atccttgaga gttttcgccc cgaagaacgt tttccaatga tgagcacttt taaagttctg   1860
ctatgtggcg cggtattatc ccgtgttgac gccgggcaac agcaactcgg tcgccgcata   1920
cactattctc agaatgactt ggttgagtac tcaccagtca cagaaaagca tcttacggat   1980
ggcatgacag taagagaatt atgcagtgct gccataacca tgagtgataa cactgcggcc   2040
aacttacttc tgacaacgat cggaggaccg aaggagctaa ccgcttttttt gcacaacatg   2100
ggggatcatg taactcgcct tgatcgttgg gaaccggagc tgaatgaagc cataccaaac   2160
gacgagcgtg acaccacgat gcctgcagca atggcaacaa cgttgcgcaa actattaact   2220
ggcgaactac ttactctagc ttcccggcaa caattaatag actggatgga ggcggataaa   2280
gttgcaggac cacttctgcg ctcggccctt ccggctggct ggtttattgc tgataaatct   2340
ggagccggtg agcgtgggtc tcgcggtatc attgcagcac tggggccaga tggtaagccc   2400
tcccgtatcg tagttatcta cacgacgggg agtcaggcaa ctatggatga acgaaataga   2460
cagatcgctg agataggtgc ctcactgatt aagcattggt aactgtcaga ccaagtttac   2520
tcatatatac tttagattga tttaaaactt catttttaat ttaaaaggat ctaggtgaag   2580
atcctttttg ataatctcat gaccaaaatc ccttaacgtg agttttcgtt ccactgagcg   2640
tcagacccccg tagaaaagat caaaggatct cttgagatc ctttttttct gcgcgtaatc   2700
tgctgcttgc aaacaaaaaa accaccgcta ccagcggtgg tttgtttgcc ggatcaagag   2760
ctaccaactc tttttccgaa ggtaactggc ttcagcagag cgcagatacc aaatactgtc   2820
cttctagtgt agccgtagtt aggccaccac ttcaagaact ctgtagcacc gcctacatac   2880
ctcgctctgc taatcctgtt accagtggct gctgccagtg gcgataagtc gtgtcttacc   2940
gggttggact caagacgata gttaccggat aaggcgcagc ggtcgggctg aacggggggt   3000
tcgtgcacac agcccagctt ggagcgaacg acctacaccg aactgagata cctacagcgt   3060
gagctatgag aaagcgccac gcttcccgaa gggagaaagg cggacaggta tccggtaagc   3120
ggcagggtcg gaacaggaga gcgcacgagg gagcttccag ggggaaacgc ctggtatctt   3180
tatagtcctg tcgggtttcg ccacctctga cttgagcgtc gatttttgtg atgctcgtca   3240
ggggggcgga gcctatggaa aaacgccagc aacgcggcct ttttacggtt cctggccttt   3300
tgctggcctt ttgctcacat gttctttcct gcgttatccc ctgattctgt ggataaccgt   3360
attaccgcct ttgagtgagc tgataccgct cgccgcagcc gaacgaccga gcgcagcgag   3420
tcagtgagcg aggaagcgga agagcgcctg atgcggtatt ttctccttac gcatctgtgc   3480
ggtatttcac accgcatata tggtgcactc tcagtacaat ctgctctgat gccgcatagt   3540
taagccagta tacactccgc tatcgctacg tgactgggtc atggctgcgc cccgacaccc   3600
```

```
gccaacaccc gctgacgcgc cctgacgggc ttgtctgctc ccggcatccg cttacagaca    3660
agctgtgacc gtctccggga gctgcatgtg tcagaggttt tcaccgtcat caccgaaacg    3720
cgcgaggcag ctgcggtaaa gctcatcagc gtggtcgtga agcgattcac agatgtctgc    3780
ctgttcatcc gcgtccagct cgttgagttt ctccagaagc gttaatgtct ggcttctgat    3840
aaagcgggcc atgttaaggg cggttttttc ctgtttggtc acttgatgcc tccgtgtaag    3900
ggggaatttc tgttcatggg ggtaatgata ccgatgaaac gagagaggat gctcacgata    3960
cgggttactg atgatgaaca tgcccggtta ctggaacgtt gtgagggtaa caactggcg     4020 gtatggatgc ggcgggacca gagaaaaatc actcagggtc aatgccagcg cttcgttaat    4080
acagatgtag gtgttccaca gggtagccag cagcatcctg cgatgcagat ccggaacata    4140
atggtgcagg cgctgactt ccgcgtttcc agactttacg aaacacggaa accgaagacc     4200
attcatgttg ttgctcaggt cgcagacgtt ttgcagcagc agtcgcttca cgttcgctcg    4260
cgtatcggtg attcattctg ctaaccagta aggcaacccc gccagcctag ccgggtcctc    4320
aacgacagga gcacgatcat gcgcacccgt ggccaggacc caacgctgcc cgagatgcgc    4380
cgcgtgcggc tgctggagat ggcggacgcg atggatatgt tctgccaagg gttggtttgc    4440
gcattcacag ttctccgcaa gaattgattg gctccaattc ttggagtggt gaatccgtta    4500
gcgaggtgcc gccggcttcc attcaggtcg aggtggcccg gctccatgca ccgcgacgca    4560
acgcggggag gcagacaagg tatagggcgg cgcctacaat ccatgccaac ccgttccatg    4620
tgctcgccga ggcggcataa atcgccgtga cgatcagcgg tccagtgatc gaagttaggc    4680
tggtaagagc cgcgagcgat ccttgaagct gtccctgatg gtcgtcatct acctgcctgg    4740
acagcatggc ctgcaacgcg ggcatcccga tgccgccgga agcgagaaga atcataatgg    4800
ggaaggccat ccagcctcgc gtcgcgaacg ccagcaagac gtagcccagc gcgtcggccg    4860
ccatgccggc gataatggcc tgcttctcgc cgaaacgttt ggtggcggga ccagtgacga    4920
aggcttgagc gagggcgtgc aagattccga ataccgcaag cgacaggccg atcatcgtcg    4980
cgctccagcg aaagcggtcc tcgccgaaaa tgacccagag cgctgccggc acctgtccta    5040
cgagttgcat gataaagaag acagtcataa gtgcggcgac gatagtcatg ccccgcgccc    5100
accggaagga gctgactggg ttgaaggctc tcaagggcat cggtcgacgc tctcccttat    5160
gcgactcctg cattaggaag cagcccagta gtaggttgag gccgttgagc accgccgccg    5220
caaggaatgg tgcatgcaag gagatggcgc ccaacagtcc cccggccacg gggcctgcca    5280
ccatacccac gccgaaacaa gcgctcatga gcccgaagtg gcgagcccga tcttccccat    5340
cggtgatgtc ggcgatatag gcgccagcaa ccgcacctgt ggcgccggtg atgccggcca    5400
cgatgcgtcc ggcgtagagg atcgatccac aggacgggtg tggtcgccat gatcgcgtag    5460
tcgatagtgg ctccaagtag cgaagcgagc aggactgggc ggcggccaaa gcggtcggac    5520
agtgctccga gaacgggtgc gcatagaaat tgcatcaacg catatagcgc tagcagcacg    5580
ccatagtgac tggcgatgct gtcggaatgg acgatatccc gcaagaggcc cggcagtacc    5640
ggcataacca agcctatgcc tacagcatcc agggtgacgg tgccgaggat gacgatgagc    5700
gcattgttag atttcataca cggtgcctga ctgcgttagc aatttaactg tgataaacta    5760
ccgcattaaa gctttgctct taggagtttc ctaatacatc ccaaactcaa atatataaag    5820
catttgactt gttctatgcc ctaggggcg ggggaagct aagccagctt ttttaacat       5880 ttaaaatgtt aattccattt taaatgcaca gatgttttta tttcataagg gtttcaatgt    5940
```

-continued

```
gcatgaatgc tgcaatattc ctgttaccaa agctagtata aataaaaata gataaacgtg    6000
gaaattactt agagtttctg tcattaacgt ttccttcctc agttgacaac ataaatgcgc    6060
tgctgagaag ccagtttgca tctgtcagga tcaatttccc attatgccag tcatattaat    6120
tactagtcaa ttagttgatt tttatttttg acatatacat gtgaaagacc ccacctgtag    6180
gtttggcaag ctagcttaag taacgccatt ttgcaaggca tggaaaaata cataactgag    6240
agggccaaac aggatatctg tggtaagcag ttcatagaaa agttcagatc aaggtcagga    6300
acagatggaa cagctgaata tctgccccgg ctcagggcca agaacagatg aacagctga    6360 atatgggcca acaggatat ctgtggtaag cagttcctgc cccggctcag ggccaagaac    6420
agatggtccc cagatgcggt ccagccctca gcagtttcta gagaaccatc agatgtttcc    6480
agggtgcccc aaggacctga aatgaccctg tgccttattt gaactaacca atcagttcgc    6540
ttctcgcttc tgttcgcgcg cttctgctcc ccgagctcaa taaaagagcc cacaacccct    6600
cactcggcgc gccagtcctc cgattgacta gtcgcccgg gtacccgtgt atccaataaa    6660
ccctcttgca gttgcatccg acttgtggtc tcgctgttcc ttgggagggt ctcctctgag    6720
tgattgacta cccgtcagcg ggggtctttc atttgggggc tcgtccggga tcgggagacc    6780
cctgcccagg gaccaccgac ccaccaccgg gaggtaagct ggccagcaac ttatctgtgt    6840
ctgtccgatt gtctagtgtc tatgactgat tttatgcgcc tgcgtcggta ctagttagct    6900
aactagctct gtatctggcg gacccgtggt ggaactgacg agttcggaac cccggccgc    6960 aaccctggga gacgtcccag ggacttcggg ggccgttttt gtggcccgac ctgagtccaa    7020
aaatcccgat cgttttggac tctttggtgc acccccctta gaggagggat atgtggttct    7080
ggtaggagac gagaacctaa aacagttccc gcctccgtct gaattttgc tttcggtttg    7140 ggaccgaagc cgcgccgcgc gtcttgtctg ctgcagcatc gttctgtgtt gtctctgtct    7200
gactgtgttt ctgtatttgt ctgaaaatat gggcccgccg cggcgggcca gactgttacc    7260
actcccttaa gtttgacctt aggtcactgg aaagatgtcg agcggatcgc tcacaaccag    7320
tcggtagatg tcaagaagag acgttgggtt accttctgct ctgcagaatg ccaacctttt    7380
aacgtcggat ggccgcgaga cggcaccttt aaccgagacc tcatcaccca ggttaagatc    7440
aaggtctttt cacctggccc gcatggacac ccagaccagg tcccctacat cgtgacctgg    7500
gaagccttgg ctttttgaccc ccctccctgg gtcaagccct ttgtacaccc taagcctccg    7560
cctcctcttc ctccatccgc cccgtctctc cccctttgaac ctcctcgttc gaccccgcct    7620
cgatcctccc tttatccagc cctcactcct tctctaggcg ccccccatatg gccatatgag    7680 atcttatatg gggcacccc gcccccttgta aacttccctg accctgacat gacaagagtt    7740
actaacagcc cctctctcca agctcactta caggctctct acttagtcca gcacgaagtc    7800
tggagacctc tggcggcagc ctaccaagaa caactggacc gaccggtatg gagacagaca    7860
cactcctgct atgggtactg ctgctctggg ttccaggttc cactggtgac gcggcccagc    7920
cggccggtgg caagtggtca aaagtagtg tggttggatg gcctactgta agggaaagaa    7980
tgagacgagc tgagccagca gcagatgggg tgggagcagc atctcgagac ctggaaaaac    8040
atggagcaat cacaagtagc aatacagcag ctaccaatgc tgcttgtgcc tggctagaag    8100
cacaagagga ggaggaggtg ggttttccag tcacacctca ggtacctta agaccaatga    8160 cttacaaggc agctgtagat cttagccact ttcttaagcg aaaggggggga ctggaagggc    8220 taattcactc ccaacgaaga caagatatcc ttgatctgtg gatctaccac acacaaggct    8280
acttccctga ttggcagaac tacacaccag ggccaggggt cagatatcca ctgacctttg    8340
```

```
gatggtgcta caagctagta ccagttgagc cagataaggt agaagaggcc aataaaggag    8400
agaacaccag cttgttacac cctgtgagcc tgcatggaat ggatgaccct gagagagaag    8460
tgttagagtg gaggtttgac agccgcctag catttcatca cgtggcccga gagctgcatc    8520
cggagtactt caagaactgc tgaacgcgtt gactcgagaa ttccggcccc tctccctccc    8580
ccccccctaa cgttactggc cgaagccgct tggaataagg ccggtgtgcg tttgtctata    8640
tgttattttc caccatattg ccgtcttttg gcaatgtgag ggcccggaaa cctgccctg     8700
tcttcttgac gagcattcct aggggtcttt ccctctcgc caaaggaatg caaggtctgt     8760
tgaatgtcgt gaaggaagca gttcctctgg aagcttcttg aagacaaaca acgtctgtag    8820
cgacccttg caggcagcgg aaccccccac ctggcgacag gtgcctctgc ggccaaaagc     8880
cacgtgtata agatacacct gcaaaggcgg cacaacccca gtgccacgtt gtgagttgga    8940
tagttgtgga aagagtcaaa tggctctcct caagcgtatt caacaagggg ctgaaggatg    9000
cccagaaggt accccattgt atgggatctg atctggggcc tcggtgcaca tgctttacat    9060
gtgtttagtc gaggttaaaa aacgtctagg cccccgaac cacggggacg tggttttcct     9120
ttgaaaaaca cgatgataat atggccacaa ccatggaaaa agcctgaact caccgcgacg    9180
tctgtcgaga gtttctgat cgaaaagttc gacagcgtct ccgacctgat gcagctctcg     9240
gagggcgaag aatctcgtgc tttcagcttc gatgtaggag ggcgtggata tgtcctgcgg    9300
gtaaatagct gcgccgatgg tttctacaaa gatcgttatg tttatcggca ctttgcatcg    9360
gccgcgctcc cgattccgga agtgcttgac attggggaat tcagcgagag cctgacctat    9420
tgcatctccc gccgtgcaca gggtgtcacg ttgcaagacc tgcctgaaac cgaactgccc    9480
gctgttctgc agccggtcgc ggaggccatg gatgcgatcg ctgcggccga tcttagccag    9540
acgagcgggt tcggcccatt cggaccgcaa ggaatcggtc aatacactac atggcgtgat    9600
ttcatatgcg cgattgctga tccccatgtg tatcactggc aaactgtgat ggacgacacc    9660
gtcagtgcgt ccgtcgcgca ggctctcgat gagctgatgc tttgggccga ggactgcccc    9720
gaagtccggc acctcgtgca cgcggatttc ggctccaaca atgtcctgac ggacaatggc    9780
cgcataacag cggtcattga ctggagcgag gcgatgttcg gggattccca atacgaggtc    9840
gccaacatct tcttctggag gccgtggttg gcttgtatgg agcagcagac gcgctacttc    9900
gagcggaggc atccggagct tgcaggatcg ccgcggctcc gggcgtatat gctccgcatt    9960
ggtcttgacc aactctatca gagcttggtt gacggcaatt tcgatgatgc agcttgggcg    10020
cagggtcgat gcgacgcaat cgtccgatcc ggagccggga ctgtcgggcg tacacaaatc    10080
gcccgcagaa gcgcggccgt ctggaccgat ggctgtgtag aagtactcgc cgatagtgga    10140
aaccgacgcc ccagcactcg tccgagggga tcggagatg ggggaggcta actgaaacac     10200
ggaaggagac aatacc                                                    10216
```

<210> SEQ ID NO 19
<211> LENGTH: 231
<212> TYPE: PRT
<213> ORGANISM: Artificial sequence
<220> FEATURE:
<223> OTHER INFORMATION: E93R Nef mutant fused to an export signal
      sequence

<400> SEQUENCE: 19

Met Glu Thr Asp Thr Leu Leu Leu Trp Val Leu Leu Leu Trp Val Pro
1               5                   10                  15

Gly Ser Thr Gly Asp Ala Ala Gln Pro Ala Gly Lys Trp Ser Lys
            20                  25                  30

Ser Ser Val Val Gly Trp Pro Thr Val Arg Glu Arg Met Arg Ala
        35                  40                  45

Glu Pro Ala Ala Asp Gly Val Gly Ala Ala Ser Arg Asp Leu Glu Lys
 50                  55                  60

His Gly Ala Ile Thr Ser Ser Asn Thr Ala Thr Asn Ala Ala Cys
 65              70                  75                  80

Ala Trp Leu Glu Ala Gln Glu Glu Glu Val Gly Phe Pro Val Thr
                85                  90                  95

Pro Gln Val Pro Leu Arg Pro Met Thr Tyr Lys Ala Ala Val Asp Leu
        100                 105                 110

Ser His Phe Leu Lys Arg Lys Gly Gly Leu Glu Gly Leu Ile His Ser
        115                 120                 125

Gln Arg Arg Gln Asp Ile Leu Asp Leu Trp Ile Tyr His Thr Gln Gly
130                 135                 140

Tyr Phe Pro Asp Trp Gln Asn Tyr Thr Pro Gly Pro Gly Val Arg Tyr
145                 150                 155                 160

Pro Leu Thr Phe Gly Trp Cys Tyr Lys Leu Val Pro Val Glu Pro Asp
                165                 170                 175

Lys Val Glu Glu Ala Asn Lys Gly Glu Asn Thr Ser Leu Leu His Pro
        180                 185                 190

Val Ser Leu His Gly Met Asp Asp Pro Glu Arg Glu Val Leu Glu Trp
        195                 200                 205

Arg Phe Asp Ser Arg Leu Ala Phe His His Val Ala Arg Glu Leu His
210                 215                 220

Pro Glu Tyr Phe Lys Asn Cys
225                 230

<210> SEQ ID NO 20
<211> LENGTH: 5443
<212> TYPE: DNA
<213> ORGANISM: Artificial sequence
<220> FEATURE:
<223> OTHER INFORMATION: phCMV-Nef vector expressing Nef

<400> SEQUENCE: 20
gcggccgctc tagagagctt ggcccattgc atacgttgta tccatatcat aatatgtaca      60
tttatattgg ctcatgtcca acattaccgc catgttgaca ttgattattg actagttatt     120
aatagtaatc aattacgggg tcattagttc atagcccata tatggagttc cgcgttacat     180
aacttacggt aaatggcccg cctggctgac cgcccaacga cccccgccca ttgacgtcaa     240
taatgacgta tgttcccata gtaacgccaa tagggacttt ccattgacgt caatgggtgg     300
agtatttacg gtaaactgcc cacttggcag tacatcaagt gtatcatatg ccaagtacgc     360
cccctattga cgtcaatgac ggtaaatggc ccgcctggca ttatgcccag tacatgacct     420
tatgggactt tcctacttgg cagtacatct acgtattagt catcgctatt accatggtga     480
tgcggttttg gcagtacatc aatgggcgtg gatagcggtt tgactcacgg ggatttccaa     540
gtctccaccc cattgacgtc aatgggagtt tgttttggca ccaaaatcaa cgggactttc     600
caaaatgtcg taacaactcc gccccattga cgcaaatggg cggtaggcgt gtacggtggg     660
aggtctatat aagcagagct cgtttagtga accgtcagat cgcctggaga cgccatccac     720
gctgttttga cctccataga agacaccggg accgatccag cctccggtcg accgatcctg     780
agaacttcag ggtgagtttg ggacccttga ttgttctttc tttttcgct attgtaaaat     840

-continued

```
tcatgttata tggaggggc aaagttttca gggtgttgtt tagaatggga agatgtccct      900
tgtatcacca tggaccctca tgataatttt gtttctttca ctttctactc tgttgacaac      960
cattgtctcc tcttattttc ttttcatttt ctgtaactt ttcgttaaac tttagcttgc     1020
atttgtaacg aattttaaa ttcactttg tttatttgtc agattgtaag tactttctct     1080
aatcactttt ttttcaaggc aatcagggta tattatattg tacttcagca cagttttaga     1140
gaacaattgt tataattaaa tgataaggta gaatatttct gcatataaat ctggctggc      1200
gtggaaatat tcttattggt agaaacaact acaccctggt catcatcctg cctttctctt     1260
tatggttaca atgatataca ctgtttgaga tgaggataaa atactctgag tccaaaccgg     1320
gcccctctgc taaccatgtt catgccttct tctctttcct acagctcctg gcaacgtgc      1380
tggttgttgt gctgtctcat cattttggca aagaattcct cgacggatcc ctcgacccaa     1440
ctagaaccat gggtggcaag tggtcaaaaa gtagtgtggt tggatggcct actgtaaggg     1500
aaagaatgag acgagctgag ccagcagcag atggggtggg agcagcatct cgagacctgg     1560
aaaaacatgg agcaatcaca agtagcaata cagcagctac caatgctgct tgtgcctggc     1620
tagaagcaca agaggaggag gaggtgggtt ttccagtcac acctcaggta cctttaagac     1680
caatgactta caaggcagct gtagatctta gccactttct taaggaaaag gggggactgg     1740
aagggctaat tcactcccaa cgaagacaag atatccttga tctgtggatc taccacacac     1800
aaggctactt ccctgattgg cagaactaca caccagggcc aggggtcaga tatccactga     1860
cctttggatg gtgctacaag ctagtaccag ttgagccaga taaggtagaa gaggccaata     1920
aaggagagaa caccagcttg ttacaccctg tgagcctgca tggaatggat gaccctgaga     1980
gagaagtgtt agagtggagg tttgacagcc gcctagcatt tcatcacgtg gcccgagagc     2040
tgcatccgga gtacttcaag aactgctgaa cgcgtcaggt gcaggctgcc tatcagaagg     2100
tggtggctgg tgtggccaat gccctggctc acaaatacca ctgagatctt tttccctctg     2160
ccaaaaatta tggggacatc atgaagcccc ttgagcatct gacttctggc taataaagga     2220
aatttatttt cattgcaata gtgtgttgga atttttgtg tctctcactc ggaaggacat     2280
atgggagggc aaatcattta aaacatcaga atgagtattt ggtttagagt ttggcaacat     2340
atgcccatat gctggctgcc atgaacaaag gttggctata agaggtcat cagtatatga     2400
aacagccccc tgctgtccat tccttattcc atagaaaagc cttgacttga ggttagattt     2460
tttttatatt ttgttttgtg ttatttttt ctttaacatc cctaaaattt tccttacatg     2520
ttttactagc cagattttc ctcctctcct gactactccc agtcatagct gtccctcttc     2580
tcttatggag atccctcgac ggatcggccg caattcgtaa tcatgtcata gctgtttcct     2640
gtgtgaaatt gttatccgct cacaattcca cacaacatac gagccggaag cataaagtgt     2700
aaagcctggg gtgcctaatg agtgagctaa ctcacattaa ttgcgttgcg ctcactgccc     2760
gctttccagt cggaaaacct gtcgtgccag ctgcattaat gaatcggcca acgcgcgggg     2820
agaggcggtt tgcgtattgg gcgctcttcc gcttcctcgc tcactgactc gctgcgctcg     2880
gtcgttcggc tgcggcgagc ggtatcagct cactcaaagg cggtaatacg gttatccaca     2940
gaatcagggg ataacgcagg aaagaacatg tgagcaaaag gccagcaaaa ggccaggaac     3000
cgtaaaaagg ccgcgttgct ggcgtttttc cataggctcc gcccccctga cgagcatcac     3060
aaaaatcgac gctcaagtca gaggtggcga aacccgacag gactataaag ataccaggcg     3120
tttccccctg gaagctccct cgtgcgctct cctgttccga ccctgccgct taccggatac     3180
```

```
ctgtccgcct ttctcccttc gggaagcgtg gcgctttctc atagctcacg ctgtaggtat    3240
ctcagttcgg tgtaggtcgt tcgctccaag ctgggctgtg tgcacgaacc ccccgttcag    3300
cccgaccgct gcgccttatc cggtaactat cgtcttgagt ccaacccggt aagacacgac    3360
ttatcgccac tggcagcagc cactggtaac aggattagca gagcgaggta tgtaggcggt    3420
gctacagagt tcttgaagtg gtggcctaac tacggctaca ctagaagaac agtatttggt    3480
atctgcgctc tgctgaagcc agttaccttc ggaaaaagag ttggtagctc ttgatccggc    3540
aaacaaacca ccgctggtag cggtggtttt tttgtttgca agcagcagat tacgcgcaga    3600
aaaaaaggat ctcaagaaga tcctttgatc ttttctacgg ggtctgacgc tcagtggaac    3660
gaaaactcac gttaagggat tttggtcatg agattatcaa aaaggatctt cacctagatc    3720
cttttaaatt aaaaatgaag ttttaaatca atctaaagta tatatgagta aacttggtct    3780
gacagttacc aatgcttaat cagtgaggca cctatctcag cgatctgtct atttcgttca    3840
tccatagttg cctgactccc cgtcgtgtag ataactacga tacggagggc ttaccatct    3900
ggccccagtg ctgcaatgat accgcgagac ccacgctcac cggctccaga tttatcagca    3960
ataaaccagc cagccggaag ggccgagcgc agaagtggtc ctgcaacttt atccgcctcc    4020
atccagtcta ttaattgttg ccgggaagct agagtaagta gttcgccagt taatagtttg    4080
cgcaacgttg ttgccattgc tacaggcatc gtggtgtcac gctcgtcgtt tggtatggct    4140
tcattcagct ccggttccca acgatcaagg cgagttacat gatccccat gttgtgcaaa    4200
aaagcgggtt agctccttcg gtcctccgat cgttgtcaga agtaagttgg ccgcagtgtt    4260
atcactcatg gttatggcag cactgcataa ttctcttact gtcatgccat ccgtaagatg    4320
cttttctgtg actggtgagt actcaaccaa gtcattctga aatagtgta tgcggcgacc    4380
gagttgctct tgcccggcgt caatacggga taataccgcg ccacatagca gaactttaaa    4440
agtgctcatc attggaaaac gttcttcggg gcgaaaactc tcaaggatct taccgctgtt    4500
gagatccagt tcgatgtaac ccactcgtgc acccaactga tcttcagcat cttttacttt    4560
caccagcgtt tctgggtgag caaaaacagg aaggcaaaat gccgcaaaaa agggaataag    4620
ggcgacacgg aaatgttgaa tactcatact cttcctttt caatattatt gaagcattta    4680
tcagggttat tgtctcatga gcggatacat atttgaatgt atttagaaaa ataaacaaat    4740
aggggttccg cgcacatttc cccgaaaagt gccacctaaa ttgtaagcgt taatattttg    4800
ttaaaattcg cgttaaattt ttgttaaatc agctcatttt ttaaccaata ggccgaaatc    4860
ggcaaaatcc cttataaatc aaaagaatag accgagatag ggttgagtgt tgttccagtt    4920
tggaacaaga gtccactatt aaagaacgtg gactccaacg tcaaagggcg aaaaaccgtc    4980
tatcagggcg atggcccact acgtgaacca tcaccctaat caagttttt ggggtcgagg    5040
tgccgtaaag cactaaatcg gaaccctaaa gggagccccc gatttagagc ttgacgggga    5100
aagccggcga acgtggcgag aaaggaaggg aagaaagcga aaggagcggg cgctagggcg    5160
ctggcaagtg tagcggtcac gctgcgcgta accaccacac ccgccgcgct taatgcgccg    5220
ctacagggcg cgtcccattc gccattcagg ctgcgcaact gttgggaagg gcgatcggtg    5280
cgggcctctt cgctattacg ccagctggcg aaagggggat gtgctgcaag gcgattaagt    5340
tgggtaacgc cagggttttc ccagtcacga cgttgtaaaa cgacggccag tgagcgcgcg    5400
taatacgact cactataggg cgaattggag ctccaccgcg gtg                      5443
```

<210> SEQ ID NO 21
<211> LENGTH: 5443

<212> TYPE: DNA
<213> ORGANISM: Artificial sequence
<220> FEATURE:
<223> OTHER INFORMATION: phCMV-NefE93R vector expressing the E93R Nef
      mutant

<400> SEQUENCE: 21

| | | | | | |
|---|---|---|---|---|---|
| gcggccgctc | tagagagctt | ggcccattgc | atacgttgta | tccatatcat | aatatgtaca | 60 |
| tttatattgg | ctcatgtcca | acattaccgc | catgttgaca | ttgattattg | actagttatt | 120 |
| aatagtaatc | aattacgggg | tcattagttc | atagcccata | tatggagttc | cgcgttacat | 180 |
| aacttacggt | aaatggcccg | cctggctgac | cgcccaacga | cccccgccca | ttgacgtcaa | 240 |
| taatgacgta | tgttcccata | gtaacgccaa | tagggacttt | ccattgacgt | caatgggtgg | 300 |
| agtatttacg | gtaaactgcc | cacttggcag | tacatcaagt | gtatcatatg | ccaagtacgc | 360 |
| cccctattga | cgtcaatgac | ggtaaatggc | ccgcctggca | ttatgcccag | tacatgacct | 420 |
| tatgggactt | tcctacttgg | cagtacatct | acgtattagt | catcgctatt | accatggtga | 480 |
| tgcggttttg | gcagtacatc | aatgggcgtg | gatagcggtt | tgactcacgg | ggatttccaa | 540 |
| gtctccaccc | cattgacgtc | aatgggagtt | tgttttggca | ccaaaatcaa | cgggactttc | 600 |
| caaaatgtcg | taacaactcc | gccccattga | cgcaaatggg | cggtaggcgt | gtacggtggg | 660 |
| aggtctatat | aagcagagct | cgtttagtga | accgtcagat | cgcctggaga | cgccatccac | 720 |
| gctgttttga | cctccataga | agacaccggg | accgatccag | cctccggtcg | accgatcctg | 780 |
| agaacttcag | ggtgagtttg | ggacccttg | attgttcttt | cttttcgct | attgtaaaat | 840 |
| tcatgttata | tggaggggc | aaagttttca | gggtgttgtt | tagaatggga | agatgtccct | 900 |
| tgtatcacca | tggaccctca | tgataatttt | gtttctttca | ctttctactc | tgttgacaac | 960 |
| cattgtctcc | tcttattttc | ttttcatttt | ctgtaacttt | ttcgttaaac | tttagcttgc | 1020 |
| atttgtaacg | aatttttaaa | ttcacttttg | tttatttgtc | agattgtaag | tactttctct | 1080 |
| aatcacttt | ttttcaaggc | aatcagggta | tattatattg | tacttcagca | cagttttaga | 1140 |
| gaacaattgt | tataattaaa | tgataaggta | gaatatttct | gcatataaat | tctggctggc | 1200 |
| gtggaaatat | tcttattggt | agaaacaact | acaccctggt | catcatcctg | cctttctctt | 1260 |
| tatggttaca | atgatataca | ctgtttgaga | tgaggataaa | atactctgag | tccaaaccgg | 1320 |
| gcccctctgc | taaccatgtt | catgccttct | tctctttcct | acagctcctg | ggcaacgtgc | 1380 |
| tggttgttgt | gctgtctcat | catttttggca | aagaattcct | cgacggatcc | ctcgacccaa | 1440 |
| ctagaaccat | gggtggcaag | tggtcaaaaa | gtagtgtggt | tggatggcct | actgtaaggg | 1500 |
| aaagaatgag | acgagctgag | ccagcagcag | atggggtggg | agcagcatct | cgagacctgg | 1560 |
| aaaaacatgg | agcaatcaca | agtagcaata | cagcagctac | caatgctgct | tgtgcctggc | 1620 |
| tagaagcaca | agaggaggag | gaggtgggtt | ttccagtcac | acctcaggta | cctttaagac | 1680 |
| caatgactta | caaggcagct | gtagatctta | gccactttct | taagcgaaag | ggggactgg | 1740 |
| aagggctaat | tcactcccaa | cgaagacaag | atatccttga | tctgtggatc | taccacacac | 1800 |
| aaggctactt | ccctgattgg | cagaactaca | caccagggcc | aggggtcaga | tatccactga | 1860 |
| cctttggatg | gtgctacaag | ctagtaccag | ttgagccaga | taaggtagaa | gaggccaata | 1920 |
| aaggagagaa | caccagcttg | ttacaccctg | tgagcctgca | tggaatggat | gaccctgaga | 1980 |
| gagaagtgtt | agagtggagg | tttgacagcc | gcctagcatt | tcatcacgtg | gcccgagagc | 2040 |
| tgcatccgga | gtacttcaag | aactgctgaa | cgcgtcaggt | gcaggctgcc | tatcagaagg | 2100 |
| tggtggctgg | tgtggccaat | gccctggctc | acaaatacca | ctgagatctt | ttccctctg | 2160 |

```
ccaaaaatta tggggacatc atgaagcccc ttgagcatct gacttctggc taataaagga   2220
aatttatttt cattgcaata gtgtgttgga attttttgtg tctctcactc ggaaggacat   2280
atgggagggc aaatcattta aaacatcaga atgagtattt ggtttagagt ttggcaacat   2340
atgcccatat gctggctgcc atgaacaaag gttggctata agaggtcat cagtatatga    2400 aacagccccc tgctgtccat tccttattcc atagaaaagc cttgacttga ggttagattt   2460 ttttatatt ttgttttgtg ttattttttt ctttaacatc cctaaaattt tccttacatg    2520
ttttactagc cagatttttc ctcctctcct gactactccc agtcatagct gtccctcttc   2580
tcttatggag atccctcgac ggatcggccg caattcgtaa tcatgtcata gctgtttcct   2640
gtgtgaaatt gttatccgct cacaattcca cacaacatac gagccggaag cataaagtgt   2700
aaagcctggg gtgcctaatg agtgagctaa ctcacattaa ttgcgttgcg ctcactgccc   2760
gctttccagt cgggaaacct gtcgtgccag ctgcattaat gaatcggcca acgcgcgggg   2820
agaggcggtt tgcgtattgg gcgctcttcc gcttcctcgc tcactgactc gctgcgctcg   2880
gtcgttcggc tgcggcgagc ggtatcagct cactcaaagg cggtaatacg gttatccaca   2940
gaatcagggg ataacgcagg aaagaacatg tgagcaaaag gccagcaaaa ggccaggaac   3000
cgtaaaaagg ccgcgttgct ggcgtttttc cataggctcc gcccccctga cgagcatcac   3060
aaaaatcgac gctcaagtca gaggtggcga aacccgacag gactataaag ataccaggcg   3120
tttccccctg gaagctccct cgtgcgctct cctgttccga ccctgccgct taccggatac   3180
ctgtccgcct ttctcccttc gggaagcgtg gcgctttctc atagctcacg ctgtaggtat   3240
ctcagttcgg tgtaggtcgt tcgctccaag ctgggctgtg tgcacgaacc ccccgttcag   3300
cccgaccgct gcgccttatc cggtaactat cgtcttgagt ccaacccggt aagacacgac   3360
ttatcgccac tggcagcagc cactggtaac aggattagca gagcgaggta tgtaggcggt   3420
gctacagagt tcttgaagtg gtggcctaac tacggctaca ctagaagaac agtatttggt   3480
atctgcgctc tgctgaagcc agttaccttc ggaaaaagag ttggtagctc ttgatccggc   3540
aaacaaacca ccgctggtag cggtggtttt tttgtttgca agcagcagat tacgcgcaga   3600
aaaaaaggat ctcaagaaga tcctttgatc ttttctacgg ggtctgacgc tcagtggaac   3660
gaaaactcac gttaagggat tttggtcatg agattatcaa aaaggatctt cacctagatc   3720
cttttaaatt aaaaatgaag ttttaaatca atctaaagta tatatgagta aacttggtct   3780
gacagttacc aatgcttaat cagtgaggca cctatctcag cgatctgtct atttcgttca   3840
tccatagttg cctgactccc cgtcgtgtag ataactacga tacgggaggg cttaccatct   3900
ggccccagtg ctgcaatgat accgcgagac ccacgctcac cggctccaga tttatcagca   3960 ataaccagc cagccggaag ggccgagcgc agaagtggtc ctgcaacttt atccgcctcc    4020
atccagtcta ttaattgttg ccgggaagct agagtaagta gttcgccagt taatagtttg   4080
cgcaacgttg ttgccattgc tacaggcatc gtggtgtcac gctcgtcgtt tggtatggct   4140
tcattcagct ccggttccca acgatcaagg cgagttacat gatcccccat gttgtgcaaa   4200
aaagcgggtt agctccttcg gtcctccgat cgttgtcaga agtaagttgg ccgcagtgtt   4260
atcactcatg gttatggcag cactgcataa ttctcttact gtcatgccat ccgtaagatg   4320
cttttctgtg actggtgagt actcaaccaa gtcattctga gaatagtgta tgcggcgacc   4380
gagttgctct tgcccggcgt caatacggga taataccgcg ccacatagca gaactttaaa   4440
agtgctcatc attggaaaac gttcttcggg gcgaaaactc tcaaggatct taccgctgtt   4500
```

-continued

```
gagatccagt tcgatgtaac ccactcgtgc acccaactga tcttcagcat cttttacttt      4560
caccagcgtt tctgggtgag caaaaacagg aaggcaaaat gccgcaaaaa agggaataag      4620
ggcgacacgg aaatgttgaa tactcatact cttccttttt caatattatt gaagcattta      4680
tcagggttat tgtctcatga gcggatacat atttgaatgt atttagaaaa ataaacaaat      4740
aggggttccg cgcacatttc cccgaaaagt gccacctaaa ttgtaagcgt taatattttg      4800
ttaaaattcg cgttaaattt ttgttaaatc agctcatttt ttaaccaata ggccgaaatc      4860
ggcaaaatcc cttataaatc aaaagaatag accgagatag ggttgagtgt tgttccagtt      4920
tggaacaaga gtccactatt aaagaacgtg gactccaacg tcaaagggcg aaaaaccgtc      4980
tatcagggcg atggcccact acgtgaacca tcaccctaat caagtttttt ggggtcgagg      5040
tgccgtaaag cactaaatcg aaccctaaag ggagccccc gatttagagc ttgacgggga       5100
aagccggcga acgtggcgag aaaggaaggg aagaaagcga aaggagcggg cgctagggcg      5160
ctggcaagtg tagcggtcac gctgcgcgta accaccacac ccgccgcgct taatgcgccg      5220
ctacagggcg cgtcccattc gccattcagg ctgcgcaact gttgggaagg gcgatcggtg      5280
cgggcctctt cgctattacg ccagctggcg aaagggggat gtgctgcaag gcgattaagt      5340
tgggtaacgc cagggttttc ccagtcacga cgttgtaaaa cgacggccag tgagcgcgcg      5400
taatacgact cactataggg cgaattggag ctccaccgcg gtg                        5443
```

<210> SEQ ID NO 22
<211> LENGTH: 43
<212> TYPE: DNA
<213> ORGANISM: Artificial sequence
<220> FEATURE:
<223> OTHER INFORMATION: PCR primer

<400> SEQUENCE: 22
atacatggcc cagccggccg gtggcaagtg gtcaaaaagt agt        43

<210> SEQ ID NO 23
<211> LENGTH: 39
<212> TYPE: DNA
<213> ORGANISM: Artificial sequence
<220> FEATURE:
<223> OTHER INFORMATION: PCR primer

<400> SEQUENCE: 23
atacatacgc gttcagtggc taagatctac agctgcctt        39

<210> SEQ ID NO 24
<211> LENGTH: 46
<212> TYPE: DNA
<213> ORGANISM: Artificial sequence
<220> FEATURE:
<223> OTHER INFORMATION: PCR primer

<400> SEQUENCE: 24
atacatggcc cagccggcca cttacaaggc agctgtagat cttagc        46

<210> SEQ ID NO 25
<211> LENGTH: 38
<212> TYPE: DNA
<213> ORGANISM: Artificial sequence
<220> FEATURE:
<223> OTHER INFORMATION: PCR primer

<400> SEQUENCE: 25
atacatacgt cgttcagcct tgtgtgtggt agatccac        38

<210> SEQ ID NO 26
<211> LENGTH: 46
<212> TYPE: DNA
<213> ORGANISM: Artificial sequence
<220> FEATURE:
<223> OTHER INFORMATION: PCR primer

<400> SEQUENCE: 26
atacatggcc cagccggccg atatccttga tctgtggatc taccac          46

<210> SEQ ID NO 27
<211> LENGTH: 37
<212> TYPE: DNA
<213> ORGANISM: Artificial sequence
<220> FEATURE:
<223> OTHER INFORMATION: PCR primer

<400> SEQUENCE: 27
atacataacg cgttcagcag ttcttgaagt actccgg          37

<210> SEQ ID NO 28
<211> LENGTH: 206
<212> TYPE: PRT
<213> ORGANISM: Human immunodeficiency virus type 1

<400> SEQUENCE: 28

Met Gly Gly Lys Trp Ser Lys Cys Ser Gly Gly Trp Ser Thr Ile
1               5                   10                  15

Arg Glu Arg Met Arg Arg Ala Glu Pro Ala Ala Asp Gly Val Gly Pro
            20                  25                  30

Val Ser Arg Asp Leu Glu Lys His Gly Ala Val Thr Ser Ser Asn Thr
        35                  40                  45

Ala Thr Asn Asn Ala Asp Cys Ala Trp Leu Glu Ala Gln Glu Asp Glu
    50                  55                  60

Asp Val Gly Phe Pro Val Arg Pro Gln Val Pro Leu Arg Pro Met Thr
65                  70                  75                  80

Tyr Lys Ala Ala Leu Asp Leu Ser His Phe Leu Lys Glu Lys Gly Gly
                85                  90                  95

Leu Glu Gly Leu Ile His Ser Gln Lys Arg Gln Asp Ile Leu Asp Leu
            100                 105                 110

Trp Val Tyr His Thr Gln Gly Tyr Phe Pro Ser Trp Gln Asn Tyr Thr
        115                 120                 125

Pro Gly Pro Gly Thr Arg Tyr Pro Leu Thr Tyr Gly Trp Cys Phe Lys
    130                 135                 140

Leu Leu Pro Val Glu Pro Glu Lys Val Glu Glu Ala Asn Glu Gly Glu
145                 150                 155                 160

Asn Asn Cys Leu Leu His Pro Met Ser Gln His Gly Met Glu Asp Pro
                165                 170                 175

Glu Arg Glu Val Leu Val Trp Lys Phe Asp Ser Arg Leu Ala Phe His
            180                 185                 190

His Met Ala Arg Glu Leu His Pro Glu Tyr Tyr Lys Asn Cys
        195                 200                 205

<210> SEQ ID NO 29
<211> LENGTH: 255
<212> TYPE: PRT
<213> ORGANISM: Human immunodeficiency virus type 2

<400> SEQUENCE: 29

```
Met Gly Ala Ser Gly Ser Lys Lys Arg Ser Glu Pro Ser Arg Gly Leu
1               5                   10                  15

```
            115                 120                 125
Leu Glu Gly Ile Tyr Tyr Ser Ala Arg Arg His Arg Ile Leu Asp Ile
130                 135                 140

Tyr Leu Glu Lys Glu Glu Gly Ile Ile Pro Asp Trp Gln Asp Tyr Thr
145                 150                 155                 160

Ser Gly Pro Gly Ile Arg Tyr Pro Lys Thr Phe Gly Trp Leu Trp Lys
                165                 170                 175

Leu Val Pro Val Asn Val Ser Asp Glu Ala Gln Glu Asp Glu Glu His
                180                 185                 190

Tyr Leu Met His Pro Ala Gln Thr Ser Gln Trp Asp Asp Pro Trp Gly
            195                 200                 205

Glu Val Leu Ala Trp Lys Phe Asp Pro Thr Leu Ala Tyr Thr Tyr Glu
210                 215                 220

Ala Tyr Val Arg Tyr Pro Glu Glu Phe Gly Ser Lys Ser Gly Leu Ser
225                 230                 235                 240

Glu Glu Glu Val Arg Arg Leu Thr Ala Arg Gly Leu Leu Asn Met
                245                 250                 255

Ala Asp Lys Lys Glu Thr Arg
                260

<210> SEQ ID NO 31
<211> LENGTH: 263
<212> TYPE: PRT
<213> ORGANISM: Artificial sequence
<220> FEATURE:
<223> OTHER INFORMATION: E125R SIV Nef mutant

<400> SEQUENCE: 31

Met Gly Gly Ala Ile Ser Met Arg Arg Ser Arg Pro Ser Gly Asp Leu
1               5                   10                  15

Arg Gln Arg Leu Leu Arg Ala Arg Gly Glu Thr Tyr Gly Arg Leu Leu
            20                  25                  30

Gly Glu Val Glu Asp Gly Tyr Ser Gln Ser Pro Gly Gly Leu Asp Lys
        35                  40                  45

Gly Leu Ser Ser Leu Ser Cys Glu Gly Gln Lys Tyr Asn Gln Gly Gln
    50                  55                  60

Tyr Met Asn Thr Pro Trp Arg Asn Pro Ala Glu Glu Arg Glu Lys Leu
65                  70                  75                  80

Ala Tyr Arg Lys Gln Asn Met Asp Asp Ile Asp Glu Asp Asp Asp
                85                  90                  95

Leu Val Gly Val Ser Val Arg Pro Lys Val Pro Leu Arg Thr Met Ser
                100                 105                 110

Tyr Lys Leu Ala Ile Asp Met Ser His Phe Ile Lys Arg Lys Gly Gly
            115                 120                 125

Leu Glu Gly Ile Tyr Tyr Ser Ala Arg Arg His Arg Ile Leu Asp Ile
130                 135                 140

Tyr Leu Glu Lys Glu Glu Gly Ile Ile Pro Asp Trp Gln Asp Tyr Thr
145                 150                 155                 160

Ser Gly Pro Gly Ile Arg Tyr Pro Lys Thr Phe Gly Trp Leu Trp Lys
                165                 170                 175

Leu Val Pro Val Asn Val Ser Asp Glu Ala Gln Glu Asp Glu Glu His
                180                 185                 190

Tyr Leu Met His Pro Ala Gln Thr Ser Gln Trp Asp Asp Pro Trp Gly
            195                 200                 205

Glu Val Leu Ala Trp Lys Phe Asp Pro Thr Leu Ala Tyr Thr Tyr Glu
```

```
                 210                 215                 220

Ala Tyr Val Arg Tyr Pro Glu Glu Phe Gly Ser Lys Ser Gly Leu Ser
225                 230                 235                 240

Glu Glu Glu Val Arg Arg Leu Thr Ala Arg Gly Leu Leu Asn Met
                245                 250                 255

Ala Asp Lys Lys Glu Thr Arg
            260

<210> SEQ ID NO 32
<211> LENGTH: 41
<212> TYPE: PRT
<213> ORGANISM: Artificial sequence
<220> FEATURE:
<223> OTHER INFORMATION: 80-120 HIV-1 Nef fragment

<400> SEQUENCE: 32

Thr Tyr Lys Ala Ala Val Asp Leu Ser His Phe Leu Lys Glu Lys Gly
1               5                   10                  15

Gly Leu Glu Gly Leu Ile His Ser Gln Arg Arg Gln Asp Ile Leu Asp
            20                  25                  30

Leu Trp Ile Tyr His Thr Gln Gly Tyr
        35                  40

<210> SEQ ID NO 33
<211> LENGTH: 40
<212> TYPE: PRT
<213> ORGANISM: Artificial sequence
<220> FEATURE:
<223> OTHER INFORMATION: 81-120 HIV-1 Nef fragment

<400> SEQUENCE: 33

Tyr Lys Ala Ala Val Asp Leu Ser His Phe Leu Lys Glu Lys Gly Gly
1               5                   10                  15

Leu Glu Gly Leu Ile His Ser Gln Arg Arg Gln Asp Ile Leu Asp Leu
            20                  25                  30

Trp Ile Tyr His Thr Gln Gly Tyr
        35                  40

<210> SEQ ID NO 34
<211> LENGTH: 39
<212> TYPE: PRT
<213> ORGANISM: Artificial sequence
<220> FEATURE:
<223> OTHER INFORMATION: 82-120 HIV-1 Nef fragment

<400> SEQUENCE: 34

Lys Ala Ala Val Asp Leu Ser His Phe Leu Lys Glu Lys Gly Gly Leu
1               5                   10                  15

Glu Gly Leu Ile His Ser Gln Arg Arg Gln Asp Ile Leu Asp Leu Trp
            20                  25                  30

Ile Tyr His Thr Gln Gly Tyr
        35

<210> SEQ ID NO 35
<211> LENGTH: 38
<212> TYPE: PRT
<213> ORGANISM: Artificial sequence
<220> FEATURE:
<223> OTHER INFORMATION: 83-120 HIV-1 Nef fragment

<400> SEQUENCE: 35

Ala Ala Val Asp Leu Ser His Phe Leu Lys Glu Lys Gly Gly Leu Glu
```

-continued

```
                1               5                  10                  15
Gly Leu Ile His Ser Gln Arg Arg Gln Asp Ile Leu Asp Leu Trp Ile
                        20                  25                  30

Tyr His Thr Gln Gly Tyr
            35

<210> SEQ ID NO 36
<211> LENGTH: 37
<212> TYPE: PRT
<213> ORGANISM: Artificial sequence
<220> FEATURE:
<223> OTHER INFORMATION: 84-120 HIV-1 Nef fragment

<400> SEQUENCE: 36

Ala Val Asp Leu Ser His Phe Leu Lys Glu Lys Gly Gly Leu Glu Gly
1               5                   10                  15

Leu Ile His Ser Gln Arg Arg Gln Asp Ile Leu Asp Leu Trp Ile Tyr
                20                  25                  30

His Thr Gln Gly Tyr
            35

<210> SEQ ID NO 37
<211> LENGTH: 36
<212> TYPE: PRT
<213> ORGANISM: Artificial sequence
<220> FEATURE:
<223> OTHER INFORMATION: 85-120 HIV-1 Nef fragment

<400> SEQUENCE: 37

Val Asp Leu Ser His Phe Leu Lys Glu Lys Gly Gly Leu Glu Gly Leu
1               5                   10                  15

Ile His Ser Gln Arg Arg Gln Asp Ile Leu Asp Leu Trp Ile Tyr His
                20                  25                  30

Thr Gln Gly Tyr
            35

<210> SEQ ID NO 38
<211> LENGTH: 35
<212> TYPE: PRT
<213> ORGANISM: Artificial sequence
<220> FEATURE:
<223> OTHER INFORMATION: 86-120 HIV-1 Nef fragment

<400> SEQUENCE: 38

Asp Leu Ser His Phe Leu Lys Glu Lys Gly Gly Leu Glu Gly Leu Ile
1               5                   10                  15

His Ser Gln Arg Arg Gln Asp Ile Leu Asp Leu Trp Ile Tyr His Thr
                20                  25                  30

Gln Gly Tyr
        35

<210> SEQ ID NO 39
<211> LENGTH: 34
<212> TYPE: PRT
<213> ORGANISM: Artificial sequence
<220> FEATURE:
<223> OTHER INFORMATION: 87-120 HIV-1 Nef fragment

<400> SEQUENCE: 39

Leu Ser His Phe Leu Lys Glu Lys Gly Gly Leu Glu Gly Leu Ile His
1               5                   10                  15

Ser Gln Arg Arg Gln Asp Ile Leu Asp Leu Trp Ile Tyr His Thr Gln
```

-continued

```
                20                  25                  30

Gly Tyr

<210> SEQ ID NO 40
<211> LENGTH: 33
<212> TYPE: PRT
<213> ORGANISM: Artificial sequence
<220> FEATURE:
<223> OTHER INFORMATION: 88-120 HIV-1 Nef fragment

<400> SEQUENCE: 40

Ser His Phe Leu Lys Glu Lys Gly Gly Leu Glu Gly Leu Ile His Ser
1               5                   10                  15

Gln Arg Arg Gln Asp Ile Leu Asp Leu Trp Ile Tyr His Thr Gln Gly
                20                  25                  30

Tyr

<210> SEQ ID NO 41
<211> LENGTH: 32
<212> TYPE: PRT
<213> ORGANISM: Artificial sequence
<220> FEATURE:
<223> OTHER INFORMATION: 89-120 HIV-1 Nef fragment

<400> SEQUENCE: 41

His Phe Leu Lys Glu Lys Gly Gly Leu Glu Gly Leu Ile His Ser Gln
1               5                   10                  15

Arg Arg Gln Asp Ile Leu Asp Leu Trp Ile Tyr His Thr Gln Gly Tyr
                20                  25                  30

<210> SEQ ID NO 42
<211> LENGTH: 31
<212> TYPE: PRT
<213> ORGANISM: Artificial sequence
<220> FEATURE:
<223> OTHER INFORMATION: 90-120 HIV-1 Nef fragment

<400> SEQUENCE: 42

Phe Leu Lys Glu Lys Gly Gly Leu Glu Gly Leu Ile His Ser Gln Arg
1               5                   10                  15

Arg Gln Asp Ile Leu Asp Leu Trp Ile Tyr His Thr Gln Gly Tyr
                20                  25                  30

<210> SEQ ID NO 43
<211> LENGTH: 40
<212> TYPE: PRT
<213> ORGANISM: Artificial sequence
<220> FEATURE:
<223> OTHER INFORMATION: 80-119 HIV-1 Nef fragment

<400> SEQUENCE: 43

Thr Tyr Lys Ala Ala Val Asp Leu Ser His Phe Leu Lys Glu Lys Gly
1               5                   10                  15

Gly Leu Glu Gly Leu Ile His Ser Gln Arg Arg Gln Asp Ile Leu Asp
                20                  25                  30

Leu Trp Ile Tyr His Thr Gln Gly
        35                  40

<210> SEQ ID NO 44
<211> LENGTH: 39
<212> TYPE: PRT
<213> ORGANISM: Artificial sequence
<220> FEATURE:
```

```
<223> OTHER INFORMATION: 81-119 HIV-1 Nef fragment

<400> SEQUENCE: 44

Tyr Lys Ala Ala Val Asp Leu Ser His Phe Leu Lys Glu Lys Gly Gly
1               5                   10                  15
Leu Glu Gly Leu Ile His Ser Gln Arg Arg Gln Asp Ile Leu Asp Leu
            20                  25                  30
Trp Ile Tyr His Thr Gln Gly
        35

<210> SEQ ID NO 45
<211> LENGTH: 38
<212> TYPE: PRT
<213> ORGANISM: Artificial sequence
<220> FEATURE:
<223> OTHER INFORMATION: 82-119 HIV-1 Nef fragment

<400> SEQUENCE: 45

Lys Ala Ala Val Asp Leu Ser His Phe Leu Lys Glu Lys Gly Gly Leu
1               5                   10                  15
Glu Gly Leu Ile His Ser Gln Arg Arg Gln Asp Ile Leu Asp Leu Trp
            20                  25                  30
Ile Tyr His Thr Gln Gly
        35

<210> SEQ ID NO 46
<211> LENGTH: 37
<212> TYPE: PRT
<213> ORGANISM: Artificial sequence
<220> FEATURE:
<223> OTHER INFORMATION: 83-119 HIV-1 Nef fragment

<400> SEQUENCE: 46

Ala Ala Val Asp Leu Ser His Phe Leu Lys Glu Lys Gly Gly Leu Glu
1               5                   10                  15
Gly Leu Ile His Ser Gln Arg Arg Gln Asp Ile Leu Asp Leu Trp Ile
            20                  25                  30
Tyr His Thr Gln Gly
        35

<210> SEQ ID NO 47
<211> LENGTH: 36
<212> TYPE: PRT
<213> ORGANISM: Artificial sequence
<220> FEATURE:
<223> OTHER INFORMATION: 84-119 HIV-1 Nef fragment

<400> SEQUENCE: 47

Ala Val Asp Leu Ser His Phe Leu Lys Glu Lys Gly Gly Leu Glu Gly
1               5                   10                  15
Leu Ile His Ser Gln Arg Arg Gln Asp Ile Leu Asp Leu Trp Ile Tyr
            20                  25                  30
His Thr Gln Gly
        35

<210> SEQ ID NO 48
<211> LENGTH: 35
<212> TYPE: PRT
<213> ORGANISM: Artificial sequence
<220> FEATURE:
<223> OTHER INFORMATION: 85-119 HIV-1 Nef fragment

<400> SEQUENCE: 48
```

```
Val Asp Leu Ser His Phe Leu Lys Glu Lys Gly Gly Leu Glu Gly Leu
1               5                   10                  15

Ile His Ser Gln Arg Arg Gln Asp Ile Leu Asp Leu Trp Ile Tyr His
            20                  25                  30

Thr Gln Gly
        35

<210> SEQ ID NO 49
<211> LENGTH: 34
<212> TYPE: PRT
<213> ORGANISM: Artificial sequence
<220> FEATURE:
<223> OTHER INFORMATION: 86-119 HIV-1 Nef fragment

<400> SEQUENCE: 49

Asp Leu Ser His Phe Leu Lys Glu Lys Gly Gly Leu Glu Gly Leu Ile
1               5                   10                  15

His Ser Gln Arg Arg Gln Asp Ile Leu Asp Leu Trp Ile Tyr His Thr
            20                  25                  30

Gln Gly

<210> SEQ ID NO 50
<211> LENGTH: 33
<212> TYPE: PRT
<213> ORGANISM: Artificial sequence
<220> FEATURE:
<223> OTHER INFORMATION: 87-119 HIV-1 Nef fragment

<400> SEQUENCE: 50

Leu Ser His Phe Leu Lys Glu Lys Gly Gly Leu Glu Gly Leu Ile His
1               5                   10                  15

Ser Gln Arg Arg Gln Asp Ile Leu Asp Leu Trp Ile Tyr His Thr Gln
            20                  25                  30

Gly

<210> SEQ ID NO 51
<211> LENGTH: 32
<212> TYPE: PRT
<213> ORGANISM: Artificial sequence
<220> FEATURE:
<223> OTHER INFORMATION: 88-119 HIV-1 Nef fragment

<400> SEQUENCE: 51

Ser His Phe Leu Lys Glu Lys Gly Gly Leu Glu Gly Leu Ile His Ser
1               5                   10                  15

Gln Arg Arg Gln Asp Ile Leu Asp Leu Trp Ile Tyr His Thr Gln Gly
            20                  25                  30

<210> SEQ ID NO 52
<211> LENGTH: 31
<212> TYPE: PRT
<213> ORGANISM: Artificial sequence
<220> FEATURE:
<223> OTHER INFORMATION: 89-119 HIV-1 Nef fragment

<400> SEQUENCE: 52

His Phe Leu Lys Glu Lys Gly Gly Leu Glu Gly Leu Ile His Ser Gln
1               5                   10                  15

Arg Arg Gln Asp Ile Leu Asp Leu Trp Ile Tyr His Thr Gln Gly
            20                  25                  30
```

<210> SEQ ID NO 53
<211> LENGTH: 30
<212> TYPE: PRT
<213> ORGANISM: Artificial sequence
<220> FEATURE:
<223> OTHER INFORMATION: 90-119 HIV-1 Nef fragment

<400> SEQUENCE: 53

Phe Leu Lys Glu Lys Gly Gly Leu Glu Gly Leu Ile His Ser Gln Arg
1               5                   10                  15

Arg Gln Asp Ile Leu Asp Leu Trp Ile Tyr His Thr Gln Gly
            20                  25                  30

<210> SEQ ID NO 54
<211> LENGTH: 39
<212> TYPE: PRT
<213> ORGANISM: Artificial sequence
<220> FEATURE:
<223> OTHER INFORMATION: 80-118 HIV-1 Nef fragment

<400> SEQUENCE: 54

Thr Tyr Lys Ala Ala Val Asp Leu Ser His Phe Leu Lys Glu Lys Gly
1               5                   10                  15

Gly Leu Glu Gly Leu Ile His Ser Gln Arg Arg Gln Asp Ile Leu Asp
            20                  25                  30

Leu Trp Ile Tyr His Thr Gln
        35

<210> SEQ ID NO 55
<211> LENGTH: 38
<212> TYPE: PRT
<213> ORGANISM: Artificial sequence
<220> FEATURE:
<223> OTHER INFORMATION: 81-118 HIV-1 Nef fragment

<400> SEQUENCE: 55

Tyr Lys Ala Ala Val Asp Leu Ser His Phe Leu Lys Glu Lys Gly Gly
1               5                   10                  15

Leu Glu Gly Leu Ile His Ser Gln Arg Arg Gln Asp Ile Leu Asp Leu
            20                  25                  30

Trp Ile Tyr His Thr Gln
        35

<210> SEQ ID NO 56
<211> LENGTH: 37
<212> TYPE: PRT
<213> ORGANISM: Artificial sequence
<220> FEATURE:
<223> OTHER INFORMATION: 82-118 HIV-1 Nef fragment

<400> SEQUENCE: 56

Lys Ala Ala Val Asp Leu Ser His Phe Leu Lys Glu Lys Gly Gly Leu
1               5                   10                  15

Glu Gly Leu Ile His Ser Gln Arg Arg Gln Asp Ile Leu Asp Leu Trp
            20                  25                  30

Ile Tyr His Thr Gln
        35

<210> SEQ ID NO 57
<211> LENGTH: 36
<212> TYPE: PRT
<213> ORGANISM: Artificial sequence
<220> FEATURE:
<223> OTHER INFORMATION: 83-118 HIV-1 Nef fragment -continued

```
<400> SEQUENCE: 57

Ala Ala Val Asp Leu Ser His Phe Leu Lys Glu Lys Gly Gly Leu Glu
1               5                   10                  15

Gly Leu Ile His Ser Gln Arg Arg Gln Asp Ile Leu Asp Leu Trp Ile
            20                  25                  30

Tyr His Thr Gln
        35

<210> SEQ ID NO 58
<211> LENGTH: 35
<212> TYPE: PRT
<213> ORGANISM: Artificial sequence
<220> FEATURE:
<223> OTHER INFORMATION: 84-118 HIV-1 Nef fragment

<400> SEQUENCE: 58

Ala Val Asp Leu Ser His Phe Leu Lys Glu Lys Gly Gly Leu Glu Gly
1               5                   10                  15

Leu Ile His Ser Gln Arg Arg Gln Asp Ile Leu Asp Leu Trp Ile Tyr
            20                  25                  30

His Thr Gln
        35

<210> SEQ ID NO 59
<211> LENGTH: 34
<212> TYPE: PRT
<213> ORGANISM: Artificial sequence
<220> FEATURE:
<223> OTHER INFORMATION: 85-118 HIV-1 Nef fragment

<400> SEQUENCE: 59

Val Asp Leu Ser His Phe Leu Lys Glu Lys Gly Gly Leu Glu Gly Leu
1               5                   10                  15

Ile His Ser Gln Arg Arg Gln Asp Ile Leu Asp Leu Trp Ile Tyr His
            20                  25                  30

Thr Gln

<210> SEQ ID NO 60
<211> LENGTH: 33
<212> TYPE: PRT
<213> ORGANISM: Artificial sequence
<220> FEATURE:
<223> OTHER INFORMATION: 86-118 HIV-1 Nef fragment

<400> SEQUENCE: 60

Asp Leu Ser His Phe Leu Lys Glu Lys Gly Gly Leu Glu Gly Leu Ile
1               5                   10                  15

His Ser Gln Arg Arg Gln Asp Ile Leu Asp Leu Trp Ile Tyr His Thr
            20                  25                  30

Gln

<210> SEQ ID NO 61
<211> LENGTH: 32
<212> TYPE: PRT
<213> ORGANISM: Artificial sequence
<220> FEATURE:
<223> OTHER INFORMATION: 87-118 HIV-1 Nef fragment

<400> SEQUENCE: 61

Leu Ser His Phe Leu Lys Glu Lys Gly Gly Leu Glu Gly Leu Ile His
1               5                   10                  15
```

Ser Gln Arg Arg Gln Asp Ile Leu Asp Leu Trp Ile Tyr His Thr Gln
            20                  25                  30

<210> SEQ ID NO 62
<211> LENGTH: 31
<212> TYPE: PRT
<213> ORGANISM: Artificial sequence
<220> FEATURE:
<223> OTHER INFORMATION: 88-118 HIV-1 Nef fragment

<400> SEQUENCE: 62

Ser His Phe Leu Lys Glu Lys Gly Gly Leu Glu Gly Leu Ile His Ser
1               5                   10                  15

Gln Arg Arg Gln Asp Ile Leu Asp Leu Trp Ile Tyr His Thr Gln
            20                  25                  30

<210> SEQ ID NO 63
<211> LENGTH: 30
<212> TYPE: PRT
<213> ORGANISM: Artificial sequence
<220> FEATURE:
<223> OTHER INFORMATION: 89-118 HIV-1 Nef fragment

<400> SEQUENCE: 63

His Phe Leu Lys Glu Lys Gly Gly Leu Glu Gly Leu Ile His Ser Gln
1               5                   10                  15

Arg Arg Gln Asp Ile Leu Asp Leu Trp Ile Tyr His Thr Gln
            20                  25                  30

<210> SEQ ID NO 64
<211> LENGTH: 29
<212> TYPE: PRT
<213> ORGANISM: Artificial sequence
<220> FEATURE:
<223> OTHER INFORMATION: 90-118 HIV-1 Nef fragment

<400> SEQUENCE: 64

Phe Leu Lys Glu Lys Gly Gly Leu Glu Gly Leu Ile His Ser Gln Arg
1               5                   10                  15

Arg Gln Asp Ile Leu Asp Leu Trp Ile Tyr His Thr Gln
            20                  25

<210> SEQ ID NO 65
<211> LENGTH: 38
<212> TYPE: PRT
<213> ORGANISM: Artificial sequence
<220> FEATURE:
<223> OTHER INFORMATION: 80-117 HIV-1 Nef fragment

<400> SEQUENCE: 65

Thr Tyr Lys Ala Ala Val Asp Leu Ser His Phe Leu Lys Glu Lys Gly
1               5                   10                  15

Gly Leu Glu Gly Leu Ile His Ser Gln Arg Arg Gln Asp Ile Leu Asp
            20                  25                  30

Leu Trp Ile Tyr His Thr
        35

<210> SEQ ID NO 66
<211> LENGTH: 37
<212> TYPE: PRT
<213> ORGANISM: Artificial sequence
<220> FEATURE:
<223> OTHER INFORMATION: 81-117 HIV-1 Nef fragment

```
<400> SEQUENCE: 66

Tyr Lys Ala Ala Val Asp Leu Ser His Phe Leu Lys Glu Lys Gly Gly
1               5                   10                  15

Leu Glu Gly Leu Ile His Ser Gln Arg Arg Gln Asp Ile Leu Asp Leu
            20                  25                  30

Trp Ile Tyr His Thr
            35

<210> SEQ ID NO 67
<211> LENGTH: 36
<212> TYPE: PRT
<213> ORGANISM: Artificial sequence
<220> FEATURE:
<223> OTHER INFORMATION: 82-117 HIV-1 Nef fragment

<400> SEQUENCE: 67

Lys Ala Ala Val Asp Leu Ser His Phe Leu Lys Glu Lys Gly Gly Leu
1               5                   10                  15

Glu Gly Leu Ile His Ser Gln Arg Arg Gln Asp Ile Leu Asp Leu Trp
            20                  25                  30

Ile Tyr His Thr
        35

<210> SEQ ID NO 68
<211> LENGTH: 35
<212> TYPE: PRT
<213> ORGANISM: Artificial sequence
<220> FEATURE:
<223> OTHER INFORMATION: 83-117 HIV-1 Nef fragment

<400> SEQUENCE: 68

Ala Ala Val Asp Leu Ser His Phe Leu Lys Glu Lys Gly Gly Leu Glu
1               5                   10                  15

Gly Leu Ile His Ser Gln Arg Arg Gln Asp Ile Leu Asp Leu Trp Ile
            20                  25                  30

Tyr His Thr
        35

<210> SEQ ID NO 69
<211> LENGTH: 34
<212> TYPE: PRT
<213> ORGANISM: Artificial sequence
<220> FEATURE:
<223> OTHER INFORMATION: 84-117 HIV-1 Nef fragment

<400> SEQUENCE: 69

Ala Val Asp Leu Ser His Phe Leu Lys Glu Lys Gly Gly Leu Glu Gly
1               5                   10                  15

Leu Ile His Ser Gln Arg Arg Gln Asp Ile Leu Asp Leu Trp Ile Tyr
            20                  25                  30

His Thr

<210> SEQ ID NO 70
<211> LENGTH: 33
<212> TYPE: PRT
<213> ORGANISM: Artificial sequence
<220> FEATURE:
<223> OTHER INFORMATION: 85-117 HIV-1 Nef fragment

<400> SEQUENCE: 70

Val Asp Leu Ser His Phe Leu Lys Glu Lys Gly Gly Leu Glu Gly Leu
1               5                   10                  15
```

```
Ile His Ser Gln Arg Arg Gln Asp Ile Leu Asp Leu Trp Ile Tyr His
            20                  25                  30

Thr
```

<210> SEQ ID NO 71
<211> LENGTH: 32
<212> TYPE: PRT
<213> ORGANISM: Artificial sequence
<220> FEATURE:
<223> OTHER INFORMATION: 86-117 HIV-1 Nef fragment

<400> SEQUENCE: 71

```
Asp Leu Ser His Phe Leu Lys Glu Lys Gly Gly Leu Glu Gly Leu Ile
1               5                   10                  15

His Ser Gln Arg Arg Gln Asp Ile Leu Asp Leu Trp Ile Tyr His Thr
            20                  25                  30
```

<210> SEQ ID NO 72
<211> LENGTH: 31
<212> TYPE: PRT
<213> ORGANISM: Artificial sequence
<220> FEATURE:
<223> OTHER INFORMATION: 87-117 HIV-1 Nef fragment

<400> SEQUENCE: 72

```
Leu Ser His Phe Leu Lys Glu Lys Gly Gly Leu Glu Gly Leu Ile His
1               5                   10                  15

Ser Gln Arg Arg Gln Asp Ile Leu Asp Leu Trp Ile Tyr His Thr
            20                  25                  30
```

<210> SEQ ID NO 73
<211> LENGTH: 30
<212> TYPE: PRT
<213> ORGANISM: Artificial sequence
<220> FEATURE:
<223> OTHER INFORMATION: 88-117 HIV-1 Nef fragment

<400> SEQUENCE: 73

```
Ser His Phe Leu Lys Glu Lys Gly Gly Leu Glu Gly Leu Ile His Ser
1               5                   10                  15

Gln Arg Arg Gln Asp Ile Leu Asp Leu Trp Ile Tyr His Thr
            20                  25                  30
```

<210> SEQ ID NO 74
<211> LENGTH: 29
<212> TYPE: PRT
<213> ORGANISM: Artificial sequence
<220> FEATURE:
<223> OTHER INFORMATION: 89-117 HIV-1 Nef fragment

<400> SEQUENCE: 74

```
His Phe Leu Lys Glu Lys Gly Gly Leu Glu Gly Leu Ile His Ser Gln
1               5                   10                  15

Arg Arg Gln Asp Ile Leu Asp Leu Trp Ile Tyr His Thr
            20                  25
```

<210> SEQ ID NO 75
<211> LENGTH: 28
<212> TYPE: PRT
<213> ORGANISM: Artificial sequence
<220> FEATURE:
<223> OTHER INFORMATION: 90-117 HIV-1 Nef fragment

<400> SEQUENCE: 75

Phe Leu Lys Glu Lys Gly Gly Leu Glu Gly Leu Ile His Ser Gln Arg
1               5                   10                  15

Arg Gln Asp Ile Leu Asp Leu Trp Ile Tyr His Thr
            20                  25

<210> SEQ ID NO 76
<211> LENGTH: 37
<212> TYPE: PRT
<213> ORGANISM: Artificial sequence
<220> FEATURE:
<223> OTHER INFORMATION: 80-116 HIV-1 Nef fragment

<400> SEQUENCE: 76

Thr Tyr Lys Ala Ala Val Asp Leu Ser His Phe Leu Lys Glu Lys Gly
1               5                   10                  15

Gly Leu Glu Gly Leu Ile His Ser Gln Arg Arg Gln Asp Ile Leu Asp
            20                  25                  30

Leu Trp Ile Tyr His
        35

<210> SEQ ID NO 77
<211> LENGTH: 36
<212> TYPE: PRT
<213> ORGANISM: Artificial sequence
<220> FEATURE:
<223> OTHER INFORMATION: 81-116 HIV-1 Nef fragment

<400> SEQUENCE: 77

Tyr Lys Ala Ala Val Asp Leu Ser His Phe Leu Lys Glu Lys Gly Gly
1               5                   10                  15

Leu Glu Gly Leu Ile His Ser Gln Arg Arg Gln Asp Ile Leu Asp Leu
            20                  25                  30

Trp Ile Tyr His
        35

<210> SEQ ID NO 78
<211> LENGTH: 35
<212> TYPE: PRT
<213> ORGANISM: Artificial sequence
<220> FEATURE:
<223> OTHER INFORMATION: 82-116 HIV-1 Nef fragment

<400> SEQUENCE: 78

Lys Ala Ala Val Asp Leu Ser His Phe Leu Lys Glu Lys Gly Gly Leu
1               5                   10                  15

Glu Gly Leu Ile His Ser Gln Arg Arg Gln Asp Ile Leu Asp Leu Trp
            20                  25                  30

Ile Tyr His
        35

<210> SEQ ID NO 79
<211> LENGTH: 34
<212> TYPE: PRT
<213> ORGANISM: Artificial sequence
<220> FEATURE:
<223> OTHER INFORMATION: 83-116 HIV-1 Nef fragment

<400> SEQUENCE: 79

Ala Ala Val Asp Leu Ser His Phe Leu Lys Glu Lys Gly Gly Leu Glu
1               5                   10                  15

Gly Leu Ile His Ser Gln Arg Arg Gln Asp Ile Leu Asp Leu Trp Ile
            20                  25                  30

Tyr His

<210> SEQ ID NO 80
<211> LENGTH: 33
<212> TYPE: PRT
<213> ORGANISM: Artificial sequence
<220> FEATURE:
<223> OTHER INFORMATION: 84-116 HIV-1 Nef fragment

<400> SEQUENCE: 80

Ala Val Asp Leu Ser His Phe Leu Lys Glu Lys Gly Gly Leu Glu Gly
1               5                   10                  15

Leu Ile His Ser Gln Arg Arg Gln Asp Ile Leu Asp Leu Trp Ile Tyr
            20                  25                  30

His

<210> SEQ ID NO 81
<211> LENGTH: 32
<212> TYPE: PRT
<213> ORGANISM: Artificial sequence
<220> FEATURE:
<223> OTHER INFORMATION: 85-116 HIV-1 Nef fragment

<400> SEQUENCE: 81

Val Asp Leu Ser His Phe Leu Lys Glu Lys Gly Gly Leu Glu Gly Leu
1               5                   10                  15

Ile His Ser Gln Arg Arg Gln Asp Ile Leu Asp Leu Trp Ile Tyr His
            20                  25                  30

<210> SEQ ID NO 82
<211> LENGTH: 31
<212> TYPE: PRT
<213> ORGANISM: Artificial sequence
<220> FEATURE:
<223> OTHER INFORMATION: 86-116 HIV-1 Nef fragment

<400> SEQUENCE: 82

Asp Leu Ser His Phe Leu Lys Glu Lys Gly Gly Leu Glu Gly Leu Ile
1               5                   10                  15

His Ser Gln Arg Arg Gln Asp Ile Leu Asp Leu Trp Ile Tyr His
            20                  25                  30

<210> SEQ ID NO 83
<211> LENGTH: 30
<212> TYPE: PRT
<213> ORGANISM: Artificial sequence
<220> FEATURE:
<223> OTHER INFORMATION: 87-116 HIV-1 Nef fragment

<400> SEQUENCE: 83

Leu Ser His Phe Leu Lys Glu Lys Gly Gly Leu Glu Gly Leu Ile His
1               5                   10                  15

Ser Gln Arg Arg Gln Asp Ile Leu Asp Leu Trp Ile Tyr His
            20                  25                  30

<210> SEQ ID NO 84
<211> LENGTH: 29
<212> TYPE: PRT
<213> ORGANISM: Artificial sequence
<220> FEATURE:
<223> OTHER INFORMATION: 88-116 HIV-1 Nef fragment

<400> SEQUENCE: 84

-continued

```
Ser His Phe Leu Lys Glu Lys Gly Gly Leu Glu Gly Leu Ile His Ser
1               5                   10                  15

Gln Arg Arg Gln Asp Ile Leu Asp Leu Trp Ile Tyr His
            20                  25
```

<210> SEQ ID NO 85
<211> LENGTH: 28
<212> TYPE: PRT
<213> ORGANISM: Artificial sequence
<220> FEATURE:
<223> OTHER INFORMATION: 89-116 HIV-1 Nef fragment

<400> SEQUENCE: 85

```
His Phe Leu Lys Glu Lys Gly Gly Leu Glu Gly Leu Ile His Ser Gln
1               5                   10                  15

Arg Arg Gln Asp Ile Leu Asp Leu Trp Ile Tyr His
            20                  25
```

<210> SEQ ID NO 86
<211> LENGTH: 27
<212> TYPE: PRT
<213> ORGANISM: Artificial sequence
<220> FEATURE:
<223> OTHER INFORMATION: 90-116 HIV-1 Nef fragment

<400> SEQUENCE: 86

```
Phe Leu Lys Glu Lys Gly Gly Leu Glu Gly Leu Ile His Ser Gln Arg
1               5                   10                  15

Arg Gln Asp Ile Leu Asp Leu Trp Ile Tyr His
            20                  25
```

<210> SEQ ID NO 87
<211> LENGTH: 36
<212> TYPE: PRT
<213> ORGANISM: Artificial sequence
<220> FEATURE:
<223> OTHER INFORMATION: 80-115 HIV-1 Nef fragment

<400> SEQUENCE: 87

```
Thr Tyr Lys Ala Ala Val Asp Leu Ser His Phe Leu Lys Glu Lys Gly
1               5                   10                  15

Gly Leu Glu Gly Leu Ile His Ser Gln Arg Arg Gln Asp Ile Leu Asp
            20                  25                  30

Leu Trp Ile Tyr
        35
```

<210> SEQ ID NO 88
<211> LENGTH: 35
<212> TYPE: PRT
<213> ORGANISM: Artificial sequence
<220> FEATURE:
<223> OTHER INFORMATION: 81-115 HIV-1 Nef fragment

<400> SEQUENCE: 88

```
Tyr Lys Ala Ala Val Asp Leu Ser His Phe Leu Lys Glu Lys Gly Gly
1               5                   10                  15

Leu Glu Gly Leu Ile His Ser Gln Arg Arg Gln Asp Ile Leu Asp Leu
            20                  25                  30

Trp Ile Tyr
        35
```

<210> SEQ ID NO 89
<211> LENGTH: 34

<212> TYPE: PRT
<213> ORGANISM: Artificial sequence
<220> FEATURE:
<223> OTHER INFORMATION: 82-115 HIV-1 Nef fragment

<400> SEQUENCE: 89

Lys Ala Ala Val Asp Leu Ser His Phe Leu Lys Glu Lys Gly Gly Leu
1               5                   10                  15

Glu Gly Leu Ile His Ser Gln Arg Arg Gln Asp Ile Leu Asp Leu Trp
            20                  25                  30

Ile Tyr

<210> SEQ ID NO 90
<211> LENGTH: 33
<212> TYPE: PRT
<213> ORGANISM: Artificial sequence
<220> FEATURE:
<223> OTHER INFORMATION: 83-115 HIV-1 Nef fragment

<400> SEQUENCE: 90

Ala Ala Val Asp Leu Ser His Phe Leu Lys Glu Lys Gly Gly Leu Glu
1               5                   10                  15

Gly Leu Ile His Ser Gln Arg Arg Gln Asp Ile Leu Asp Leu Trp Ile
            20                  25                  30

Tyr

<210> SEQ ID NO 91
<211> LENGTH: 32
<212> TYPE: PRT
<213> ORGANISM: Artificial sequence
<220> FEATURE:
<223> OTHER INFORMATION: 84-115 HIV-1 Nef fragment

<400> SEQUENCE: 91

Ala Val Asp Leu Ser His Phe Leu Lys Glu Lys Gly Gly Leu Glu Gly
1               5                   10                  15

Leu Ile His Ser Gln Arg Arg Gln Asp Ile Leu Asp Leu Trp Ile Tyr
            20                  25                  30

<210> SEQ ID NO 92
<211> LENGTH: 31
<212> TYPE: PRT
<213> ORGANISM: Artificial sequence
<220> FEATURE:
<223> OTHER INFORMATION: 85-115 HIV-1 Nef fragment

<400> SEQUENCE: 92

Val Asp Leu Ser His Phe Leu Lys Glu Lys Gly Gly Leu Glu Gly Leu
1               5                   10                  15

Ile His Ser Gln Arg Arg Gln Asp Ile Leu Asp Leu Trp Ile Tyr
            20                  25                  30

<210> SEQ ID NO 93
<211> LENGTH: 30
<212> TYPE: PRT
<213> ORGANISM: Artificial sequence
<220> FEATURE:
<223> OTHER INFORMATION: 86-115 HIV-1 Nef fragment

<400> SEQUENCE: 93

Asp Leu Ser His Phe Leu Lys Glu Lys Gly Gly Leu Glu Gly Leu Ile
1               5                   10                  15

His Ser Gln Arg Arg Gln Asp Ile Leu Asp Leu Trp Ile Tyr

-continued

```
                 20                  25                  30
```

<210> SEQ ID NO 94
<211> LENGTH: 29
<212> TYPE: PRT
<213> ORGANISM: Artificial sequence
<220> FEATURE:
<223> OTHER INFORMATION: 87-115 HIV-1 Nef fragment

<400> SEQUENCE: 94

Leu Ser His Phe Leu Lys Glu Lys Gly Gly Leu Glu Gly Leu Ile His
1               5                   10                  15

Ser Gln Arg Arg Gln Asp Ile Leu Asp Leu Trp Ile Tyr
            20                  25

<210> SEQ ID NO 95
<211> LENGTH: 28
<212> TYPE: PRT
<213> ORGANISM: Artificial sequence
<220> FEATURE:
<223> OTHER INFORMATION: 88-115 HIV-1 Nef fragment

<400> SEQUENCE: 95

Ser His Phe Leu Lys Glu Lys Gly Gly Leu Glu Gly Leu Ile His Ser
1               5                   10                  15

Gln Arg Arg Gln Asp Ile Leu Asp Leu Trp Ile Tyr
            20                  25

<210> SEQ ID NO 96
<211> LENGTH: 27
<212> TYPE: PRT
<213> ORGANISM: Artificial sequence
<220> FEATURE:
<223> OTHER INFORMATION: 89-115 HIV-1 Nef fragment

<400> SEQUENCE: 96

His Phe Leu Lys Glu Lys Gly Gly Leu Glu Gly Leu Ile His Ser Gln
1               5                   10                  15

Arg Arg Gln Asp Ile Leu Asp Leu Trp Ile Tyr
            20                  25

<210> SEQ ID NO 97
<211> LENGTH: 26
<212> TYPE: PRT
<213> ORGANISM: Artificial sequence
<220> FEATURE:
<223> OTHER INFORMATION: 90-115 HIV-1 Nef fragment

<400> SEQUENCE: 97

Phe Leu Lys Glu Lys Gly Gly Leu Glu Gly Leu Ile His Ser Gln Arg
1               5                   10                  15

Arg Gln Asp Ile Leu Asp Leu Trp Ile Tyr
            20                  25

<210> SEQ ID NO 98
<211> LENGTH: 35
<212> TYPE: PRT
<213> ORGANISM: Artificial sequence
<220> FEATURE:
<223> OTHER INFORMATION: 80-114 HIV-1 Nef fragment

<400> SEQUENCE: 98

Thr Tyr Lys Ala Ala Val Asp Leu Ser His Phe Leu Lys Glu Lys Gly
1               5                   10                  15

Gly Leu Glu Gly Leu Ile His Ser Gln Arg Arg Gln Asp Ile Leu Asp
            20                  25                  30

Leu Trp Ile
        35

<210> SEQ ID NO 99
<211> LENGTH: 34
<212> TYPE: PRT
<213> ORGANISM: Artificial sequence
<220> FEATURE:
<223> OTHER INFORMATION: 81-114 HIV-1 Nef fragment

<400> SEQUENCE: 99

Tyr Lys Ala Ala Val Asp Leu Ser His Phe Leu Lys Glu Lys Gly Gly
1               5                   10                  15

Leu Glu Gly Leu Ile His Ser Gln Arg Arg Gln Asp Ile Leu Asp Leu
            20                  25                  30

Trp Ile

<210> SEQ ID NO 100
<211> LENGTH: 33
<212> TYPE: PRT
<213> ORGANISM: Artificial sequence
<220> FEATURE:
<223> OTHER INFORMATION: 82-114 HIV-1 Nef fragment

<400> SEQUENCE: 100

Lys Ala Ala Val Asp Leu Ser His Phe Leu Lys Glu Lys Gly Gly Leu
1               5                   10                  15

Glu Gly Leu Ile His Ser Gln Arg Arg Gln Asp Ile Leu Asp Leu Trp
            20                  25                  30

Ile

<210> SEQ ID NO 101
<211> LENGTH: 32
<212> TYPE: PRT
<213> ORGANISM: Artificial sequence
<220> FEATURE:
<223> OTHER INFORMATION: 83-114 HIV-1 Nef fragment

<400> SEQUENCE: 101

Ala Ala Val Asp Leu Ser His Phe Leu Lys Glu Lys Gly Gly Leu Glu
1               5                   10                  15

Gly Leu Ile His Ser Gln Arg Arg Gln Asp Ile Leu Asp Leu Trp Ile
            20                  25                  30

<210> SEQ ID NO 102
<211> LENGTH: 31
<212> TYPE: PRT
<213> ORGANISM: Artificial sequence
<220> FEATURE:
<223> OTHER INFORMATION: 84-114 HIV-1 Nef fragment

<400> SEQUENCE: 102

Ala Val Asp Leu Ser His Phe Leu Lys Glu Lys Gly Gly Leu Glu Gly
1               5                   10                  15

Leu Ile His Ser Gln Arg Arg Gln Asp Ile Leu Asp Leu Trp Ile
            20                  25                  30

<210> SEQ ID NO 103
<211> LENGTH: 30
<212> TYPE: PRT
<213> ORGANISM: Artificial sequence
<220> FEATURE:
<223> OTHER INFORMATION: 85-114 HIV-1 Nef fragment

<400> SEQUENCE: 103

Val Asp Leu Ser His Phe Leu Lys Glu Lys Gly Gly Leu Glu Gly Leu
1               5                   10                  15

Ile His Ser Gln Arg Arg Gln Asp Ile Leu Asp Leu Trp Ile
            20                  25                  30

<210> SEQ ID NO 104
<211> LENGTH: 29
<212> TYPE: PRT
<213> ORGANISM: Artificial sequence
<220> FEATURE:
<223> OTHER INFORMATION: 86-114 HIV-1 Nef fragment

<400> SEQUENCE: 104

Asp Leu Ser His Phe Leu Lys Glu Lys Gly Gly Leu Glu Gly Leu Ile
1               5                   10                  15

His Ser Gln Arg Arg Gln Asp Ile Leu Asp Leu Trp Ile
            20                  25

<210> SEQ ID NO 105
<211> LENGTH: 28
<212> TYPE: PRT
<213> ORGANISM: Artificial sequence
<220> FEATURE:
<223> OTHER INFORMATION: 87-114 HIV-1 Nef fragment

<400> SEQUENCE: 105

Leu Ser His Phe Leu Lys Glu Lys Gly Gly Leu Glu Gly Leu Ile His
1               5                   10                  15

Ser Gln Arg Arg Gln Asp Ile Leu Asp Leu Trp Ile
            20                  25

<210> SEQ ID NO 106
<211> LENGTH: 27
<212> TYPE: PRT
<213> ORGANISM: Artificial sequence
<220> FEATURE:
<223> OTHER INFORMATION: 88-114 HIV-1 Nef fragment

<400> SEQUENCE: 106

Ser His Phe Leu Lys Glu Lys Gly Gly Leu Glu Gly Leu Ile His Ser
1               5                   10                  15

Gln Arg Arg Gln Asp Ile Leu Asp Leu Trp Ile
            20                  25

<210> SEQ ID NO 107
<211> LENGTH: 26
<212> TYPE: PRT
<213> ORGANISM: Artificial sequence
<220> FEATURE:
<223> OTHER INFORMATION: 89-114 HIV-1 Nef fragment

<400> SEQUENCE: 107

His Phe Leu Lys Glu Lys Gly Gly Leu Glu Gly Leu Ile His Ser Gln
1               5                   10                  15

Arg Arg Gln Asp Ile Leu Asp Leu Trp Ile
            20                  25

<210> SEQ ID NO 108
<211> LENGTH: 25
<212> TYPE: PRT

<213> ORGANISM: Artificial sequence
<220> FEATURE:
<223> OTHER INFORMATION: 90-114 HIV-1 Nef fragment

<400> SEQUENCE: 108

Phe Leu Lys Glu Lys Gly Gly Leu Glu Gly Leu Ile His Ser Gln Arg
1               5                   10                  15

Arg Gln Asp Ile Leu Asp Leu Trp Ile
            20                  25

<210> SEQ ID NO 109
<211> LENGTH: 34
<212> TYPE: PRT
<213> ORGANISM: Artificial sequence
<220> FEATURE:
<223> OTHER INFORMATION: 80-113 HIV-1 Nef fragment

<400> SEQUENCE: 109

Thr Tyr Lys Ala Ala Val Asp Leu Ser His Phe Leu Lys Glu Lys Gly
1               5                   10                  15

Gly Leu Glu Gly Leu Ile His Ser Gln Arg Arg Gln Asp Ile Leu Asp
            20                  25                  30

Leu Trp

<210> SEQ ID NO 110
<211> LENGTH: 33
<212> TYPE: PRT
<213> ORGANISM: Artificial sequence
<220> FEATURE:
<223> OTHER INFORMATION: 81-113 HIV-1 Nef fragment

<400> SEQUENCE: 110

Tyr Lys Ala Ala Val Asp Leu Ser His Phe Leu Lys Glu Lys Gly Gly
1               5                   10                  15

Leu Glu Gly Leu Ile His Ser Gln Arg Arg Gln Asp Ile Leu Asp Leu
            20                  25                  30

Trp

<210> SEQ ID NO 111
<211> LENGTH: 32
<212> TYPE: PRT
<213> ORGANISM: Artificial sequence
<220> FEATURE:
<223> OTHER INFORMATION: 82-113 HIV-1 Nef fragment

<400> SEQUENCE: 111

Lys Ala Ala Val Asp Leu Ser His Phe Leu Lys Glu Lys Gly Gly Leu
1               5                   10                  15

Glu Gly Leu Ile His Ser Gln Arg Arg Gln Asp Ile Leu Asp Leu Trp
            20                  25                  30

<210> SEQ ID NO 112
<211> LENGTH: 31
<212> TYPE: PRT
<213> ORGANISM: Artificial sequence
<220> FEATURE:
<223> OTHER INFORMATION: 83-113 HIV-1 Nef fragment

<400> SEQUENCE: 112

Ala Ala Val Asp Leu Ser His Phe Leu Lys Glu Lys Gly Gly Leu Glu
1               5                   10                  15

Gly Leu Ile His Ser Gln Arg Arg Gln Asp Ile Leu Asp Leu Trp
            20                  25                  30

```
<210> SEQ ID NO 113
<211> LENGTH: 30
<212> TYPE: PRT
<213> ORGANISM: Artificial sequence
<220> FEATURE:
<223> OTHER INFORMATION: 84-113 HIV-1 Nef fragment

<400> SEQUENCE: 113

Ala Val Asp Leu Ser His Phe Leu Lys Glu Lys Gly Gly Leu Glu Gly
1               5                   10                  15

Leu Ile His Ser Gln Arg Arg Gln Asp Ile Leu Asp Leu Trp
            20                  25                  30

<210> SEQ ID NO 114
<211> LENGTH: 29
<212> TYPE: PRT
<213> ORGANISM: Artificial sequence
<220> FEATURE:
<223> OTHER INFORMATION: 85-113 HIV-1 Nef fragment

<400> SEQUENCE: 114

Val Asp Leu Ser His Phe Leu Lys Glu Lys Gly Gly Leu Glu Gly Leu
1               5                   10                  15

Ile His Ser Gln Arg Arg Gln Asp Ile Leu Asp Leu Trp
            20                  25

<210> SEQ ID NO 115
<211> LENGTH: 28
<212> TYPE: PRT
<213> ORGANISM: Artificial sequence
<220> FEATURE:
<223> OTHER INFORMATION: 86-113 HIV-1 Nef fragment

<400> SEQUENCE: 115

Asp Leu Ser His Phe Leu Lys Glu Lys Gly Gly Leu Glu Gly Leu Ile
1               5                   10                  15

His Ser Gln Arg Arg Gln Asp Ile Leu Asp Leu Trp
            20                  25

<210> SEQ ID NO 116
<211> LENGTH: 27
<212> TYPE: PRT
<213> ORGANISM: Artificial sequence
<220> FEATURE:
<223> OTHER INFORMATION: 87-113 HIV-1 Nef fragment

<400> SEQUENCE: 116

Leu Ser His Phe Leu Lys Glu Lys Gly Gly Leu Glu Gly Leu Ile His
1               5                   10                  15

Ser Gln Arg Arg Gln Asp Ile Leu Asp Leu Trp
            20                  25

<210> SEQ ID NO 117
<211> LENGTH: 26
<212> TYPE: PRT
<213> ORGANISM: Artificial sequence
<220> FEATURE:
<223> OTHER INFORMATION: 88-113 HIV-1 Nef fragment

<400> SEQUENCE: 117

Ser His Phe Leu Lys Glu Lys Gly Gly Leu Glu Gly Leu Ile His Ser
1               5                   10                  15

Gln Arg Arg Gln Asp Ile Leu Asp Leu Trp
```

<210> SEQ ID NO 118
<211> LENGTH: 25
<212> TYPE: PRT
<213> ORGANISM: Artificial sequence
<220> FEATURE:
<223> OTHER INFORMATION: 89-113 HIV-1 Nef fragment

<400> SEQUENCE: 118

His Phe Leu Lys Glu Lys Gly Gly Leu Glu Gly Leu Ile His Ser Gln
1               5                   10                  15

Arg Arg Gln Asp Ile Leu Asp Leu Trp
            20                  25

<210> SEQ ID NO 119
<211> LENGTH: 24
<212> TYPE: PRT
<213> ORGANISM: Artificial sequence
<220> FEATURE:
<223> OTHER INFORMATION: 90-113 HIV-1 Nef fragment

<400> SEQUENCE: 119

Phe Leu Lys Glu Lys Gly Gly Leu Glu Gly Leu Ile His Ser Gln Arg
1               5                   10                  15

Arg Gln Asp Ile Leu Asp Leu Trp
            20

<210> SEQ ID NO 120
<211> LENGTH: 33
<212> TYPE: PRT
<213> ORGANISM: Artificial sequence
<220> FEATURE:
<223> OTHER INFORMATION: 80-112 HIV-1 Nef fragment

<400> SEQUENCE: 120

Thr Tyr Lys Ala Ala Val Asp Leu Ser His Phe Leu Lys Glu Lys Gly
1               5                   10                  15

Gly Leu Glu Gly Leu Ile His Ser Gln Arg Arg Gln Asp Ile Leu Asp
            20                  25                  30

Leu

<210> SEQ ID NO 121
<211> LENGTH: 32
<212> TYPE: PRT
<213> ORGANISM: Artificial sequence
<220> FEATURE:
<223> OTHER INFORMATION: 81-112 HIV-1 Nef fragment

<400> SEQUENCE: 121

Tyr Lys Ala Ala Val Asp Leu Ser His Phe Leu Lys Glu Lys Gly Gly
1               5                   10                  15

Leu Glu Gly Leu Ile His Ser Gln Arg Arg Gln Asp Ile Leu Asp Leu
            20                  25                  30

<210> SEQ ID NO 122
<211> LENGTH: 31
<212> TYPE: PRT
<213> ORGANISM: Artificial sequence
<220> FEATURE:
<223> OTHER INFORMATION: 82-112 HIV-1 Nef fragment

<400> SEQUENCE: 122

Lys Ala Ala Val Asp Leu Ser His Phe Leu Lys Glu Lys Gly Gly Leu

```
                1               5                   10                  15
Glu Gly Leu Ile His Ser Gln Arg Arg Gln Asp Ile Leu Asp Leu
                20                  25                  30
```

<210> SEQ ID NO 123
<211> LENGTH: 30
<212> TYPE: PRT
<213> ORGANISM: Artificial sequence
<220> FEATURE:
<223> OTHER INFORMATION: 83-112 HIV-1 Nef fragment

<400> SEQUENCE: 123

```
Ala Ala Val Asp Leu Ser His Phe Leu Lys Glu Lys Gly Gly Leu Glu
1               5                   10                  15
Gly Leu Ile His Ser Gln Arg Arg Gln Asp Ile Leu Asp Leu
                20                  25                  30
```

<210> SEQ ID NO 124
<211> LENGTH: 29
<212> TYPE: PRT
<213> ORGANISM: Artificial sequence
<220> FEATURE:
<223> OTHER INFORMATION: 84-112 HIV-1 Nef fragment

<400> SEQUENCE: 124

```
Ala Val Asp Leu Ser His Phe Leu Lys Glu Lys Gly Gly Leu Glu Gly
1               5                   10                  15
Leu Ile His Ser Gln Arg Arg Gln Asp Ile Leu Asp Leu
                20                  25
```

<210> SEQ ID NO 125
<211> LENGTH: 28
<212> TYPE: PRT
<213> ORGANISM: Artificial sequence
<220> FEATURE:
<223> OTHER INFORMATION: 85-112 HIV-1 Nef fragment

<400> SEQUENCE: 125

```
Val Asp Leu Ser His Phe Leu Lys Glu Lys Gly Gly Leu Glu Gly Leu
1               5                   10                  15
Ile His Ser Gln Arg Arg Gln Asp Ile Leu Asp Leu
                20                  25
```

<210> SEQ ID NO 126
<211> LENGTH: 27
<212> TYPE: PRT
<213> ORGANISM: Artificial sequence
<220> FEATURE:
<223> OTHER INFORMATION: 86-112 HIV-1 Nef fragment

<400> SEQUENCE: 126

```
Asp Leu Ser His Phe Leu Lys Glu Lys Gly Gly Leu Glu Gly Leu Ile
1               5                   10                  15
His Ser Gln Arg Arg Gln Asp Ile Leu Asp Leu
                20                  25
```

<210> SEQ ID NO 127
<211> LENGTH: 26
<212> TYPE: PRT
<213> ORGANISM: Artificial sequence
<220> FEATURE:
<223> OTHER INFORMATION: 87-112 HIV-1 Nef fragment

<400> SEQUENCE: 127

```
Leu Ser His Phe Leu Lys Glu Lys Gly Gly Leu Glu Gly Leu Ile His
1               5                   10                  15

Ser Gln Arg Arg Gln Asp Ile Leu Asp Leu
            20                  25
```

<210> SEQ ID NO 128
<211> LENGTH: 25
<212> TYPE: PRT
<213> ORGANISM: Artificial sequence
<220> FEATURE:
<223> OTHER INFORMATION: 88-112 HIV-1 Nef fragment

<400> SEQUENCE: 128

```
Ser His Phe Leu Lys Glu Lys Gly Gly Leu Glu Gly Leu Ile His Ser
1               5                   10                  15

Gln Arg Arg Gln Asp Ile Leu Asp Leu
            20                  25
```

<210> SEQ ID NO 129
<211> LENGTH: 24
<212> TYPE: PRT
<213> ORGANISM: Artificial sequence
<220> FEATURE:
<223> OTHER INFORMATION: 89-112 HIV-1 Nef fragment

<400> SEQUENCE: 129

```
His Phe Leu Lys Glu Lys Gly Gly Leu Glu Gly Leu Ile His Ser Gln
1               5                   10                  15

Arg Arg Gln Asp Ile Leu Asp Leu
            20
```

<210> SEQ ID NO 130
<211> LENGTH: 23
<212> TYPE: PRT
<213> ORGANISM: Artificial sequence
<220> FEATURE:
<223> OTHER INFORMATION: 90-112 HIV-1 Nef fragment

<400> SEQUENCE: 130

```
Phe Leu Lys Glu Lys Gly Gly Leu Glu Gly Leu Ile His Ser Gln Arg
1               5                   10                  15

Arg Gln Asp Ile Leu Asp Leu
            20
```

<210> SEQ ID NO 131
<211> LENGTH: 47
<212> TYPE: PRT
<213> ORGANISM: Artificial sequence
<220> FEATURE:
<223> OTHER INFORMATION: 104-150 HIV-2 Nef fragment

<400> SEQUENCE: 131

```
Arg Val Pro Leu Arg Glu Met Thr Tyr Arg Leu Ala Arg Asp Met Ser
1               5                   10                  15

His Leu Ile Lys Glu Lys Gly Gly Leu Glu Gly Leu Tyr Tyr Ser Asp
                20                  25                  30

Arg Arg Arg Arg Val Leu Asp Ile Tyr Leu Glu Lys Glu Glu Gly
            35                  40                  45
```

<210> SEQ ID NO 132
<211> LENGTH: 46
<212> TYPE: PRT
<213> ORGANISM: Artificial sequence
<220> FEATURE:

```
<223> OTHER INFORMATION: 105-150 HIV-2 Nef fragment

<400> SEQUENCE: 132

Val Pro Leu Arg Glu Met Thr Tyr Arg Leu Ala Arg Asp Met Ser His
1               5                   10                  15
Leu Ile Lys Glu Lys Gly Gly Leu Glu Gly Leu Tyr Tyr Ser Asp Arg
            20                  25                  30
Arg Arg Arg Val Leu Asp Ile Tyr Leu Glu Lys Glu Glu Gly
        35                  40                  45

<210> SEQ ID NO 133
<211> LENGTH: 45
<212> TYPE: PRT
<213> ORGANISM: Artificial sequence
<220> FEATURE:
<223> OTHER INFORMATION: 106-150 HIV-2 Nef fragment

<400> SEQUENCE: 133

Pro Leu Arg Glu Met Thr Tyr Arg Leu Ala Arg Asp Met Ser His Leu
1               5                   10                  15
Ile Lys Glu Lys Gly Gly Leu Glu Gly Leu Tyr Tyr Ser Asp Arg Arg
            20                  25                  30
Arg Arg Val Leu Asp Ile Tyr Leu Glu Lys Glu Glu Gly
        35                  40                  45

<210> SEQ ID NO 134
<211> LENGTH: 44
<212> TYPE: PRT
<213> ORGANISM: Artificial sequence
<220> FEATURE:
<223> OTHER INFORMATION: 107-150 HIV-2 Nef fragment

<400> SEQUENCE: 134

Leu Arg Glu Met Thr Tyr Arg Leu Ala Arg Asp Met Ser His Leu Ile
1               5                   10                  15
Lys Glu Lys Gly Gly Leu Glu Gly Leu Tyr Tyr Ser Asp Arg Arg Arg
            20                  25                  30
Arg Val Leu Asp Ile Tyr Leu Glu Lys Glu Glu Gly
        35                  40

<210> SEQ ID NO 135
<211> LENGTH: 43
<212> TYPE: PRT
<213> ORGANISM: Artificial sequence
<220> FEATURE:
<223> OTHER INFORMATION: 108-150 HIV-2 Nef fragment

<400> SEQUENCE: 135

Arg Glu Met Thr Tyr Arg Leu Ala Arg Asp Met Ser His Leu Ile Lys
1               5                   10                  15
Glu Lys Gly Gly Leu Glu Gly Leu Tyr Tyr Ser Asp Arg Arg Arg Arg
            20                  25                  30
Val Leu Asp Ile Tyr Leu Glu Lys Glu Glu Gly
        35                  40

<210> SEQ ID NO 136
<211> LENGTH: 42
<212> TYPE: PRT
<213> ORGANISM: Artificial sequence
<220> FEATURE:
<223> OTHER INFORMATION: 109-150 HIV-2 Nef fragment

<400> SEQUENCE: 136
```

```
Glu Met Thr Tyr Arg Leu Ala Arg Asp Met Ser His Leu Ile Lys Glu
1               5                   10                  15

Lys Gly Gly Leu Glu Gly Leu Tyr Tyr Ser Asp Arg Arg Arg Arg Val
            20                  25                  30

Leu Asp Ile Tyr Leu Glu Lys Glu Glu Gly
        35                  40

<210> SEQ ID NO 137
<211> LENGTH: 41
<212> TYPE: PRT
<213> ORGANISM: Artificial sequence
<220> FEATURE:
<223> OTHER INFORMATION: 110-150 HIV-2 Nef fragment

<400> SEQUENCE: 137

Met Thr Tyr Arg Leu Ala Arg Asp Met Ser His Leu Ile Lys Glu Lys
1               5                   10                  15

Gly Gly Leu Glu Gly Leu Tyr Tyr Ser Asp Arg Arg Arg Arg Val Leu
            20                  25                  30

Asp Ile Tyr Leu Glu Lys Glu Glu Gly
        35                  40

<210> SEQ ID NO 138
<211> LENGTH: 40
<212> TYPE: PRT
<213> ORGANISM: Artificial sequence
<220> FEATURE:
<223> OTHER INFORMATION: 111-150 HIV-2 Nef fragment

<400> SEQUENCE: 138

Thr Tyr Arg Leu Ala Arg Asp Met Ser His Leu Ile Lys Glu Lys Gly
1               5                   10                  15

Gly Leu Glu Gly Leu Tyr Tyr Ser Asp Arg Arg Arg Arg Val Leu Asp
            20                  25                  30

Ile Tyr Leu Glu Lys Glu Glu Gly
        35                  40

<210> SEQ ID NO 139
<211> LENGTH: 39
<212> TYPE: PRT
<213> ORGANISM: Artificial sequence
<220> FEATURE:
<223> OTHER INFORMATION: 112-150 HIV-2 Nef fragment

<400> SEQUENCE: 139

Tyr Arg Leu Ala Arg Asp Met Ser His Leu Ile Lys Glu Lys Gly Gly
1               5                   10                  15

Leu Glu Gly Leu Tyr Tyr Ser Asp Arg Arg Arg Arg Val Leu Asp Ile
            20                  25                  30

Tyr Leu Glu Lys Glu Glu Gly
        35

<210> SEQ ID NO 140
<211> LENGTH: 38
<212> TYPE: PRT
<213> ORGANISM: Artificial sequence
<220> FEATURE:
<223> OTHER INFORMATION: 113-150 HIV-2 Nef fragment

<400> SEQUENCE: 140

Arg Leu Ala Arg Asp Met Ser His Leu Ile Lys Glu Lys Gly Gly Leu
1               5                   10                  15
```

-continued

Glu Gly Leu Tyr Tyr Ser Asp Arg Arg Arg Val Leu Asp Ile Tyr
            20                  25                  30

Leu Glu Lys Glu Glu Gly
        35

<210> SEQ ID NO 141
<211> LENGTH: 37
<212> TYPE: PRT
<213> ORGANISM: Artificial sequence
<220> FEATURE:
<223> OTHER INFORMATION: 114-150 HIV-2 Nef fragment

<400> SEQUENCE: 141

Leu Ala Arg Asp Met Ser His Leu Ile Lys Glu Lys Gly Gly Leu Glu
1               5                   10                  15

Gly Leu Tyr Tyr Ser Asp Arg Arg Arg Val Leu Asp Ile Tyr Leu
            20                  25                  30

Glu Lys Glu Glu Gly
        35

<210> SEQ ID NO 142
<211> LENGTH: 36
<212> TYPE: PRT
<213> ORGANISM: Artificial sequence
<220> FEATURE:
<223> OTHER INFORMATION: 115-150 HIV-2 Nef fragment

<400> SEQUENCE: 142

Ala Arg Asp Met Ser His Leu Ile Lys Glu Lys Gly Gly Leu Glu Gly
1               5                   10                  15

Leu Tyr Tyr Ser Asp Arg Arg Arg Val Leu Asp Ile Tyr Leu Glu
            20                  25                  30

Lys Glu Glu Gly
        35

<210> SEQ ID NO 143
<211> LENGTH: 35
<212> TYPE: PRT
<213> ORGANISM: Artificial sequence
<220> FEATURE:
<223> OTHER INFORMATION: 116-150 HIV-2 Nef fragment

<400> SEQUENCE: 143

Arg Asp Met Ser His Leu Ile Lys Glu Lys Gly Gly Leu Glu Gly Leu
1               5                   10                  15

Tyr Tyr Ser Asp Arg Arg Arg Val Leu Asp Ile Tyr Leu Glu Lys
            20                  25                  30

Glu Glu Gly
        35

<210> SEQ ID NO 144
<211> LENGTH: 34
<212> TYPE: PRT
<213> ORGANISM: Artificial sequence
<220> FEATURE:
<223> OTHER INFORMATION: 117-150 HIV-2 Nef fragment

<400> SEQUENCE: 144

Asp Met Ser His Leu Ile Lys Glu Lys Gly Gly Leu Glu Gly Leu Tyr
1               5                   10                  15

Tyr Ser Asp Arg Arg Arg Arg Val Leu Asp Ile Tyr Leu Glu Lys Glu
            20                  25                  30

Glu Gly

<210> SEQ ID NO 145
<211> LENGTH: 33
<212> TYPE: PRT
<213> ORGANISM: Artificial sequence
<220> FEATURE:
<223> OTHER INFORMATION: 118-150 HIV-2 Nef frgament

<400> SEQUENCE: 145

Met Ser His Leu Ile Lys Glu Lys Gly Gly Leu Glu Gly Leu Tyr Tyr
1               5                   10                  15

Ser Asp Arg Arg Arg Val Leu Asp Ile Tyr Leu Glu Lys Glu Glu
            20                  25                  30

Gly

<210> SEQ ID NO 146
<211> LENGTH: 32
<212> TYPE: PRT
<213> ORGANISM: Artificial sequence
<220> FEATURE:
<223> OTHER INFORMATION: 119-150 HIV-2 Nef fragment

<400> SEQUENCE: 146

Ser His Leu Ile Lys Glu Lys Gly Gly Leu Glu Gly Leu Tyr Tyr Ser
1               5                   10                  15

Asp Arg Arg Arg Arg Val Leu Asp Ile Tyr Leu Glu Lys Glu Glu Gly
            20                  25                  30

<210> SEQ ID NO 147
<211> LENGTH: 31
<212> TYPE: PRT
<213> ORGANISM: Artificial sequence
<220> FEATURE:
<223> OTHER INFORMATION: 120-150 HIV-2 Nef fragment

<400> SEQUENCE: 147

His Leu Ile Lys Glu Lys Gly Gly Leu Glu Gly Leu Tyr Tyr Ser Asp
1               5                   10                  15

Arg Arg Arg Arg Val Leu Asp Ile Tyr Leu Glu Lys Glu Glu Gly
            20                  25                  30

<210> SEQ ID NO 148
<211> LENGTH: 30
<212> TYPE: PRT
<213> ORGANISM: Artificial sequence
<220> FEATURE:
<223> OTHER INFORMATION: 121-150 HIV-2 Nef fragment

<400> SEQUENCE: 148

Leu Ile Lys Glu Lys Gly Gly Leu Glu Gly Leu Tyr Tyr Ser Asp Arg
1               5                   10                  15

Arg Arg Arg Val Leu Asp Ile Tyr Leu Glu Lys Glu Glu Gly
            20                  25                  30

<210> SEQ ID NO 149
<211> LENGTH: 46
<212> TYPE: PRT
<213> ORGANISM: Artificial sequence
<220> FEATURE:
<223> OTHER INFORMATION: 104-149 HIV-2 Nef fragment

<400> SEQUENCE: 149

Arg Val Pro Leu Arg Glu Met Thr Tyr Arg Leu Ala Arg Asp Met Ser
1               5                   10                  15

His Leu Ile Lys Glu Lys Gly Gly Leu Glu Gly Leu Tyr Tyr Ser Asp
            20                  25                  30

Arg Arg Arg Arg Val Leu Asp Ile Tyr Leu Glu Lys Glu Glu
        35                  40                  45

<210> SEQ ID NO 150
<211> LENGTH: 45
<212> TYPE: PRT
<213> ORGANISM: Artificial sequence
<220> FEATURE:
<223> OTHER INFORMATION: 105-149 HIV-2 Nef fragment

<400> SEQUENCE: 150

Val Pro Leu Arg Glu Met Thr Tyr Arg Leu Ala Arg Asp Met Ser His
1               5                   10                  15

Leu Ile Lys Glu Lys Gly Gly Leu Glu Gly Leu Tyr Tyr Ser Asp Arg
            20                  25                  30

Arg Arg Arg Val Leu Asp Ile Tyr Leu Glu Lys Glu Glu
        35                  40                  45

<210> SEQ ID NO 151
<211> LENGTH: 44
<212> TYPE: PRT
<213> ORGANISM: Artificial sequence
<220> FEATURE:
<223> OTHER INFORMATION: 106-149 HIV-2 Nef fragment

<400> SEQUENCE: 151

Pro Leu Arg Glu Met Thr Tyr Arg Leu Ala Arg Asp Met Ser His Leu
1               5                   10                  15

Ile Lys Glu Lys Gly Gly Leu Glu Gly Leu Tyr Tyr Ser Asp Arg Arg
            20                  25                  30

Arg Arg Val Leu Asp Ile Tyr Leu Glu Lys Glu Glu
        35                  40

<210> SEQ ID NO 152
<211> LENGTH: 43
<212> TYPE: PRT
<213> ORGANISM: Artificial sequence
<220> FEATURE:
<223> OTHER INFORMATION: 107-149 HIV-2 Nef fragment

<400> SEQUENCE: 152

Leu Arg Glu Met Thr Tyr Arg Leu Ala Arg Asp Met Ser His Leu Ile
1               5                   10                  15

Lys Glu Lys Gly Gly Leu Glu Gly Leu Tyr Tyr Ser Asp Arg Arg Arg
            20                  25                  30

Arg Val Leu Asp Ile Tyr Leu Glu Lys Glu Glu
        35                  40

<210> SEQ ID NO 153
<211> LENGTH: 42
<212> TYPE: PRT
<213> ORGANISM: Artificial sequence
<220> FEATURE:
<223> OTHER INFORMATION: 108-149 HIV-2 Nef fragment

<400> SEQUENCE: 153

Arg Glu Met Thr Tyr Arg Leu Ala Arg Asp Met Ser His Leu Ile Lys
1               5                   10                  15

Glu Lys Gly Gly Leu Glu Gly Leu Tyr Tyr Ser Asp Arg Arg Arg
            20                  25                  30

Val Leu Asp Ile Tyr Leu Glu Lys Glu Glu
        35                  40

<210> SEQ ID NO 154
<211> LENGTH: 41
<212> TYPE: PRT
<213> ORGANISM: Artificial sequence
<220> FEATURE:
<223> OTHER INFORMATION: 109-149 HIV-2 Nef fragment

<400> SEQUENCE: 154

Glu Met Thr Tyr Arg Leu Ala Arg Asp Met Ser His Leu Ile Lys Glu
1               5                   10                  15

Lys Gly Gly Leu Glu Gly Leu Tyr Tyr Ser Asp Arg Arg Arg Arg Val
            20                  25                  30

Leu Asp Ile Tyr Leu Glu Lys Glu Glu
        35                  40

<210> SEQ ID NO 155
<211> LENGTH: 40
<212> TYPE: PRT
<213> ORGANISM: Artificial sequence
<220> FEATURE:
<223> OTHER INFORMATION: 110-149 HIV-2 Nef fragment

<400> SEQUENCE: 155

Met Thr Tyr Arg Leu Ala Arg Asp Met Ser His Leu Ile Lys Glu Lys
1               5                   10                  15

Gly Gly Leu Glu Gly Leu Tyr Tyr Ser Asp Arg Arg Arg Arg Val Leu
            20                  25                  30

Asp Ile Tyr Leu Glu Lys Glu Glu
        35                  40

<210> SEQ ID NO 156
<211> LENGTH: 39
<212> TYPE: PRT
<213> ORGANISM: Artificial sequence
<220> FEATURE:
<223> OTHER INFORMATION: 111-149 HIV-2 Nef fragment

<400> SEQUENCE: 156

Thr Tyr Arg Leu Ala Arg Asp Met Ser His Leu Ile Lys Glu Lys Gly
1               5                   10                  15

Gly Leu Glu Gly Leu Tyr Tyr Ser Asp Arg Arg Arg Arg Val Leu Asp
            20                  25                  30

Ile Tyr Leu Glu Lys Glu Glu
        35

<210> SEQ ID NO 157
<211> LENGTH: 38
<212> TYPE: PRT
<213> ORGANISM: Artificial sequence
<220> FEATURE:
<223> OTHER INFORMATION: 112-149 HIV-2 Nef fragment

<400> SEQUENCE: 157

Tyr Arg Leu Ala Arg Asp Met Ser His Leu Ile Lys Glu Lys Gly Gly
1               5                   10                  15

Leu Glu Gly Leu Tyr Tyr Ser Asp Arg Arg Arg Arg Val Leu Asp Ile
            20                  25                  30

```
-continued

Tyr Leu Glu Lys Glu Glu
        35

<210> SEQ ID NO 158
<211> LENGTH: 37
<212> TYPE: PRT
<213> ORGANISM: Artificial sequence
<220> FEATURE:
<223> OTHER INFORMATION: 113-149 HIV-2 Nef fragment

<400> SEQUENCE: 158

Arg Leu Ala Arg Asp Met Ser His Leu Ile Lys Glu Lys Gly Gly Leu
1               5                   10                  15

Glu Gly Leu Tyr Tyr Ser Asp Arg Arg Arg Val Leu Asp Ile Tyr
            20                  25                  30

Leu Glu Lys Glu Glu
        35

<210> SEQ ID NO 159
<211> LENGTH: 36
<212> TYPE: PRT
<213> ORGANISM: Artificial sequence
<220> FEATURE:
<223> OTHER INFORMATION: 114-149 HIV-2 Nef fragment

<400> SEQUENCE: 159

Leu Ala Arg Asp Met Ser His Leu Ile Lys Glu Lys Gly Gly Leu Glu
1               5                   10                  15

Gly Leu Tyr Tyr Ser Asp Arg Arg Arg Val Leu Asp Ile Tyr Leu
            20                  25                  30

Glu Lys Glu Glu
        35

<210> SEQ ID NO 160
<211> LENGTH: 35
<212> TYPE: PRT
<213> ORGANISM: Artificial sequence
<220> FEATURE:
<223> OTHER INFORMATION: 115-149 HIV-2 Nef fragment

<400> SEQUENCE: 160

Ala Arg Asp Met Ser His Leu Ile Lys Glu Lys Gly Gly Leu Glu Gly
1               5                   10                  15

Leu Tyr Tyr Ser Asp Arg Arg Arg Val Leu Asp Ile Tyr Leu Glu
            20                  25                  30

Lys Glu Glu
        35

<210> SEQ ID NO 161
<211> LENGTH: 34
<212> TYPE: PRT
<213> ORGANISM: Artificial sequence
<220> FEATURE:
<223> OTHER INFORMATION: 116-149 HIV-2 Nef fragment

<400> SEQUENCE: 161

Arg Asp Met Ser His Leu Ile Lys Glu Lys Gly Gly Leu Glu Gly Leu
1               5                   10                  15

Tyr Tyr Ser Asp Arg Arg Arg Val Leu Asp Ile Tyr Leu Glu Lys
            20                  25                  30

Glu Glu
```

```
<210> SEQ ID NO 162
<211> LENGTH: 33
<212> TYPE: PRT
<213> ORGANISM: Artificial sequence
<220> FEATURE:
<223> OTHER INFORMATION: 117-149 HIV-2 Nef fragment

<400> SEQUENCE: 162
```

Asp Met Ser His Leu Ile Lys Glu Lys Gly Gly Leu Glu Gly Leu Tyr
1               5                   10                  15

Tyr Ser Asp Arg Arg Arg Arg Val Leu Asp Ile Tyr Leu Glu Lys Glu
            20                  25                  30

Glu

```
<210> SEQ ID NO 163
<211> LENGTH: 32
<212> TYPE: PRT
<213> ORGANISM: Artificial sequence
<220> FEATURE:
<223> OTHER INFORMATION: 118-149 HIV-2 Nef fragment

<400> SEQUENCE: 163
```

Met Ser His Leu Ile Lys Glu Lys Gly Gly Leu Glu Gly Leu Tyr Tyr
1               5                   10                  15

Ser Asp Arg Arg Arg Arg Val Leu Asp Ile Tyr Leu Glu Lys Glu Glu
            20                  25                  30

```
<210> SEQ ID NO 164
<211> LENGTH: 31
<212> TYPE: PRT
<213> ORGANISM: Artificial sequence
<220> FEATURE:
<223> OTHER INFORMATION: 119-149 HIV-2 Nef fragment

<400> SEQUENCE: 164
```

Ser His Leu Ile Lys Glu Lys Gly Gly Leu Glu Gly Leu Tyr Tyr Ser
1               5                   10                  15

Asp Arg Arg Arg Arg Val Leu Asp Ile Tyr Leu Glu Lys Glu Glu
            20                  25                  30

```
<210> SEQ ID NO 165
<211> LENGTH: 30
<212> TYPE: PRT
<213> ORGANISM: Artificial sequence
<220> FEATURE:
<223> OTHER INFORMATION: 120-149 HIV-2 Nef fragment

<400> SEQUENCE: 165
```

His Leu Ile Lys Glu Lys Gly Gly Leu Glu Gly Leu Tyr Tyr Ser Asp
1               5                   10                  15

Arg Arg Arg Arg Val Leu Asp Ile Tyr Leu Glu Lys Glu Glu
            20                  25                  30

```
<210> SEQ ID NO 166
<211> LENGTH: 29
<212> TYPE: PRT
<213> ORGANISM: Artificial sequence
<220> FEATURE:
<223> OTHER INFORMATION: 121-149 HIV-2 Nef fragment

<400> SEQUENCE: 166
```

Leu Ile Lys Glu Lys Gly Gly Leu Glu Gly Leu Tyr Tyr Ser Asp Arg
1               5                   10                  15

Arg Arg Arg Val Leu Asp Ile Tyr Leu Glu Lys Glu Glu

```
                20                  25

<210> SEQ ID NO 167
<211> LENGTH: 45
<212> TYPE: PRT
<213> ORGANISM: Artificial sequence
<220> FEATURE:
<223> OTHER INFORMATION: 104-148 HIV-2 Nef fragment

<400> SEQUENCE: 167

Arg Val Pro Leu Arg Glu Met Thr Tyr Arg Leu Ala Arg Asp Met Ser
1               5                   10                  15

His Leu Ile Lys Glu Lys Gly Gly Leu Glu Gly Leu Tyr Tyr Ser Asp
            20                  25                  30

Arg Arg Arg Arg Val Leu Asp Ile Tyr Leu Glu Lys Glu
        35                  40                  45

<210> SEQ ID NO 168
<211> LENGTH: 44
<212> TYPE: PRT
<213> ORGANISM: Artificial sequence
<220> FEATURE:
<223> OTHER INFORMATION: 105-148 HIV-2 Nef fragment

<400> SEQUENCE: 168

Val Pro Leu Arg Glu Met Thr Tyr Arg Leu Ala Arg Asp Met Ser His
1               5                   10                  15

Leu Ile Lys Glu Lys Gly Gly Leu Glu Gly Leu Tyr Tyr Ser Asp Arg
            20                  25                  30

Arg Arg Arg Val Leu Asp Ile Tyr Leu Glu Lys Glu
        35                  40

<210> SEQ ID NO 169
<211> LENGTH: 43
<212> TYPE: PRT
<213> ORGANISM: Artificial sequence
<220> FEATURE:
<223> OTHER INFORMATION: 106-148 HIV-2 Nef fragment

<400> SEQUENCE: 169

Pro Leu Arg Glu Met Thr Tyr Arg Leu Ala Arg Asp Met Ser His Leu
1               5                   10                  15

Ile Lys Glu Lys Gly Gly Leu Glu Gly Leu Tyr Tyr Ser Asp Arg Arg
            20                  25                  30

Arg Arg Val Leu Asp Ile Tyr Leu Glu Lys Glu
        35                  40

<210> SEQ ID NO 170
<211> LENGTH: 42
<212> TYPE: PRT
<213> ORGANISM: Artificial sequence
<220> FEATURE:
<223> OTHER INFORMATION: 107-148 HIV-2 Nef fragment

<400> SEQUENCE: 170

Leu Arg Glu Met Thr Tyr Arg Leu Ala Arg Asp Met Ser His Leu Ile
1               5                   10                  15

Lys Glu Lys Gly Gly Leu Glu Gly Leu Tyr Tyr Ser Asp Arg Arg Arg
            20                  25                  30

Arg Val Leu Asp Ile Tyr Leu Glu Lys Glu
        35                  40
```

```
<210> SEQ ID NO 171
<211> LENGTH: 41
<212> TYPE: PRT
<213> ORGANISM: Artificial sequence
<220> FEATURE:
<223> OTHER INFORMATION: 108-148 HIV-2 Nef fragment

<400> SEQUENCE: 171

Arg Glu Met Thr Tyr Arg Leu Ala Arg Asp Met Ser His Leu Ile Lys
1               5                   10                  15
Glu Lys Gly Gly Leu Glu Gly Leu Tyr Tyr Ser Asp Arg Arg Arg Arg
            20                  25                  30
Val Leu Asp Ile Tyr Leu Glu Lys Glu
        35                  40

<210> SEQ ID NO 172
<211> LENGTH: 40
<212> TYPE: PRT
<213> ORGANISM: Artificial sequence
<220> FEATURE:
<223> OTHER INFORMATION: 109-148 HIV-2 Nef fragment

<400> SEQUENCE: 172

Glu Met Thr Tyr Arg Leu Ala Arg Asp Met Ser His Leu Ile Lys Glu
1               5                   10                  15
Lys Gly Gly Leu Glu Gly Leu Tyr Tyr Ser Asp Arg Arg Arg Arg Val
            20                  25                  30
Leu Asp Ile Tyr Leu Glu Lys Glu
        35                  40

<210> SEQ ID NO 173
<211> LENGTH: 39
<212> TYPE: PRT
<213> ORGANISM: Artificial sequence
<220> FEATURE:
<223> OTHER INFORMATION: 110-148 HIV-2 Nef fragment

<400> SEQUENCE: 173

Met Thr Tyr Arg Leu Ala Arg Asp Met Ser His Leu Ile Lys Glu Lys
1               5                   10                  15
Gly Gly Leu Glu Gly Leu Tyr Tyr Ser Asp Arg Arg Arg Arg Val Leu
            20                  25                  30
Asp Ile Tyr Leu Glu Lys Glu
        35

<210> SEQ ID NO 174
<211> LENGTH: 38
<212> TYPE: PRT
<213> ORGANISM: Artificial sequence
<220> FEATURE:
<223> OTHER INFORMATION: 111-148 HIV-2 Nef fragment

<400> SEQUENCE: 174

Thr Tyr Arg Leu Ala Arg Asp Met Ser His Leu Ile Lys Glu Lys Gly
1               5                   10                  15
Gly Leu Glu Gly Leu Tyr Tyr Ser Asp Arg Arg Arg Arg Val Leu Asp
            20                  25                  30
Ile Tyr Leu Glu Lys Glu
        35

<210> SEQ ID NO 175
<211> LENGTH: 37
<212> TYPE: PRT
```

<213> ORGANISM: Artificial sequence
<220> FEATURE:
<223> OTHER INFORMATION: 112-148 HIV-2 Nef fragment

<400> SEQUENCE: 175

Tyr Arg Leu Ala Arg Asp Met Ser His Leu Ile Lys Glu Lys Gly Gly
1               5                   10                  15

Leu Glu Gly Leu Tyr Tyr Ser Asp Arg Arg Arg Val Leu Asp Ile
            20                  25                  30

Tyr Leu Glu Lys Glu
        35

<210> SEQ ID NO 176
<211> LENGTH: 36
<212> TYPE: PRT
<213> ORGANISM: Artificial sequence
<220> FEATURE:
<223> OTHER INFORMATION: 113-148 HIV-2 Nef fragment

<400> SEQUENCE: 176

Arg Leu Ala Arg Asp Met Ser His Leu Ile Lys Glu Lys Gly Gly Leu
1               5                   10                  15

Glu Gly Leu Tyr Tyr Ser Asp Arg Arg Arg Val Leu Asp Ile Tyr
            20                  25                  30

Leu Glu Lys Glu
        35

<210> SEQ ID NO 177
<211> LENGTH: 35
<212> TYPE: PRT
<213> ORGANISM: Artificial sequence
<220> FEATURE:
<223> OTHER INFORMATION: 114-148 HIV-2 Nef fragment

<400> SEQUENCE: 177

Leu Ala Arg Asp Met Ser His Leu Ile Lys Glu Lys Gly Gly Leu Glu
1               5                   10                  15

Gly Leu Tyr Tyr Ser Asp Arg Arg Arg Val Leu Asp Ile Tyr Leu
            20                  25                  30

Glu Lys Glu
        35

<210> SEQ ID NO 178
<211> LENGTH: 34
<212> TYPE: PRT
<213> ORGANISM: Artificial sequence
<220> FEATURE:
<223> OTHER INFORMATION: 115-148 HIV-2 Nef fragment

<400> SEQUENCE: 178

Ala Arg Asp Met Ser His Leu Ile Lys Glu Lys Gly Gly Leu Glu Gly
1               5                   10                  15

Leu Tyr Tyr Ser Asp Arg Arg Arg Val Leu Asp Ile Tyr Leu Glu
            20                  25                  30

Lys Glu

<210> SEQ ID NO 179
<211> LENGTH: 33
<212> TYPE: PRT
<213> ORGANISM: Artificial sequence
<220> FEATURE:
<223> OTHER INFORMATION: 116-148 HIV-2 Nef fragment

<400> SEQUENCE: 179

Arg Asp Met Ser His Leu Ile Lys Glu Lys Gly Gly Leu Glu Gly Leu
1               5                   10                  15

Tyr Tyr Ser Asp Arg Arg Arg Val Leu Asp Ile Tyr Leu Glu Lys
            20                  25                  30

Glu

<210> SEQ ID NO 180
<211> LENGTH: 32
<212> TYPE: PRT
<213> ORGANISM: Artificial sequence
<220> FEATURE:
<223> OTHER INFORMATION: 117-148 HIV-2 Nef fragment

<400> SEQUENCE: 180

Asp Met Ser His Leu Ile Lys Glu Lys Gly Gly Leu Glu Gly Leu Tyr
1               5                   10                  15

Tyr Ser Asp Arg Arg Arg Arg Val Leu Asp Ile Tyr Leu Glu Lys Glu
            20                  25                  30

<210> SEQ ID NO 181
<211> LENGTH: 31
<212> TYPE: PRT
<213> ORGANISM: Artificial sequence
<220> FEATURE:
<223> OTHER INFORMATION: 118-148 HIV-2 Nef fragment

<400> SEQUENCE: 181

Met Ser His Leu Ile Lys Glu Lys Gly Gly Leu Glu Gly Leu Tyr Tyr
1               5                   10                  15

Ser Asp Arg Arg Arg Arg Val Leu Asp Ile Tyr Leu Glu Lys Glu
            20                  25                  30

<210> SEQ ID NO 182
<211> LENGTH: 30
<212> TYPE: PRT
<213> ORGANISM: Artificial sequence
<220> FEATURE:
<223> OTHER INFORMATION: 119-148 HIV-2 Nef fragment

<400> SEQUENCE: 182

Ser His Leu Ile Lys Glu Lys Gly Gly Leu Glu Gly Leu Tyr Tyr Ser
1               5                   10                  15

Asp Arg Arg Arg Arg Val Leu Asp Ile Tyr Leu Glu Lys Glu
            20                  25                  30

<210> SEQ ID NO 183
<211> LENGTH: 29
<212> TYPE: PRT
<213> ORGANISM: Artificial sequence
<220> FEATURE:
<223> OTHER INFORMATION: 120-148 HIV-2 Nef fragment

<400> SEQUENCE: 183

His Leu Ile Lys Glu Lys Gly Gly Leu Glu Gly Leu Tyr Tyr Ser Asp
1               5                   10                  15

Arg Arg Arg Arg Val Leu Asp Ile Tyr Leu Glu Lys Glu
            20                  25

<210> SEQ ID NO 184
<211> LENGTH: 28
<212> TYPE: PRT
<213> ORGANISM: Artificial sequence
<220> FEATURE:
<223> OTHER INFORMATION: 121-148 HIV-2 Nef fragment

<400> SEQUENCE: 184

Leu Ile Lys Glu Lys Gly Gly Leu Glu Gly Leu Tyr Tyr Ser Asp Arg
1               5                   10                  15

Arg Arg Arg Val Leu Asp Ile Tyr Leu Glu Lys Glu
            20                  25

<210> SEQ ID NO 185
<211> LENGTH: 44
<212> TYPE: PRT
<213> ORGANISM: Artificial sequence
<220> FEATURE:
<223> OTHER INFORMATION: 104-147 HIV-2 Nef fragment

<400> SEQUENCE: 185

Arg Val Pro Leu Arg Glu Met Thr Tyr Arg Leu Ala Arg Asp Met Ser
1               5                   10                  15

His Leu Ile Lys Glu Lys Gly Gly Leu Glu Gly Leu Tyr Tyr Ser Asp
            20                  25                  30

Arg Arg Arg Arg Val Leu Asp Ile Tyr Leu Glu Lys
        35                  40

<210> SEQ ID NO 186
<211> LENGTH: 43
<212> TYPE: PRT
<213> ORGANISM: Artificial sequence
<220> FEATURE:
<223> OTHER INFORMATION: 105-147 HIV-2 Nef fragment

<400> SEQUENCE: 186

Val Pro Leu Arg Glu Met Thr Tyr Arg Leu Ala Arg Asp Met Ser His
1               5                   10                  15

Leu Ile Lys Glu Lys Gly Gly Leu Glu Gly Leu Tyr Tyr Ser Asp Arg
            20                  25                  30

Arg Arg Arg Val Leu Asp Ile Tyr Leu Glu Lys
        35                  40

<210> SEQ ID NO 187
<211> LENGTH: 42
<212> TYPE: PRT
<213> ORGANISM: Artificial sequence
<220> FEATURE:
<223> OTHER INFORMATION: 106-147 HIV-2 Nef fragment

<400> SEQUENCE: 187

Pro Leu Arg Glu Met Thr Tyr Arg Leu Ala Arg Asp Met Ser His Leu
1               5                   10                  15

Ile Lys Glu Lys Gly Gly Leu Glu Gly Leu Tyr Tyr Ser Asp Arg Arg
            20                  25                  30

Arg Arg Val Leu Asp Ile Tyr Leu Glu Lys
        35                  40

<210> SEQ ID NO 188
<211> LENGTH: 41
<212> TYPE: PRT
<213> ORGANISM: Artificial sequence
<220> FEATURE:
<223> OTHER INFORMATION: 107-147 HIV-2 Nef fragment

<400> SEQUENCE: 188

Leu Arg Glu Met Thr Tyr Arg Leu Ala Arg Asp Met Ser His Leu Ile

```
  1               5                   10                  15
Lys Glu Lys Gly Gly Leu Glu Gly Leu Tyr Tyr Ser Asp Arg Arg Arg
            20                  25                  30

Arg Val Leu Asp Ile Tyr Leu Glu Lys
        35                  40

<210> SEQ ID NO 189
<211> LENGTH: 40
<212> TYPE: PRT
<213> ORGANISM: Artificial sequence
<220> FEATURE:
<223> OTHER INFORMATION: 108-147 HIV-2 Nef fragment

<400> SEQUENCE: 189

Arg Glu Met Thr Tyr Arg Leu Ala Arg Asp Met Ser His Leu Ile Lys
1               5                   10                  15

Glu Lys Gly Gly Leu Glu Gly Leu Tyr Tyr Ser Asp Arg Arg Arg Arg
            20                  25                  30

Val Leu Asp Ile Tyr Leu Glu Lys
        35                  40

<210> SEQ ID NO 190
<211> LENGTH: 39
<212> TYPE: PRT
<213> ORGANISM: Artificial sequence
<220> FEATURE:
<223> OTHER INFORMATION: 109-147 HIV-2 Nef fragment

<400> SEQUENCE: 190

Glu Met Thr Tyr Arg Leu Ala Arg Asp Met Ser His Leu Ile Lys Glu
1               5                   10                  15

Lys Gly Gly Leu Glu Gly Leu Tyr Tyr Ser Asp Arg Arg Arg Arg Val
            20                  25                  30

Leu Asp Ile Tyr Leu Glu Lys
        35

<210> SEQ ID NO 191
<211> LENGTH: 38
<212> TYPE: PRT
<213> ORGANISM: Artificial sequence
<220> FEATURE:
<223> OTHER INFORMATION: 110-147 HIV-2 Nef fragment

<400> SEQUENCE: 191

Met Thr Tyr Arg Leu Ala Arg Asp Met Ser His Leu Ile Lys Glu Lys
1               5                   10                  15

Gly Gly Leu Glu Gly Leu Tyr Tyr Ser Asp Arg Arg Arg Arg Val Leu
            20                  25                  30

Asp Ile Tyr Leu Glu Lys
        35

<210> SEQ ID NO 192
<211> LENGTH: 37
<212> TYPE: PRT
<213> ORGANISM: Artificial sequence
<220> FEATURE:
<223> OTHER INFORMATION: 111-147 HIV-2 Nef fragment

<400> SEQUENCE: 192

Thr Tyr Arg Leu Ala Arg Asp Met Ser His Leu Ile Lys Glu Lys Gly
1               5                   10                  15

Gly Leu Glu Gly Leu Tyr Tyr Ser Asp Arg Arg Arg Arg Val Leu Asp
```

```
                    20                  25                  30

Ile Tyr Leu Glu Lys
        35

<210> SEQ ID NO 193
<211> LENGTH: 36
<212> TYPE: PRT
<213> ORGANISM: Artificial sequence
<220> FEATURE:
<223> OTHER INFORMATION: 112-147 HIV-2 Nef fragment

<400> SEQUENCE: 193

Tyr Arg Leu Ala Arg Asp Met Ser His Leu Ile Lys Glu Lys Gly Gly
1               5                   10                  15

Leu Glu Gly Leu Tyr Tyr Ser Asp Arg Arg Arg Val Leu Asp Ile
            20                  25                  30

Tyr Leu Glu Lys
        35

<210> SEQ ID NO 194
<211> LENGTH: 35
<212> TYPE: PRT
<213> ORGANISM: Artificial sequence
<220> FEATURE:
<223> OTHER INFORMATION: 113-147 HIV-2 Nef fragment

<400> SEQUENCE: 194

Arg Leu Ala Arg Asp Met Ser His Leu Ile Lys Glu Lys Gly Gly Leu
1               5                   10                  15

Glu Gly Leu Tyr Tyr Ser Asp Arg Arg Arg Val Leu Asp Ile Tyr
            20                  25                  30

Leu Glu Lys
        35

<210> SEQ ID NO 195
<211> LENGTH: 34
<212> TYPE: PRT
<213> ORGANISM: Artificial sequence
<220> FEATURE:
<223> OTHER INFORMATION: 114-147 HIV-2 Nef fragment

<400> SEQUENCE: 195

Leu Ala Arg Asp Met Ser His Leu Ile Lys Glu Lys Gly Gly Leu Glu
1               5                   10                  15

Gly Leu Tyr Tyr Ser Asp Arg Arg Arg Val Leu Asp Ile Tyr Leu
            20                  25                  30

Glu Lys

<210> SEQ ID NO 196
<211> LENGTH: 33
<212> TYPE: PRT
<213> ORGANISM: Artificial sequence
<220> FEATURE:
<223> OTHER INFORMATION: 115-147 HIV-2 Nef fragment

<400> SEQUENCE: 196

Ala Arg Asp Met Ser His Leu Ile Lys Glu Lys Gly Gly Leu Glu Gly
1               5                   10                  15

Leu Tyr Tyr Ser Asp Arg Arg Arg Val Leu Asp Ile Tyr Leu Glu
            20                  25                  30

Lys
```

<210> SEQ ID NO 197
<211> LENGTH: 32
<212> TYPE: PRT
<213> ORGANISM: Artificial sequence
<220> FEATURE:
<223> OTHER INFORMATION: 116-147 HIV-2 Nef fragment

<400> SEQUENCE: 197

Arg Asp Met Ser His Leu Ile Lys Glu Lys Gly Gly Leu Glu Gly Leu
1               5                   10                  15

Tyr Tyr Ser Asp Arg Arg Arg Val Leu Asp Ile Tyr Leu Glu Lys
            20                  25                  30

<210> SEQ ID NO 198
<211> LENGTH: 31
<212> TYPE: PRT
<213> ORGANISM: Artificial sequence
<220> FEATURE:
<223> OTHER INFORMATION: 117-147 HIV-2 Nef fragment

<400> SEQUENCE: 198

Asp Met Ser His Leu Ile Lys Glu Lys Gly Gly Leu Glu Gly Leu Tyr
1               5                   10                  15

Tyr Ser Asp Arg Arg Arg Arg Val Leu Asp Ile Tyr Leu Glu Lys
            20                  25                  30

<210> SEQ ID NO 199
<211> LENGTH: 30
<212> TYPE: PRT
<213> ORGANISM: Artificial sequence
<220> FEATURE:
<223> OTHER INFORMATION: 118-147 HIV-2 Nef fragment

<400> SEQUENCE: 199

Met Ser His Leu Ile Lys Glu Lys Gly Gly Leu Glu Gly Leu Tyr Tyr
1               5                   10                  15

Ser Asp Arg Arg Arg Arg Val Leu Asp Ile Tyr Leu Glu Lys
            20                  25                  30

<210> SEQ ID NO 200
<211> LENGTH: 29
<212> TYPE: PRT
<213> ORGANISM: Artificial sequence
<220> FEATURE:
<223> OTHER INFORMATION: 119-147 HIV- Nef fragment

<400> SEQUENCE: 200

Ser His Leu Ile Lys Glu Lys Gly Gly Leu Glu Gly Leu Tyr Tyr Ser
1               5                   10                  15

Asp Arg Arg Arg Arg Val Leu Asp Ile Tyr Leu Glu Lys
            20                  25

<210> SEQ ID NO 201
<211> LENGTH: 28
<212> TYPE: PRT
<213> ORGANISM: Artificial sequence
<220> FEATURE:
<223> OTHER INFORMATION: 120-147 HIV-2 Nef fragment

<400> SEQUENCE: 201

His Leu Ile Lys Glu Lys Gly Gly Leu Glu Gly Leu Tyr Tyr Ser Asp
1               5                   10                  15

Arg Arg Arg Arg Val Leu Asp Ile Tyr Leu Glu Lys
            20                  25

<210> SEQ ID NO 202
<211> LENGTH: 27
<212> TYPE: PRT
<213> ORGANISM: Artificial sequence
<220> FEATURE:
<223> OTHER INFORMATION: 121-147 HIV-2 Nef fragment

<400> SEQUENCE: 202

```
Leu Ile Lys Glu Lys Gly Gly Leu Glu Gly Leu Tyr Tyr Ser Asp Arg
1               5                   10                  15

Arg Arg Arg Val Leu Asp Ile Tyr Leu Glu Lys
            20                  25
```

<210> SEQ ID NO 203
<211> LENGTH: 43
<212> TYPE: PRT
<213> ORGANISM: Artificial sequence
<220> FEATURE:
<223> OTHER INFORMATION: 104-146 HIV-2 Nef fragment

<400> SEQUENCE: 203

```
Arg Val Pro Leu Arg Glu Met Thr Tyr Arg Leu Ala Arg Asp Met Ser
1               5                   10                  15

His Leu Ile Lys Glu Lys Gly Gly Leu Glu Gly Leu Tyr Tyr Ser Asp
            20                  25                  30

Arg Arg Arg Arg Val Leu Asp Ile Tyr Leu Glu
        35                  40
```

<210> SEQ ID NO 204
<211> LENGTH: 42
<212> TYPE: PRT
<213> ORGANISM: Artificial sequence
<220> FEATURE:
<223> OTHER INFORMATION: 105-146 HIV-2 Nef fragment

<400> SEQUENCE: 204

```
Val Pro Leu Arg Glu Met Thr Tyr Arg Leu Ala Arg Asp Met Ser His
1               5                   10                  15

Leu Ile Lys Glu Lys Gly Gly Leu Glu Gly Leu Tyr Tyr Ser Asp Arg
            20                  25                  30

Arg Arg Arg Val Leu Asp Ile Tyr Leu Glu
        35                  40
```

<210> SEQ ID NO 205
<211> LENGTH: 41
<212> TYPE: PRT
<213> ORGANISM: Artificial sequence
<220> FEATURE:
<223> OTHER INFORMATION: 106-146 HIV-2 Nef fragment

<400> SEQUENCE: 205

```
Pro Leu Arg Glu Met Thr Tyr Arg Leu Ala Arg Asp Met Ser His Leu
1               5                   10                  15

Ile Lys Glu Lys Gly Gly Leu Glu Gly Leu Tyr Tyr Ser Asp Arg Arg
            20                  25                  30

Arg Arg Val Leu Asp Ile Tyr Leu Glu
        35                  40
```

<210> SEQ ID NO 206
<211> LENGTH: 40
<212> TYPE: PRT
<213> ORGANISM: Artificial sequence

```
<220> FEATURE:
<223> OTHER INFORMATION: 107-146 HIV-2 Nef fragment

<400> SEQUENCE: 206

Leu Arg Glu Met Thr Tyr Arg Leu Ala Arg Asp Met Ser His Leu Ile
1               5                   10                  15

Lys Glu Lys Gly Gly Leu Glu Gly Leu Tyr Tyr Ser Asp Arg Arg Arg
            20                  25                  30

Arg Val Leu Asp Ile Tyr Leu Glu
        35                  40

<210> SEQ ID NO 207
<211> LENGTH: 39
<212> TYPE: PRT
<213> ORGANISM: Artificial sequence
<220> FEATURE:
<223> OTHER INFORMATION: 108-146 HIV-2 Nef fragment

<400> SEQUENCE: 207

Arg Glu Met Thr Tyr Arg Leu Ala Arg Asp Met Ser His Leu Ile Lys
1               5                   10                  15

Glu Lys Gly Gly Leu Glu Gly Leu Tyr Tyr Ser Asp Arg Arg Arg Arg
            20                  25                  30

Val Leu Asp Ile Tyr Leu Glu
        35

<210> SEQ ID NO 208
<211> LENGTH: 38
<212> TYPE: PRT
<213> ORGANISM: Artificial sequence
<220> FEATURE:
<223> OTHER INFORMATION: 109-146 HIV-2 Nef fragment

<400> SEQUENCE: 208

Glu Met Thr Tyr Arg Leu Ala Arg Asp Met Ser His Leu Ile Lys Glu
1               5                   10                  15

Lys Gly Gly Leu Glu Gly Leu Tyr Tyr Ser Asp Arg Arg Arg Arg Val
            20                  25                  30

Leu Asp Ile Tyr Leu Glu
        35

<210> SEQ ID NO 209
<211> LENGTH: 37
<212> TYPE: PRT
<213> ORGANISM: Artificial sequence
<220> FEATURE:
<223> OTHER INFORMATION: 110-146 HIV-2 Nef fragment

<400> SEQUENCE: 209

Met Thr Tyr Arg Leu Ala Arg Asp Met Ser His Leu Ile Lys Glu Lys
1               5                   10                  15

Gly Gly Leu Glu Gly Leu Tyr Tyr Ser Asp Arg Arg Arg Arg Val Leu
            20                  25                  30

Asp Ile Tyr Leu Glu
        35

<210> SEQ ID NO 210
<211> LENGTH: 36
<212> TYPE: PRT
<213> ORGANISM: Artificial sequence
<220> FEATURE:
<223> OTHER INFORMATION: 111-146 HIV-2 Nef fragment
```

-continued

```
<400> SEQUENCE: 210

Thr Tyr Arg Leu Ala Arg Asp Met Ser His Leu Ile Lys Glu Lys Gly
1               5                   10                  15

Gly Leu Glu Gly Leu Tyr Tyr Ser Asp Arg Arg Arg Val Leu Asp
            20                  25                  30

Ile Tyr Leu Glu
        35

<210> SEQ ID NO 211
<211> LENGTH: 35
<212> TYPE: PRT
<213> ORGANISM: Artificial sequence
<220> FEATURE:
<223> OTHER INFORMATION: 112-146 HIV-2 Nef fragment

<400> SEQUENCE: 211

Tyr Arg Leu Ala Arg Asp Met Ser His Leu Ile Lys Glu Lys Gly Gly
1               5                   10                  15

Leu Glu Gly Leu Tyr Tyr Ser Asp Arg Arg Arg Val Leu Asp Ile
            20                  25                  30

Tyr Leu Glu
        35

<210> SEQ ID NO 212
<211> LENGTH: 34
<212> TYPE: PRT
<213> ORGANISM: Artificial sequence
<220> FEATURE:
<223> OTHER INFORMATION: 113-146 HIV-2 Nef fragment

<400> SEQUENCE: 212

Arg Leu Ala Arg Asp Met Ser His Leu Ile Lys Glu Lys Gly Gly Leu
1               5                   10                  15

Glu Gly Leu Tyr Tyr Ser Asp Arg Arg Arg Val Leu Asp Ile Tyr
            20                  25                  30

Leu Glu

<210> SEQ ID NO 213
<211> LENGTH: 33
<212> TYPE: PRT
<213> ORGANISM: Artificial sequence
<220> FEATURE:
<223> OTHER INFORMATION: 114-146 HIV-2 Nef fragment

<400> SEQUENCE: 213

Leu Ala Arg Asp Met Ser His Leu Ile Lys Glu Lys Gly Gly Leu Glu
1               5                   10                  15

Gly Leu Tyr Tyr Ser Asp Arg Arg Arg Val Leu Asp Ile Tyr Leu
            20                  25                  30

Glu

<210> SEQ ID NO 214
<211> LENGTH: 32
<212> TYPE: PRT
<213> ORGANISM: Artificial sequence
<220> FEATURE:
<223> OTHER INFORMATION: 115-146 HIV-2 Nef fragment

<400> SEQUENCE: 214

Ala Arg Asp Met Ser His Leu Ile Lys Glu Lys Gly Gly Leu Glu Gly
1               5                   10                  15
```

-continued

Leu Tyr Tyr Ser Asp Arg Arg Arg Arg Val Leu Asp Ile Tyr Leu Glu
            20                  25                  30

<210> SEQ ID NO 215
<211> LENGTH: 31
<212> TYPE: PRT
<213> ORGANISM: Artificial sequence
<220> FEATURE:
<223> OTHER INFORMATION: 116-146 HIV-2 Nef fragment

<400> SEQUENCE: 215

Arg Asp Met Ser His Leu Ile Lys Glu Lys Gly Gly Leu Glu Gly Leu
1               5                   10                  15

Tyr Tyr Ser Asp Arg Arg Arg Val Leu Asp Ile Tyr Leu Glu
            20                  25                  30

<210> SEQ ID NO 216
<211> LENGTH: 30
<212> TYPE: PRT
<213> ORGANISM: Artificial sequence
<220> FEATURE:
<223> OTHER INFORMATION: 117-146 HIV-2 Nef fragment

<400> SEQUENCE: 216

Asp Met Ser His Leu Ile Lys Glu Lys Gly Gly Leu Glu Gly Leu Tyr
1               5                   10                  15

Tyr Ser Asp Arg Arg Arg Val Leu Asp Ile Tyr Leu Glu
            20                  25                  30

<210> SEQ ID NO 217
<211> LENGTH: 29
<212> TYPE: PRT
<213> ORGANISM: Artificial sequence
<220> FEATURE:
<223> OTHER INFORMATION: 118-146 HIV-2 Nef fragment

<400> SEQUENCE: 217

Met Ser His Leu Ile Lys Glu Lys Gly Gly Leu Glu Gly Leu Tyr Tyr
1               5                   10                  15

Ser Asp Arg Arg Arg Arg Val Leu Asp Ile Tyr Leu Glu
            20                  25

<210> SEQ ID NO 218
<211> LENGTH: 28
<212> TYPE: PRT
<213> ORGANISM: Artificial sequence
<220> FEATURE:
<223> OTHER INFORMATION: 119-146 HIV-2 Nef fragment

<400> SEQUENCE: 218

Ser His Leu Ile Lys Glu Lys Gly Gly Leu Glu Gly Leu Tyr Tyr Ser
1               5                   10                  15

Asp Arg Arg Arg Arg Val Leu Asp Ile Tyr Leu Glu
            20                  25

<210> SEQ ID NO 219
<211> LENGTH: 27
<212> TYPE: PRT
<213> ORGANISM: Artificial sequence
<220> FEATURE:
<223> OTHER INFORMATION: 120-146 HIV-2 Nef fragment

<400> SEQUENCE: 219

His Leu Ile Lys Glu Lys Gly Gly Leu Glu Gly Leu Tyr Tyr Ser Asp
1               5                   10                  15

Arg Arg Arg Arg Val Leu Asp Ile Tyr Leu Glu
            20                  25

<210> SEQ ID NO 220
<211> LENGTH: 26
<212> TYPE: PRT
<213> ORGANISM: Artificial sequence
<220> FEATURE:
<223> OTHER INFORMATION: 121-146 HIV-2 Nef fragment

<400> SEQUENCE: 220

Leu Ile Lys Glu Lys Gly Gly Leu Glu Gly Leu Tyr Tyr Ser Asp Arg
1               5                   10                  15

Arg Arg Arg Val Leu Asp Ile Tyr Leu Glu
            20                  25

<210> SEQ ID NO 221
<211> LENGTH: 42
<212> TYPE: PRT
<213> ORGANISM: Artificial sequence
<220> FEATURE:
<223> OTHER INFORMATION: 104-145 HIV-2 Nef fragment

<400> SEQUENCE: 221

Arg Val Pro Leu Arg Glu Met Thr Tyr Arg Leu Ala Arg Asp Met Ser
1               5                   10                  15

His Leu Ile Lys Glu Lys Gly Gly Leu Glu Gly Leu Tyr Tyr Ser Asp
            20                  25                  30

Arg Arg Arg Arg Val Leu Asp Ile Tyr Leu
        35                  40

<210> SEQ ID NO 222
<211> LENGTH: 41
<212> TYPE: PRT
<213> ORGANISM: Artificial sequence
<220> FEATURE:
<223> OTHER INFORMATION: 105-145 HIV-2 Nef fragment

<400> SEQUENCE: 222

Val Pro Leu Arg Glu Met Thr Tyr Arg Leu Ala Arg Asp Met Ser His
1               5                   10                  15

Leu Ile Lys Glu Lys Gly Gly Leu Glu Gly Leu Tyr Tyr Ser Asp Arg
            20                  25                  30

Arg Arg Arg Val Leu Asp Ile Tyr Leu
        35                  40

<210> SEQ ID NO 223
<211> LENGTH: 40
<212> TYPE: PRT
<213> ORGANISM: Artificial sequence
<220> FEATURE:
<223> OTHER INFORMATION: 106-145 HIV-2 Nef fragment

<400> SEQUENCE: 223

Pro Leu Arg Glu Met Thr Tyr Arg Leu Ala Arg Asp Met Ser His Leu
1               5                   10                  15

Ile Lys Glu Lys Gly Gly Leu Glu Gly Leu Tyr Tyr Ser Asp Arg Arg
            20                  25                  30

Arg Arg Val Leu Asp Ile Tyr Leu
        35                  40

<210> SEQ ID NO 224

```
<211> LENGTH: 39
<212> TYPE: PRT
<213> ORGANISM: Artificial sequence
<220> FEATURE:
<223> OTHER INFORMATION: 107-145 HIV-2 Nef fragment

<400> SEQUENCE: 224

Leu Arg Glu Met Thr Tyr Arg Leu Ala Arg Asp Met Ser His Leu Ile
1               5                   10                  15

Lys Glu Lys Gly Gly Leu Glu Gly Leu Tyr Tyr Ser Asp Arg Arg Arg
            20                  25                  30

Arg Val Leu Asp Ile Tyr Leu
        35

<210> SEQ ID NO 225
<211> LENGTH: 38
<212> TYPE: PRT
<213> ORGANISM: Artificial sequence
<220> FEATURE:
<223> OTHER INFORMATION: 108-145 HIV-2 nef fragment

<400> SEQUENCE: 225

Arg Glu Met Thr Tyr Arg Leu Ala Arg Asp Met Ser His Leu Ile Lys
1               5                   10                  15

Glu Lys Gly Gly Leu Glu Gly Leu Tyr Tyr Ser Asp Arg Arg Arg Arg
            20                  25                  30

Val Leu Asp Ile Tyr Leu
        35

<210> SEQ ID NO 226
<211> LENGTH: 37
<212> TYPE: PRT
<213> ORGANISM: Artificial sequence
<220> FEATURE:
<223> OTHER INFORMATION: 109-145 HIV-2 Nef fragment

<400> SEQUENCE: 226

Glu Met Thr Tyr Arg Leu Ala Arg Asp Met Ser His Leu Ile Lys Glu
1               5                   10                  15

Lys Gly Gly Leu Glu Gly Leu Tyr Tyr Ser Asp Arg Arg Arg Arg Val
            20                  25                  30

Leu Asp Ile Tyr Leu
        35

<210> SEQ ID NO 227
<211> LENGTH: 36
<212> TYPE: PRT
<213> ORGANISM: Artificial sequence
<220> FEATURE:
<223> OTHER INFORMATION: 110-145 HIV-2 Nef fragment

<400> SEQUENCE: 227

Met Thr Tyr Arg Leu Ala Arg Asp Met Ser His Leu Ile Lys Glu Lys
1               5                   10                  15

Gly Gly Leu Glu Gly Leu Tyr Tyr Ser Asp Arg Arg Arg Arg Val Leu
            20                  25                  30

Asp Ile Tyr Leu
        35

<210> SEQ ID NO 228
<211> LENGTH: 35
<212> TYPE: PRT
<213> ORGANISM: Artificial sequence
```

```
<220> FEATURE:
<223> OTHER INFORMATION: 111-145 HIV-2 Nef fragment

<400> SEQUENCE: 228

Thr Tyr Arg Leu Ala Arg Asp Met Ser His Leu Ile Lys Glu Lys Gly
1               5                   10                  15

Gly Leu Glu Gly Leu Tyr Tyr Ser Asp Arg Arg Arg Val Leu Asp
            20                  25                  30

Ile Tyr Leu
        35

<210> SEQ ID NO 229
<211> LENGTH: 34
<212> TYPE: PRT
<213> ORGANISM: Artificial sequence
<220> FEATURE:
<223> OTHER INFORMATION: 112-145 HIV-2 Nef fragment

<400> SEQUENCE: 229

Tyr Arg Leu Ala Arg Asp Met Ser His Leu Ile Lys Glu Lys Gly Gly
1               5                   10                  15

Leu Glu Gly Leu Tyr Tyr Ser Asp Arg Arg Arg Val Leu Asp Ile
            20                  25                  30

Tyr Leu

<210> SEQ ID NO 230
<211> LENGTH: 33
<212> TYPE: PRT
<213> ORGANISM: Artificial sequence
<220> FEATURE:
<223> OTHER INFORMATION: 113-145 HIV-2 Nef fragment

<400> SEQUENCE: 230

Arg Leu Ala Arg Asp Met Ser His Leu Ile Lys Glu Lys Gly Gly Leu
1               5                   10                  15

Glu Gly Leu Tyr Tyr Ser Asp Arg Arg Arg Val Leu Asp Ile Tyr
            20                  25                  30

Leu

<210> SEQ ID NO 231
<211> LENGTH: 32
<212> TYPE: PRT
<213> ORGANISM: Artificial sequence
<220> FEATURE:
<223> OTHER INFORMATION: 114-145 HIV-2 Nef fragment

<400> SEQUENCE: 231

Leu Ala Arg Asp Met Ser His Leu Ile Lys Glu Lys Gly Gly Leu Glu
1               5                   10                  15

Gly Leu Tyr Tyr Ser Asp Arg Arg Arg Val Leu Asp Ile Tyr Leu
            20                  25                  30

<210> SEQ ID NO 232
<211> LENGTH: 31
<212> TYPE: PRT
<213> ORGANISM: Artificial sequence
<220> FEATURE:
<223> OTHER INFORMATION: 115-145 HIV-2 Nef fragment

<400> SEQUENCE: 232

Ala Arg Asp Met Ser His Leu Ile Lys Glu Lys Gly Gly Leu Glu Gly
1               5                   10                  15
```

```
Leu Tyr Tyr Ser Asp Arg Arg Arg Arg Val Leu Asp Ile Tyr Leu
            20                  25                  30
```

<210> SEQ ID NO 233
<211> LENGTH: 30
<212> TYPE: PRT
<213> ORGANISM: Artificial sequence
<220> FEATURE:
<223> OTHER INFORMATION: 116-145 HIV-2 Nef fragment

<400> SEQUENCE: 233

```
Arg Asp Met Ser His Leu Ile Lys Glu Lys Gly Gly Leu Glu Gly Leu
1               5                   10                  15

Tyr Tyr Ser Asp Arg Arg Arg Arg Val Leu Asp Ile Tyr Leu
            20                  25                  30
```

<210> SEQ ID NO 234
<211> LENGTH: 29
<212> TYPE: PRT
<213> ORGANISM: Artificial sequence
<220> FEATURE:
<223> OTHER INFORMATION: 117-145 HIV-2 Nef fragment

<400> SEQUENCE: 234

```
Asp Met Ser His Leu Ile Lys Glu Lys Gly Gly Leu Glu Gly Leu Tyr
1               5                   10                  15

Tyr Ser Asp Arg Arg Arg Arg Val Leu Asp Ile Tyr Leu
            20                  25
```

<210> SEQ ID NO 235
<211> LENGTH: 28
<212> TYPE: PRT
<213> ORGANISM: Artificial sequence
<220> FEATURE:
<223> OTHER INFORMATION: 118-145 HIV-2 Nef fragment

<400> SEQUENCE: 235

```
Met Ser His Leu Ile Lys Glu Lys Gly Gly Leu Glu Gly Leu Tyr Tyr
1               5                   10                  15

Ser Asp Arg Arg Arg Arg Val Leu Asp Ile Tyr Leu
            20                  25
```

<210> SEQ ID NO 236
<211> LENGTH: 27
<212> TYPE: PRT
<213> ORGANISM: Artificial sequence
<220> FEATURE:
<223> OTHER INFORMATION: 119-145 HIV-2 Nef fragment

<400> SEQUENCE: 236

```
Ser His Leu Ile Lys Glu Lys Gly Gly Leu Glu Gly Leu Tyr Tyr Ser
1               5                   10                  15

Asp Arg Arg Arg Arg Val Leu Asp Ile Tyr Leu
            20                  25
```

<210> SEQ ID NO 237
<211> LENGTH: 26
<212> TYPE: PRT
<213> ORGANISM: Artificial sequence
<220> FEATURE:
<223> OTHER INFORMATION: 120-145 HIV-2 Nef fragment

<400> SEQUENCE: 237

```
His Leu Ile Lys Glu Lys Gly Gly Leu Glu Gly Leu Tyr Tyr Ser Asp
1               5                   10                  15
```

```
Arg Arg Arg Arg Val Leu Asp Ile Tyr Leu
         20                  25

<210> SEQ ID NO 238
<211> LENGTH: 25
<212> TYPE: PRT
<213> ORGANISM: Artificial sequence
<220> FEATURE:
<223> OTHER INFORMATION: 121-145 HIV-2 Nef fragment

<400> SEQUENCE: 238

Leu Ile Lys Glu Lys Gly Gly Leu Glu Gly Leu Tyr Tyr Ser Asp Arg
1               5                   10                  15

Arg Arg Arg Val Leu Asp Ile Tyr Leu
         20                  25

<210> SEQ ID NO 239
<211> LENGTH: 41
<212> TYPE: PRT
<213> ORGANISM: Artificial sequence
<220> FEATURE:
<223> OTHER INFORMATION: 104-144 HIV-2 Nef fragment

<400> SEQUENCE: 239

Arg Val Pro Leu Arg Glu Met Thr Tyr Arg Leu Ala Arg Asp Met Ser
1               5                   10                  15

His Leu Ile Lys Glu Lys Gly Gly Leu Glu Gly Leu Tyr Tyr Ser Asp
         20                  25                  30

Arg Arg Arg Arg Val Leu Asp Ile Tyr
         35                  40

<210> SEQ ID NO 240
<211> LENGTH: 40
<212> TYPE: PRT
<213> ORGANISM: Artificial sequence
<220> FEATURE:
<223> OTHER INFORMATION: 105-144 HIV-2 Nef fragment

<400> SEQUENCE: 240

Val Pro Leu Arg Glu Met Thr Tyr Arg Leu Ala Arg Asp Met Ser His
1               5                   10                  15

Leu Ile Lys Glu Lys Gly Gly Leu Glu Gly Leu Tyr Tyr Ser Asp Arg
         20                  25                  30

Arg Arg Arg Val Leu Asp Ile Tyr
         35                  40

<210> SEQ ID NO 241
<211> LENGTH: 39
<212> TYPE: PRT
<213> ORGANISM: Artificial sequence
<220> FEATURE:
<223> OTHER INFORMATION: 106-144 HIV-2 Nef fragment

<400> SEQUENCE: 241

Pro Leu Arg Glu Met Thr Tyr Arg Leu Ala Arg Asp Met Ser His Leu
1               5                   10                  15

Ile Lys Glu Lys Gly Gly Leu Glu Gly Leu Tyr Tyr Ser Asp Arg Arg
         20                  25                  30

Arg Arg Val Leu Asp Ile Tyr
         35

<210> SEQ ID NO 242
```

```
<211> LENGTH: 38
<212> TYPE: PRT
<213> ORGANISM: Artificial sequence
<220> FEATURE:
<223> OTHER INFORMATION: 107-144 HIV-2 Nef fragment

<400> SEQUENCE: 242

Leu Arg Glu Met Thr Tyr Arg Leu Ala Arg Asp Met Ser His Leu Ile
1               5                   10                  15

Lys Glu Lys Gly Gly Leu Glu Gly Leu Tyr Tyr Ser Arg Arg Arg
            20                  25                  30

Arg Val Leu Asp Ile Tyr
        35

<210> SEQ ID NO 243
<211> LENGTH: 37
<212> TYPE: PRT
<213> ORGANISM: Artificial sequence
<220> FEATURE:
<223> OTHER INFORMATION: 108-144 HIV-2 Nef fragment

<400> SEQUENCE: 243

Arg Glu Met Thr Tyr Arg Leu Ala Arg Asp Met Ser His Leu Ile Lys
1               5                   10                  15

Glu Lys Gly Gly Leu Glu Gly Leu Tyr Tyr Ser Asp Arg Arg Arg
            20                  25                  30

Val Leu Asp Ile Tyr
        35

<210> SEQ ID NO 244
<211> LENGTH: 36
<212> TYPE: PRT
<213> ORGANISM: Artificial sequence
<220> FEATURE:
<223> OTHER INFORMATION: 109-144 HIV-2 Nef fragment

<400> SEQUENCE: 244

Glu Met Thr Tyr Arg Leu Ala Arg Asp Met Ser His Leu Ile Lys Glu
1               5                   10                  15

Lys Gly Gly Leu Glu Gly Leu Tyr Tyr Ser Asp Arg Arg Arg Val
            20                  25                  30

Leu Asp Ile Tyr
        35

<210> SEQ ID NO 245
<211> LENGTH: 35
<212> TYPE: PRT
<213> ORGANISM: Artificial sequence
<220> FEATURE:
<223> OTHER INFORMATION: 110-144 HIV-2 Nef fragment

<400> SEQUENCE: 245

Met Thr Tyr Arg Leu Ala Arg Asp Met Ser His Leu Ile Lys Glu Lys
1               5                   10                  15

Gly Gly Leu Glu Gly Leu Tyr Tyr Ser Asp Arg Arg Arg Val Leu
            20                  25                  30

Asp Ile Tyr
        35

<210> SEQ ID NO 246
<211> LENGTH: 34
<212> TYPE: PRT
<213> ORGANISM: Artificial sequence
```

```
<220> FEATURE:
<223> OTHER INFORMATION: 111-144 HIV-2 Nef fragment

<400> SEQUENCE: 246

Thr Tyr Arg Leu Ala Arg Asp Met Ser His Leu Ile Lys Glu Lys Gly
1               5                   10                  15

Gly Leu Glu Gly Leu Tyr Tyr Ser Asp Arg Arg Arg Val Leu Asp
            20                  25                  30

Ile Tyr

<210> SEQ ID NO 247
<211> LENGTH: 33
<212> TYPE: PRT
<213> ORGANISM: Artificial sequence
<220> FEATURE:
<223> OTHER INFORMATION: 112-144 HIV-2 Nef fragment

<400> SEQUENCE: 247

Tyr Arg Leu Ala Arg Asp Met Ser His Leu Ile Lys Glu Lys Gly Gly
1               5                   10                  15

Leu Glu Gly Leu Tyr Tyr Ser Asp Arg Arg Arg Arg Val Leu Asp Ile
            20                  25                  30

Tyr

<210> SEQ ID NO 248
<211> LENGTH: 32
<212> TYPE: PRT
<213> ORGANISM: Artificial sequence
<220> FEATURE:
<223> OTHER INFORMATION: 113-144 HIV-2 Nef fragment

<400> SEQUENCE: 248

Arg Leu Ala Arg Asp Met Ser His Leu Ile Lys Glu Lys Gly Gly Leu
1               5                   10                  15

Glu Gly Leu Tyr Tyr Ser Asp Arg Arg Arg Val Leu Asp Ile Tyr
            20                  25                  30

<210> SEQ ID NO 249
<211> LENGTH: 31
<212> TYPE: PRT
<213> ORGANISM: Artificial sequence
<220> FEATURE:
<223> OTHER INFORMATION: 114-144 HIV-2 Nef fragment

<400> SEQUENCE: 249

Leu Ala Arg Asp Met Ser His Leu Ile Lys Glu Lys Gly Gly Leu Glu
1               5                   10                  15

Gly Leu Tyr Tyr Ser Asp Arg Arg Arg Val Leu Asp Ile Tyr
            20                  25                  30

<210> SEQ ID NO 250
<211> LENGTH: 30
<212> TYPE: PRT
<213> ORGANISM: Artificial sequence
<220> FEATURE:
<223> OTHER INFORMATION: 115-144 HIV-2 Nef fragment

<400> SEQUENCE: 250

Ala Arg Asp Met Ser His Leu Ile Lys Glu Lys Gly Gly Leu Glu Gly
1               5                   10                  15

Leu Tyr Tyr Ser Asp Arg Arg Arg Val Leu Asp Ile Tyr
            20                  25                  30
```

```
<210> SEQ ID NO 251
<211> LENGTH: 29
<212> TYPE: PRT
<213> ORGANISM: Artificial sequence
<220> FEATURE:
<223> OTHER INFORMATION: 116-144 HIV-2 Nef fragment

<400> SEQUENCE: 251

Arg Asp Met Ser His Leu Ile Lys Glu Lys Gly Gly Leu Glu Gly Leu
1               5                   10                  15

Tyr Tyr Ser Asp Arg Arg Arg Arg Val Leu Asp Ile Tyr
            20                  25

<210> SEQ ID NO 252
<211> LENGTH: 28
<212> TYPE: PRT
<213> ORGANISM: Artificial sequence
<220> FEATURE:
<223> OTHER INFORMATION: 117-144 HIV-2 Nef fragment

<400> SEQUENCE: 252

Asp Met Ser His Leu Ile Lys Glu Lys Gly Gly Leu Glu Gly Leu Tyr
1               5                   10                  15

Tyr Ser Asp Arg Arg Arg Arg Val Leu Asp Ile Tyr
            20                  25

<210> SEQ ID NO 253
<211> LENGTH: 27
<212> TYPE: PRT
<213> ORGANISM: Artificial sequence
<220> FEATURE:
<223> OTHER INFORMATION: 118-144 HIV-2 Nef fragment

<400> SEQUENCE: 253

Met Ser His Leu Ile Lys Glu Lys Gly Gly Leu Glu Gly Leu Tyr Tyr
1               5                   10                  15

Ser Asp Arg Arg Arg Arg Val Leu Asp Ile Tyr
            20                  25

<210> SEQ ID NO 254
<211> LENGTH: 26
<212> TYPE: PRT
<213> ORGANISM: Artificial sequence
<220> FEATURE:
<223> OTHER INFORMATION: 119-144 HIV-2 Nef fragment

<400> SEQUENCE: 254

Ser His Leu Ile Lys Glu Lys Gly Gly Leu Glu Gly Leu Tyr Tyr Ser
1               5                   10                  15

Asp Arg Arg Arg Arg Val Leu Asp Ile Tyr
            20                  25

<210> SEQ ID NO 255
<211> LENGTH: 25
<212> TYPE: PRT
<213> ORGANISM: Artificial sequence
<220> FEATURE:
<223> OTHER INFORMATION: 120-144 HIV-2 Nef fragment

<400> SEQUENCE: 255

His Leu Ile Lys Glu Lys Gly Gly Leu Glu Gly Leu Tyr Tyr Ser Asp
1               5                   10                  15

Arg Arg Arg Arg Val Leu Asp Ile Tyr
            20                  25
```

<210> SEQ ID NO 256
<211> LENGTH: 24
<212> TYPE: PRT
<213> ORGANISM: Artificial sequence
<220> FEATURE:
<223> OTHER INFORMATION: 121-144 HIV-2 Nef fragment

<400> SEQUENCE: 256

Leu Ile Lys Glu Lys Gly Gly Leu Glu Gly Leu Tyr Tyr Ser Asp Arg
1               5                   10                  15

Arg Arg Arg Val Leu Asp Ile Tyr
            20

<210> SEQ ID NO 257
<211> LENGTH: 40
<212> TYPE: PRT
<213> ORGANISM: Artificial sequence
<220> FEATURE:
<223> OTHER INFORMATION: 104-143 HIV-2 Nef fragment

<400> SEQUENCE: 257

Arg Val Pro Leu Arg Glu Met Thr Tyr Arg Leu Ala Arg Asp Met Ser
1               5                   10                  15

His Leu Ile Lys Glu Lys Gly Gly Leu Glu Gly Leu Tyr Tyr Ser Asp
            20                  25                  30

Arg Arg Arg Arg Val Leu Asp Ile
        35                  40

<210> SEQ ID NO 258
<211> LENGTH: 39
<212> TYPE: PRT
<213> ORGANISM: Artificial sequence
<220> FEATURE:
<223> OTHER INFORMATION: 105-143 HIV-2 Nef fragment

<400> SEQUENCE: 258

Val Pro Leu Arg Glu Met Thr Tyr Arg Leu Ala Arg Asp Met Ser His
1               5                   10                  15

Leu Ile Lys Glu Lys Gly Gly Leu Glu Gly Leu Tyr Tyr Ser Asp Arg
            20                  25                  30

Arg Arg Arg Val Leu Asp Ile
        35

<210> SEQ ID NO 259
<211> LENGTH: 38
<212> TYPE: PRT
<213> ORGANISM: Artificial sequence
<220> FEATURE:
<223> OTHER INFORMATION: 106-143 HIV-2 Nef fragment

<400> SEQUENCE: 259

Pro Leu Arg Glu Met Thr Tyr Arg Leu Ala Arg Asp Met Ser His Leu
1               5                   10                  15

Ile Lys Glu Lys Gly Gly Leu Glu Gly Leu Tyr Tyr Ser Asp Arg Arg
            20                  25                  30

Arg Arg Val Leu Asp Ile
        35

<210> SEQ ID NO 260
<211> LENGTH: 37
<212> TYPE: PRT
<213> ORGANISM: Artificial sequence -continued
<220> FEATURE:
<223> OTHER INFORMATION: 107-143 HIV-2 Nef fragment

<400> SEQUENCE: 260

Leu Arg Glu Met Thr Tyr Arg Leu Ala Arg Asp Met Ser His Leu Ile
1               5                   10                  15

Lys Glu Lys Gly Gly Leu Glu Gly Leu Tyr Tyr Ser Asp Arg Arg Arg
            20                  25                  30

Arg Val Leu Asp Ile
        35

<210> SEQ ID NO 261
<211> LENGTH: 36
<212> TYPE: PRT
<213> ORGANISM: Artificial sequence
<220> FEATURE:
<223> OTHER INFORMATION: 108-143 HIV-2 Nef fragment

<400> SEQUENCE: 261

Arg Glu Met Thr Tyr Arg Leu Ala Arg Asp Met Ser His Leu Ile Lys
1               5                   10                  15

Glu Lys Gly Gly Leu Glu Gly Leu Tyr Tyr Ser Asp Arg Arg Arg Arg
            20                  25                  30

Val Leu Asp Ile
        35

<210> SEQ ID NO 262
<211> LENGTH: 35
<212> TYPE: PRT
<213> ORGANISM: Artificial sequence
<220> FEATURE:
<223> OTHER INFORMATION: 109-143 HIV-2 Nef fragment

<400> SEQUENCE: 262

Glu Met Thr Tyr Arg Leu Ala Arg Asp Met Ser His Leu Ile Lys Glu
1               5                   10                  15

Lys Gly Gly Leu Glu Gly Leu Tyr Tyr Ser Asp Arg Arg Arg Arg Val
            20                  25                  30

Leu Asp Ile
        35

<210> SEQ ID NO 263
<211> LENGTH: 34
<212> TYPE: PRT
<213> ORGANISM: Artificial sequence
<220> FEATURE:
<223> OTHER INFORMATION: 110-143 HIV-2 Nef fragment

<400> SEQUENCE: 263

Met Thr Tyr Arg Leu Ala Arg Asp Met Ser His Leu Ile Lys Glu Lys
1               5                   10                  15

Gly Gly Leu Glu Gly Leu Tyr Tyr Ser Asp Arg Arg Arg Arg Val Leu
            20                  25                  30

Asp Ile

<210> SEQ ID NO 264
<211> LENGTH: 33
<212> TYPE: PRT
<213> ORGANISM: Artificial sequence
<220> FEATURE:
<223> OTHER INFORMATION: 111-143 HIV-2 Nef fragment

<400> SEQUENCE: 264

```
Thr Tyr Arg Leu Ala Arg Asp Met Ser His Leu Ile Lys Glu Lys Gly
1               5                   10                  15

Gly Leu Glu Gly Leu Tyr Tyr Ser Asp Arg Arg Arg Val Leu Asp
            20                  25                  30

Ile

<210> SEQ ID NO 265
<211> LENGTH: 32
<212> TYPE: PRT
<213> ORGANISM: Artificial sequence
<220> FEATURE:
<223> OTHER INFORMATION: 112-143 HIV-2 Nef fragment

<400> SEQUENCE: 265

Tyr Arg Leu Ala Arg Asp Met Ser His Leu Ile Lys Glu Lys Gly Gly
1               5                   10                  15

Leu Glu Gly Leu Tyr Tyr Ser Asp Arg Arg Arg Val Leu Asp Ile
            20                  25                  30

<210> SEQ ID NO 266
<211> LENGTH: 31
<212> TYPE: PRT
<213> ORGANISM: Artificial sequence
<220> FEATURE:
<223> OTHER INFORMATION: 113-143 HIV-2 Nef fragment

<400> SEQUENCE: 266

Arg Leu Ala Arg Asp Met Ser His Leu Ile Lys Glu Lys Gly Gly Leu
1               5                   10                  15

Glu Gly Leu Tyr Tyr Ser Asp Arg Arg Arg Val Leu Asp Ile
            20                  25                  30

<210> SEQ ID NO 267
<211> LENGTH: 30
<212> TYPE: PRT
<213> ORGANISM: Artificial sequence
<220> FEATURE:
<223> OTHER INFORMATION: 114-143 HIV-2 Nef fragment

<400> SEQUENCE: 267

Leu Ala Arg Asp Met Ser His Leu Ile Lys Glu Lys Gly Gly Leu Glu
1               5                   10                  15

Gly Leu Tyr Tyr Ser Asp Arg Arg Arg Val Leu Asp Ile
            20                  25                  30

<210> SEQ ID NO 268
<211> LENGTH: 29
<212> TYPE: PRT
<213> ORGANISM: Artificial sequence
<220> FEATURE:
<223> OTHER INFORMATION: 115-143 HIV-2 Nef fragment

<400> SEQUENCE: 268

Ala Arg Asp Met Ser His Leu Ile Lys Glu Lys Gly Gly Leu Glu Gly
1               5                   10                  15

Leu Tyr Tyr Ser Asp Arg Arg Arg Val Leu Asp Ile
            20                  25

<210> SEQ ID NO 269
<211> LENGTH: 28
<212> TYPE: PRT
<213> ORGANISM: Artificial sequence
<220> FEATURE:
```

<223> OTHER INFORMATION: 116-143 HIV-2 Nef fragment

<400> SEQUENCE: 269

Arg Asp Met Ser His Leu Ile Lys Glu Lys Gly Gly Leu Glu Gly Leu
1               5                   10                  15

Tyr Tyr Ser Asp Arg Arg Arg Val Leu Asp Ile
            20                  25

<210> SEQ ID NO 270
<211> LENGTH: 27
<212> TYPE: PRT
<213> ORGANISM: Artificial sequence
<220> FEATURE:
<223> OTHER INFORMATION: 117-143 HIV-2 Nef fragment

<400> SEQUENCE: 270

Asp Met Ser His Leu Ile Lys Glu Lys Gly Gly Leu Glu Gly Leu Tyr
1               5                   10                  15

Tyr Ser Asp Arg Arg Arg Arg Val Leu Asp Ile
            20                  25

<210> SEQ ID NO 271
<211> LENGTH: 26
<212> TYPE: PRT
<213> ORGANISM: Artificial sequence
<220> FEATURE:
<223> OTHER INFORMATION: 118-143 HIV-2 Nef fragment

<400> SEQUENCE: 271

Met Ser His Leu Ile Lys Glu Lys Gly Gly Leu Glu Gly Leu Tyr Tyr
1               5                   10                  15

Ser Asp Arg Arg Arg Arg Val Leu Asp Ile
            20                  25

<210> SEQ ID NO 272
<211> LENGTH: 25
<212> TYPE: PRT
<213> ORGANISM: Artificial sequence
<220> FEATURE:
<223> OTHER INFORMATION: 119-143 HIV-2 Nef fragment

<400> SEQUENCE: 272

Ser His Leu Ile Lys Glu Lys Gly Gly Leu Glu Gly Leu Tyr Tyr Ser
1               5                   10                  15

Asp Arg Arg Arg Arg Val Leu Asp Ile
            20                  25

<210> SEQ ID NO 273
<211> LENGTH: 24
<212> TYPE: PRT
<213> ORGANISM: Artificial sequence
<220> FEATURE:
<223> OTHER INFORMATION: 120-143 HIV-2 Nef fragment

<400> SEQUENCE: 273

His Leu Ile Lys Glu Lys Gly Gly Leu Glu Gly Leu Tyr Tyr Ser Asp
1               5                   10                  15

Arg Arg Arg Arg Val Leu Asp Ile
            20

<210> SEQ ID NO 274
<211> LENGTH: 23
<212> TYPE: PRT
<213> ORGANISM: Artificial sequence

```
<220> FEATURE:
<223> OTHER INFORMATION: 121-143 HIV-2 Nef fragment

<400> SEQUENCE: 274

Leu Ile Lys Glu Lys Gly Gly Leu Glu Gly Leu Tyr Tyr Ser Asp Arg
1               5                   10                  15

Arg Arg Arg Val Leu Asp Ile
            20

<210> SEQ ID NO 275
<211> LENGTH: 205
<212> TYPE: PRT
<213> ORGANISM: Human immunodeficiency virus type 1

<400> SEQUENCE: 275

Met Gly Gly Lys Trp Ser Lys Ser Arg Val Glu Trp Pro Glu Val
1               5                   10                  15

Arg Lys Arg Met Arg Glu Thr Pro Ala Ala Ala Lys Gly Val Gly Ala
            20                  25                  30

Val Ser Gln Asp Leu Asp Lys Tyr Gly Ala Val Thr Ser Ser Asn Thr
        35                  40                  45

Ser Ser Thr Asn Ala Ser Cys Ala Trp Leu Glu Ala Gln Glu Glu Gly
    50                  55                  60

Asp Val Gly Phe Pro Val Arg Pro Gln Val Pro Leu Arg Pro Met Thr
65                  70                  75                  80

Tyr Lys Ala Ala Phe Asp Leu Ser Phe Phe Leu Lys Glu Lys Gly Gly
                85                  90                  95

Leu Asp Gly Leu Ile His Ser Gln Lys Arg Gln Glu Ile Leu Asp Leu
            100                 105                 110

Trp Val Tyr His Thr Gln Gly Phe Phe Pro Asp Trp Gln Asn Tyr Thr
        115                 120                 125

Pro Gly Pro Gly Ile Arg Tyr Pro Leu Thr Phe Gly Trp Cys Tyr Lys
    130                 135                 140

Leu Val Pro Val Asp Pro Ala Glu Val Glu Glu Ala Thr Gly Gly Glu
145                 150                 155                 160

Asn Asn Ser Leu Leu His Pro Ile Cys Gln His Gly Val Asp Asp Glu
                165                 170                 175

Glu Lys Glu Val Leu Met Trp Lys Phe Asp Ser Thr Leu Ala Leu Lys
            180                 185                 190

His Arg Ala Tyr Glu Leu His Pro Glu Phe Tyr Lys Asp
        195                 200                 205

<210> SEQ ID NO 276
<211> LENGTH: 206
<212> TYPE: PRT
<213> ORGANISM: Human immunodeficiency virus type 1

<400> SEQUENCE: 276

Met Gly Gly Lys Trp Ser Lys Ser Ser Ile Val Gly Trp Pro Ala Ile
1               5                   10                  15

Arg Glu Arg Ile Arg Arg Thr Asn Pro Ala Ala Asp Gly Val Gly Ala
            20                  25                  30

Val Ser Arg Asp Leu Glu Lys His Gly Ala Ile Thr Ser Ser Asn Thr
        35                  40                  45

Ala Ser Thr Asn Ala Asp Cys Ala Trp Leu Glu Ala Gln Glu Glu Ser
    50                  55                  60

Asp Glu Val Gly Phe Pro Val Arg Pro Gln Val Pro Leu Arg Pro Met
```

```
                65                  70                  75                  80
Thr Tyr Lys Glu Ala Leu Asp Leu Ser His Phe Leu Lys Glu Lys Gly
                    85                  90                  95

Gly Leu Glu Gly Leu Ile Trp Ser Lys Lys Arg Gln Glu Ile Leu Asp
                100                 105                 110

Leu Trp Val Tyr Asn Thr Gln Gly Ile Phe Pro Asp Trp Gln Asn Tyr
                115                 120                 125

Thr Pro Gly Pro Gly Ile Arg Tyr Pro Leu Thr Phe Gly Trp Cys Tyr
            130                 135                 140

Glu Leu Val Pro Val Asp Pro Gln Glu Val Glu Glu Asp Thr Glu Gly
145                 150                 155                 160

Glu Thr Asn Ser Leu Leu His Pro Ile Cys Gln His Gly Met Glu Asp
                165                 170                 175

Pro Glu Arg Gln Val Leu Lys Trp Arg Phe Asn Ser Arg Leu Ala Phe
            180                 185                 190

Glu His Lys Ala Arg Glu Met His Pro Glu Phe Tyr Lys Asn
            195                 200                 205

<210> SEQ ID NO 277
<211> LENGTH: 205
<212> TYPE: PRT
<213> ORGANISM: Human immunodeficiency virus type 1

<400> SEQUENCE: 277

Met Gly Asn Lys Trp Ser Lys Gly Trp Pro Ala Val Arg Glu Arg Ile
1               5                   10                  15

Arg Gln Thr Pro Pro Ala Pro Ala Ala Glu Gly Val Gly Ala Ala
                20                  25                  30

Ser Gln Asp Leu Ala Lys His Gly Ala Ile Ser Ser Ser Asn Thr Ala
                35                  40                  45

Thr Asn Asn Pro Asp Cys Ala Trp Leu Glu Ala Gln Glu Glu Ser Glu
            50                  55                  60

Glu Val Gly Phe Pro Val Arg Pro Gln Val Pro Leu Arg Pro Met Thr
65                  70                  75                  80

Phe Lys Gly Ala Phe Asp Leu Ser Phe Phe Leu Lys Glu Lys Gly Gly
                85                  90                  95

Leu Asp Gly Leu Ile Tyr Ser Lys Lys Arg Gln Glu Ile Leu Asp Leu
                100                 105                 110

Trp Val Tyr His Thr Gln Gly Phe Phe Pro Asp Trp His Asn Tyr Thr
                115                 120                 125

Pro Gly Pro Gly Thr Arg Tyr Pro Leu Cys Phe Gly Trp Cys Phe Lys
            130                 135                 140

Leu Val Pro Val Asp Pro Arg Glu Val Glu Glu Ala Asn Thr Gly Glu
145                 150                 155                 160

Asn Asn Cys Leu Leu His Pro Met Ser Gln His Gly Met Asp Asp Asp
                165                 170                 175

Glu Arg Glu Val Leu Met Trp Lys Phe Asp Ser Ser Leu Ala Arg Lys
            180                 185                 190

His Leu Ala Arg Glu Met His Pro Glu Phe Tyr Lys Asp
            195                 200                 205

<210> SEQ ID NO 278
<211> LENGTH: 206
<212> TYPE: PRT
<213> ORGANISM: Human immunodeficiency virus type 1
```

<400> SEQUENCE: 278

```
Met Gly Gly Lys Trp Ser Lys Ser Ser Val Val Gly Trp Pro Ala Val
1               5                   10                  15

Arg Glu Arg Met Arg Arg Ala Glu Pro Ala Ala Asp Gly Val Gly Ala
            20                  25                  30

Ala Ser Arg Asp Leu Glu Lys His Gly Ala Ile Thr Ser Ser Asn Thr
        35                  40                  45

Ala Ala Asn Asn Ala Ala Cys Ala Trp Leu Glu Ala Gln Glu Glu Glu
    50                  55                  60

Lys Val Gly Phe Pro Val Thr Pro Gln Val Pro Leu Arg Pro Met Thr
65                  70                  75                  80

Tyr Lys Ala Ala Val Asp Leu Ser His Phe Leu Lys Glu Lys Gly Gly
                85                  90                  95

Leu Glu Gly Leu Ile His Ser Gln Arg Arg Gln Asp Ile Leu Asp Leu
            100                 105                 110

Trp Ile Tyr His Thr Gln Gly Tyr Phe Pro Asp Trp Gln Asn Tyr Thr
        115                 120                 125

Pro Gly Pro Gly Ile Arg Tyr Pro Leu Thr Phe Gly Trp Cys Tyr Lys
    130                 135                 140

Leu Val Pro Val Glu Pro Glu Lys Leu Glu Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
            180                 185                 190

His Val Ala Arg Glu Leu His Pro Glu Tyr Phe Lys Asn Cys
        195                 200                 205
```

<210> SEQ ID NO 279
<211> LENGTH: 239
<212> TYPE: PRT
<213> ORGANISM: Human immunodeficiency virus type 1

<400> SEQUENCE: 279

```
Met Gly Gly Lys Trp Ser Lys Arg Ser Val Val Gly Trp Pro Thr Val
1               5                   10                  15

Arg Glu Arg Met Arg Lys Thr Glu Pro Ala Ala Asp Gly Val Gly Ala
            20                  25                  30

Ala Ser Arg Asp Leu Glu Lys His Gly Ala Ile Thr Ser Ser Asn Thr
        35                  40                  45

Pro Ala Asn Asn Ala Asp Cys Ala Trp Leu Glu Ala Gln Glu Glu Glu
    50                  55                  60

Glu Val Gly Phe Pro Val Arg Pro Gln Val Pro Leu Arg Pro Met Thr
65                  70                  75                  80

Tyr Lys Ala Ala Val Asp Leu Ser His Phe Leu Lys Glu Gln Gly Gly
                85                  90                  95

Leu Glu Gly Leu Ile Thr Pro Arg Glu Asp Lys Ile Ser Leu Ile Cys
            100                 105                 110

Gly Ser Thr Thr His Lys Ala Thr Ser Leu Ile Gly Arg Thr Thr His
        115                 120                 125

Gln Gly Gln Gly Ser Asp Ile Pro Leu Cys Phe Gly Trp Cys Phe Lys
    130                 135                 140

Leu Val Pro Val Lys Pro Glu Lys Ile Glu Glu Ala Asn Glu Gly Glu
145                 150                 155                 160
```

```
Asn Asn Ser Leu Leu His Pro Met Ser Leu His Gly Met Glu Asp Pro
            165                 170                 175

Glu Arg Glu Val Leu Glu Trp Arg Phe Asp Asn Arg Leu Ala Phe His
            180                 185                 190

His Met Ala Arg Asp Leu His Pro Glu Tyr Tyr Lys Asp Cys Leu Thr
            195                 200                 205

Ser Met Cys Leu Gln Gly Thr Phe Arg Trp Gly Ile Ser Arg Glu Ala
        210                 215                 220

Arg Leu Gly Gly Thr Gly Glu Trp Arg Ala Leu Arg Cys Cys Ile
225                 230                 235

<210> SEQ ID NO 280
<211> LENGTH: 216
<212> TYPE: PRT
<213> ORGANISM: Human immunodeficiency virus type 1

<400> SEQUENCE: 280

Met Gly Gly Lys Trp Ser Lys His Ser Val Pro Gly Trp Ser Thr Val
1               5                   10                  15

Arg Glu Arg Met Arg Arg Ala Glu Pro Ala Thr Asp Arg Val Arg Gln
            20                  25                  30

Thr Glu Pro Ala Ala Val Gly Val Gly Ala Val Ser Arg Asp Leu Glu
        35                  40                  45

Lys His Gly Ala Ile Thr Ser Ser Asn Thr Ala Ala Thr Asn Ala Asp
    50                  55                  60

Cys Ala Trp Leu Glu Ala Tyr Glu Asp Glu Glu Val Gly Phe Pro Val
65                  70                  75                  80

Arg Pro Gln Val Pro Leu Arg Pro Met Thr Tyr Lys Ala Ala Ile Asp
                85                  90                  95

Leu Ser His Phe Leu Lys Glu Lys Gly Gly Leu Glu Gly Leu Ile Tyr
            100                 105                 110

Ser Gln Lys Arg Gln Asp Ile Leu Asp Leu Trp Ile Tyr His Thr Gln
        115                 120                 125

Gly Tyr Phe Pro Asp Trp Gln Asn Tyr Thr Ala Gly Pro Gly Val Arg
    130                 135                 140

Phe Pro Leu Thr Phe Gly Trp Cys Phe Lys Leu Val Pro Val Asp Pro
145                 150                 155                 160

Glu Lys Val Glu Glu Ala Asn Glu Gly Glu Asn Asn Cys Leu Leu His
                165                 170                 175

Pro Met Ser Gln His Gly Met Asp Asp Pro Glu Lys Glu Val Leu Val
            180                 185                 190

Trp Lys Phe Asp Ser Lys Leu Ala Leu His His Val Ala Arg Glu Leu
        195                 200                 205

His Pro Glu Tyr Tyr Lys Asp Cys
    210                 215

<210> SEQ ID NO 281
<211> LENGTH: 209
<212> TYPE: PRT
<213> ORGANISM: Human immunodeficiency virus type 1

<400> SEQUENCE: 281

Met Gly Gly Lys Trp Ser Lys Ser Ser Ile Val Gly Trp Pro Lys Ile
1               5                   10                  15

Arg Glu Arg Ile Arg Arg Thr Pro Pro Thr Glu Thr Gly Val Gly Ala
            20                  25                  30
```

-continued

```
Val Ser Gln Asp Ala Val Ser Gln Asp Leu Asp Lys Cys Gly Ala Ala
35 40 45

Ala Ser Ser Ser Pro Ala Ala Asn Asn Ala Ser Cys Glu Pro Pro Glu
50 55 60

Glu Glu Glu Glu Val Gly Phe Pro Val Arg Pro Gln Val Pro Leu Arg
65 70 75 80

Pro Met Thr Tyr Lys Gly Ala Phe Asp Leu Ser His Phe Leu Lys Glu
85 90 95

Lys Gly Gly Leu Asp Gly Leu Val Trp Ser Pro Lys Arg Gln Glu Ile
100 105 110

Leu Asp Leu Trp Val Tyr His Thr Gln Gly Tyr Phe Pro Asp Trp Gln
115 120 125

Asn Tyr Thr Pro Gly Pro Gly Ile Arg Phe Pro Leu Thr Phe Gly Trp
130 135 140

Cys Phe Lys Leu Val Pro Met Ser Pro Glu Glu Val Glu Glu Ala Asn
145 150 155 160

Glu Gly Glu Asn Asn Cys Leu Leu His Pro Ile Ser Gln His Gly Met
165 170 175

Glu Asp Ala Glu Arg Glu Val Leu Lys Trp Lys Phe Asp Ser Ser Leu
180 185 190

Ala Leu Arg His Arg Ala Arg Glu Gln His Pro Glu Tyr Tyr Lys Asp
195 200 205

Cys

<210> SEQ ID NO 282
<211> LENGTH: 205
<212> TYPE: PRT
<213> ORGANISM: Simian immunodeficiency virus

<400> SEQUENCE: 282

Met Gly Thr Lys Trp Ser Lys Ser Ser Leu Val Gly Trp Pro Glu Val
1 5 10 15

Arg Arg Arg Ile Arg Glu Ala Pro Thr Ala Ala Glu Gly Val Gly Glu
20 25 30

Val Ser Lys Asp Leu Glu Arg His Gly Ala Ile Thr Ser Arg Asn Thr
35 40 45

Pro Glu Thr Asn Gln Thr Leu Ala Trp Leu Glu Glu Met Asp Asn Glu
50 55 60

Glu Val Gly Phe Pro Val Arg Pro Gln Val Pro Thr Arg Pro Met Thr
65 70 75 80

Tyr Lys Ala Ala Phe Asp Leu Ser His Phe Leu Lys Glu Lys Gly Gly
85 90 95

Leu Glu Gly Leu Val Tyr Ser Arg Arg Arg Gln Glu Ile Leu Asp Leu
100 105 110

Trp Val Tyr His Thr Gln Gly Phe Phe Pro Asp Trp Gln Asn Tyr Thr
115 120 125

Thr Gly Pro Gly Thr Arg Phe Pro Leu Cys Phe Gly Trp Cys Phe Lys
130 135 140

Leu Val Pro Leu Thr Glu Glu Gln Val Glu Gln Ala Asn Glu Gly Asp
145 150 155 160

Asn Asn Cys Leu Leu His Pro Ile Cys Gln His Gly Met Glu Asp Glu
165 170 175

Asp Lys Glu Val Leu Val Trp Arg Phe Asp Ser Arg Leu Ala Leu Arg
180 185 190

His Ile Ala Arg Glu Gln His Pro Glu Tyr Tyr Lys Asp
            195                 200                 205

<210> SEQ ID NO 283
<211> LENGTH: 309
<212> TYPE: PRT
<213> ORGANISM: Simian immunodeficiency virus

<400> SEQUENCE: 283

Met Gly Gly Ala Ile Ser Lys Lys Gln Tyr Lys Arg Gly Gly Asn Leu
1               5                   10                  15

Arg Glu Arg Leu Leu Gln Ala Arg Gly Glu Thr Tyr Gly Arg Leu Trp
            20                  25                  30

Glu Gly Leu Glu Glu Gly Tyr Ser Gln Ser Leu Gly Ala Ser Gly Lys
        35                  40                  45

Gly Leu Ser Ser Leu Ser Cys Glu Pro Gln Lys Tyr Ser Glu Gly Gln
50                  55                  60

Tyr Met Asn Thr Pro Trp Arg Asn Pro Ala Thr Glu Arg Ala Lys Leu
65                  70                  75                  80

Gly Tyr Arg Gln Gln Asn Met Asp Asp Val Asp Asp Glu Asp Asp Asp
            85                  90                  95

Leu Ile Gly Val Ser Val His Pro Arg Val Pro Leu Arg Ala Met Thr
        100                 105                 110

Tyr Lys Leu Ala Ile Asp Met Ser His Phe Ile Lys Glu Lys Gly Gly
        115                 120                 125

Leu Glu Gly Ile Tyr Tyr Asn Glu Arg Arg His Arg Ile Leu Asp Met
130                 135                 140

Tyr Leu Glu Lys Glu Glu Gly Ile Ile Pro Asp Trp Gln Asn Tyr Thr
145                 150                 155                 160

Ser Gly Pro Gly Ile Arg Tyr Pro Met His Tyr Gly Trp Leu Trp Lys
            165                 170                 175

Leu Val Pro Val Asp Val Ser Asp Glu Ala Gln Glu Asp Glu Thr His
        180                 185                 190

Cys Leu Val His Pro Ala Gln Thr Tyr Gln Trp Asp Asp Pro Trp Gly
        195                 200                 205

Glu Val Leu Ala Trp Lys Phe Asp Pro Glu Leu Ala Tyr Ser Tyr Lys
210                 215                 220

Ala Phe Ile Lys Tyr Pro Glu Glu Phe Gly Ser Lys Ser Gly Leu Ser
225                 230                 235                 240

Glu Glu Glu Val Lys Arg Arg Leu Thr Ala Arg Gly Leu Leu Lys Trp
            245                 250                 255

Leu Thr Arg Arg Lys Gln Ala Glu Thr Ala Gly Thr Phe His Lys Gly
        260                 265                 270

Leu Ser Trp Glu Val Leu Gly Arg Ser Trp Leu Glu Arg Pro Leu Ile
        275                 280                 285

Leu Cys Ile Asn Thr Thr Ala Phe Arg Ser Val Phe Ser Arg Ser Ala
        290                 295                 300

Glu Arg Leu Ala Asp
305

<210> SEQ ID NO 284
<211> LENGTH: 262
<212> TYPE: PRT
<213> ORGANISM: Simian immunodeficiency virus

<400> SEQUENCE: 284

```
Met Gly Gly Ala Ile Ser Lys Lys Arg Ser Lys Pro Pro Arg Asp Leu
1               5                   10                  15

Arg Gln Arg Leu Leu Arg Ala Arg Gly Glu Asn Tyr Gly Arg Leu Phe
            20                  25                  30

Lys Gly Val Glu Asp Gly Ser Ser Gln Ser Leu Gly Gly Leu Asp Lys
            35                  40                  45

Gly Leu Ser Ser Leu Ser Cys Glu Gly Gln Lys Tyr Asn Gln Gly Glu
        50                  55                  60

Tyr Met Asn Thr Pro Trp Arg Asn Pro Ala Glu Arg Lys Lys Leu
65                  70                  75                  80

Pro Tyr Arg Lys Gln Asn Ile Asp Asp Ile Asp Glu Asp Asp
                85                  90                  95

Leu Val Gly Ile Pro Val Glu Ala Arg Val Pro Leu Arg Thr Met Ser
            100                 105                 110

Tyr Lys Leu Ala Ile Asp Met Ser His Phe Ile Lys Glu Lys Gly Gly
            115                 120                 125

Leu Glu Gly Ile Tyr Tyr Ser Ala Arg Arg His Arg Ile Leu Asp Ile
            130                 135                 140

Tyr Leu Glu Lys Glu Glu Gly Ile Ile Pro Asp Trp Gln Ile His Ser
145                 150                 155                 160

Gly Pro Gly Ile Arg Tyr Leu Lys Met Phe Gly Trp Leu Trp Lys Leu
                165                 170                 175

Ile Pro Val Asn Val Ser Asp Glu Ala Gln Glu Asp Glu Glu His Tyr
            180                 185                 190

Leu Val His Pro Ala Gln Thr Ser Gln Trp Asp Asp Pro Trp Gly Glu
            195                 200                 205

Val Leu Ala Trp Lys Phe Asp Pro Thr Leu Ala Tyr Thr Tyr Glu Ala
            210                 215                 220

Tyr Ile Arg Tyr Pro Glu Glu Phe Gly Ser Lys Ser Gly Leu Ser Glu
225                 230                 235                 240

Lys Glu Val Lys Arg Arg Leu Ala Ala Arg Gly Leu Leu Glu Met Ala
                245                 250                 255

Asp Arg Lys Glu Thr Ser
            260

<210> SEQ ID NO 285
<211> LENGTH: 256
<212> TYPE: PRT
<213> ORGANISM: Human immunodeficiency virus type 2

<400> SEQUENCE: 285

Met Gly Ala Ser Gly Ser Lys Lys Arg Ser Arg Pro Ser Arg Gly Leu
1               5                   10                  15

Gln Glu Arg Leu Leu Arg Ala Arg Gly Gly Ala Cys Gly Gly Leu Trp
            20                  25                  30

Asp Glu Ser Glu Gly Gly Tyr Ser Gln Phe His Glu Gly Ser Gly Arg
            35                  40                  45

Glu Gln Lys Leu Pro Ser Cys Glu Gly Gln Arg Tyr Gln Gln Gly Asp
        50                  55                  60

Phe Met Asn Thr Pro Trp Arg Thr Pro Ala Thr Glu Lys Glu Lys Glu
65                  70                  75                  80

Ser Tyr Arg Gln Gln Asn Met Asp Asp Val Asp Ser Asp Asp Asp
                85                  90                  95

Leu Val Gly Val Ser Asp Thr Ser Arg Val Pro Leu Arg Ala Met Thr
            100                 105                 110
```

```
Tyr Arg Met Ala Val Asp Met Ser Asp Leu Ile Lys Asp Lys Gly Gly
            115                 120                 125

Leu Glu Gly Met Tyr Tyr Ser Glu Arg Arg His Arg Ile Leu Asp Ile
        130                 135                 140

Tyr Leu Glu Lys Glu Glu Gly Ile Ile Pro Asp Trp Gln Asn Tyr Thr
145                 150                 155                 160

His Gly Leu Gly Val Arg Tyr Pro Met Phe Phe Gly Trp Leu Trp Lys
                165                 170                 175

Leu Val Pro Val Thr Val Pro Gln Glu Gly Glu Asp Thr Glu Thr Leu
            180                 185                 190

Cys Leu Met His Ser Ala Gln Val Ser Arg Phe Asp Asp Pro His Gly
            195                 200                 205

Glu Thr Leu Val Trp Lys Phe Asp Pro Met Leu Ala His Glu Tyr Thr
        210                 215                 220

Thr Phe Ile Leu Tyr Pro Glu Glu Phe Gly His Lys Ser Gly Met Glu
225                 230                 235                 240

Glu Asp Asp Trp Lys Ala Lys Leu Lys Ala Arg Gly Ile Pro Phe Ser
                245                 250                 255

<210> SEQ ID NO 286
<211> LENGTH: 256
<212> TYPE: PRT
<213> ORGANISM: Human immunodeficiency virus type 2

<400> SEQUENCE: 286

Met Gly Ala Ser Gly Ser Lys Lys His Ser Arg Pro Pro Arg Gly Leu
1               5                   10                  15

Gln Glu Arg Leu Leu Arg Ala Arg Ala Gly Ala Cys Gly Gly Tyr Trp
            20                  25                  30

Asn Glu Ser Gly Gly Glu Tyr Ser Arg Phe Gln Glu Gly Ser Asp Arg
        35                  40                  45

Glu Gln Lys Ser Pro Ser Cys Glu Gly Arg Gln Tyr Gln Gln Gly Asp
    50                  55                  60

Phe Met Asn Thr Pro Trp Lys Asp Pro Ala Ala Glu Arg Glu Lys Asn
65                  70                  75                  80

Leu Tyr Arg Gln Gln Asn Met Asp Asp Val Asp Ser Asp Asp Asp Asp
                85                  90                  95

Gln Val Arg Val Ser Val Thr Pro Lys Val Pro Leu Arg Pro Met Thr
            100                 105                 110

His Arg Leu Ala Ile Asp Met Ser His Leu Ile Lys Thr Arg Gly Gly
            115                 120                 125

Leu Glu Gly Met Phe Tyr Ser Glu Arg Arg His Lys Ile Leu Asn Ile
        130                 135                 140

Tyr Leu Glu Lys Glu Glu Gly Ile Ile Ala Asp Trp Gln Asn Tyr Thr
145                 150                 155                 160

His Gly Pro Gly Val Arg Tyr Pro Met Phe Phe Gly Trp Leu Trp Lys
                165                 170                 175

Leu Val Pro Val Asp Val Pro Gln Glu Gly Glu Asp Thr Glu Thr His
            180                 185                 190

Cys Leu Val His Pro Ala Gln Thr Ser Lys Phe Asp Asp Pro His Gly
            195                 200                 205

Glu Thr Leu Val Trp Glu Phe Asp Pro Leu Leu Ala Tyr Ser Tyr Glu
        210                 215                 220

Ala Phe Ile Arg Tyr Pro Glu Glu Phe Gly His Lys Ser Gly Leu Pro
```

```
                225                 230                 235                 240
Glu Glu Glu Trp Lys Ala Arg Leu Lys Ala Arg Gly Ile Pro Phe Ser
                245                 250                 255

<210> SEQ ID NO 287
<211> LENGTH: 255
<212> TYPE: PRT
<213> ORGANISM: Human immunodeficiency virus type 2

<400> SEQUENCE: 287

Met Gly Ala Ser Gly Ser Lys Lys Arg Ser Glu Pro Ser Arg Gly Leu
1               5                   10                  15

Arg Glu Arg Leu Leu Gln Thr Pro Gly Glu Ala Ser Gly Gly His Trp
                20                  25                  30

Asp Lys Leu Gly Gly Glu Tyr Leu Gln Ser Gln Glu Gly Ser Gly Arg
            35                  40                  45

Gly Gln Lys Ser Pro Ser Cys Glu Gly Arg Arg Tyr Gln Gln Gly Asp
        50                  55                  60

Phe Met Asn Thr Pro Trp Arg Ala Pro Ala Glu Gly Glu Lys Gly Ser
65                  70                  75                  80

Tyr Lys Gln Gln Asn Met Asp Asp Val Asp Ser Asp Asp Asp Leu
                85                  90                  95

Val Gly Val Pro Val Thr Pro Arg Val Pro Leu Arg Glu Met Thr Tyr
                100                 105                 110

Arg Leu Ala Arg Asp Met Ser His Leu Ile Lys Glu Lys Gly Gly Leu
            115                 120                 125

Glu Gly Leu Tyr Tyr Ser Asp Arg Arg Arg Val Leu Asp Ile Tyr
        130                 135                 140

Leu Glu Lys Glu Glu Gly Ile Ile Gly Asp Trp Gln Asn Tyr Thr His
145                 150                 155                 160

Gly Pro Gly Val Arg Tyr Pro Lys Phe Phe Gly Trp Leu Trp Lys Leu
                165                 170                 175

Val Pro Val Asp Val Pro Gln Glu Gly Asp Asp Ser Glu Thr His Cys
                180                 185                 190

Leu Val His Pro Ala Gln Thr Ser Arg Phe Asp Asp Pro His Gly Glu
            195                 200                 205

Thr Leu Val Trp Arg Phe Asp Pro Thr Leu Ala Phe Ser Tyr Glu Ala
        210                 215                 220

Phe Ile Arg Tyr Pro Glu Glu Phe Gly Tyr Lys Ser Gly Leu Pro Glu
225                 230                 235                 240

Asp Glu Trp Lys Ala Arg Leu Lys Ala Arg Gly Ile Pro Phe Ser
                245                 250                 255

<210> SEQ ID NO 288
<211> LENGTH: 260
<212> TYPE: PRT
<213> ORGANISM: Human immunodeficiency virus type 2

<400> SEQUENCE: 288

Met Gly Ala Ser Gly Ser Lys Lys Arg Ser Arg Pro Leu Gln Gly Leu
1               5                   10                  15

Gln Glu Arg Leu Leu Arg Ala Arg Ala Gly Thr Cys Gly Glu Cys Tyr
                20                  25                  30

Asn Ala Leu Glu Gly Glu Ser Leu Arg Ser Gln Glu Gly Ser Asp Arg
            35                  40                  45

Glu Gln Asn Ser Leu Ser Cys Glu Gly Gln Arg Tyr Gln Gln Gly Asp
```

```
                    50                  55                  60
Phe Met Asn Thr Pro Trp Arg Ala Pro Ala Glu Gly Lys Lys Asn
 65                  70                  75                  80

Ala Tyr Arg Gln Gln Asn Met Asp Asp Ile Asp Ser Asp Asp Asp
                    85                  90                  95

Leu Val Gly Val Pro Ala Thr Pro Arg Val Pro Leu Arg Thr Met Thr
                100                 105                 110

Tyr Lys Leu Ala Val Asp Met Ser His Phe Ile Lys Glu Lys Gly Gly
                115                 120                 125

Leu Glu Gly Leu Phe Tyr Ser Glu Arg Arg His Arg Ile Leu Asp Ile
                130                 135                 140

Tyr Leu Glu Lys Glu Glu Gly Ile Ile Ala Asp Trp Gln Asn Tyr Thr
145                 150                 155                 160

Ser Gly Pro Gly Val Arg Tyr Pro Met Phe Phe Gly Trp Leu Trp Lys
                165                 170                 175

Leu Val Pro Val Asp Thr Ser Gln Glu Gly Glu Asp Thr Glu Thr Asp
                180                 185                 190

Thr Glu Thr His Cys Leu Leu His Pro Ala Gln Thr Ser Arg His Asp
                195                 200                 205

Asp Met His Gly Glu Thr Leu Val Trp Lys Phe Asp Ser Met Leu Ala
210                 215                 220

Leu Lys Tyr Glu Ala Phe Thr Arg Tyr Pro Glu Glu Phe Gly His Lys
225                 230                 235                 240

Ser Gly Leu Pro Glu Asp Glu Trp Lys Ala Lys Leu Lys Ala Arg Gly
                245                 250                 255

Ile Pro Phe Ser
                260

<210> SEQ ID NO 289
<211> LENGTH: 257
<212> TYPE: PRT
<213> ORGANISM: Human immunodeficiency virus type 2

<400> SEQUENCE: 289

Met Gly Ala Ser Gly Ser Lys Lys Leu Ser Lys His Ser Arg Gly Leu
 1                   5                  10                  15

Arg Glu Arg Leu Leu Arg Ala Arg Gly Asp Gly Tyr Gly Lys Gln Arg
                    20                  25                  30

Asp Ala Ser Gly Gly Glu Tyr Ser Gln Phe Gln Glu Glu Ser Gly Arg
                    35                  40                  45

Glu Gln Asn Ser Pro Ser Cys Glu Gly Gln Gln Tyr Gln Gln Gly Glu
                    50                  55                  60

Tyr Met Asn Ser Pro Trp Arg Asn Pro Ala Thr Glu Arg Gln Lys Asp
 65                  70                  75                  80

Leu Tyr Arg Gln Gln Asn Met Asp Asp Val Asp Ser Asp Asp Asp
                    85                  90                  95

Leu Ile Gly Val Pro Val Thr Pro Arg Val Pro Arg Arg Glu Met Thr
                100                 105                 110

Tyr Lys Leu Ala Ile Asp Met Ser His Phe Ile Lys Glu Lys Gly Gly
                115                 120                 125

Leu Gln Gly Met Phe Tyr Ser Arg Arg Arg His Arg Ile Leu Asp Ile
                130                 135                 140

Tyr Leu Glu Lys Glu Glu Gly Ile Ile Pro Asp Trp Gln Asn Tyr Thr
145                 150                 155                 160
```

His Gly Pro Gly Val Arg Tyr Pro Met Tyr Phe Gly Trp Leu Trp Lys
            165                 170                 175

Leu Val Ser Val Glu Leu Ser Gln Glu Ala Glu Asp Glu Ala Asn
    180                 185                 190

Cys Leu Val His Pro Ala Gln Thr Ser Arg His Asp Asp Glu His Gly
            195                 200                 205

Glu Thr Leu Val Trp Gln Phe Asp Ser Met Leu Ala Tyr Asn Tyr Lys
    210                 215                 220

Ala Phe Thr Leu Tyr Pro Glu Glu Phe Gly His Lys Ser Gly Leu Pro
225                 230                 235                 240

Glu Lys Glu Trp Lys Ala Lys Leu Lys Ala Arg Gly Ile Pro Tyr Ser
                245                 250                 255

Glu

<210> SEQ ID NO 290
<211> LENGTH: 240
<212> TYPE: PRT
<213> ORGANISM: Human immunodeficiency virus type 2

<400> SEQUENCE: 290

Met Gly Ser Ala Gly Ser Lys Lys Arg Ser Glu Arg Gln Gln Gly Leu
1               5                   10                  15

Arg Glu Lys Leu Leu Arg Val Pro Glu Arg Pro Tyr Gly Arg Leu Ser
                20                  25                  30

Gly Glu Arg Arg Glu Gln Ser Ser Arg Ser Pro Gly Glu Ser Asp Lys
            35                  40                  45

Asp Leu Asn Ser Pro Ser Cys Glu Gly Gln Asn Ala Arg Gly Ala Glu
    50                  55                  60

Gly Gly Gly Gln Gln Asp Ala Asp Glu Ser Asp Glu Asp Asp Glu Val
65                  70                  75                  80

Gly Ala Ile Cys Lys Thr Pro Ile Val Pro Leu Arg Pro Met Thr Tyr
                85                  90                  95

Lys Leu Ala Val Asp Met Ser His Phe Ile Lys Glu Gln Gly Gly Leu
                100                 105                 110

Glu Gly Met Tyr Tyr Ser Glu Arg Arg His Arg Ile Leu Asp Thr Tyr
            115                 120                 125

Phe Glu Asn Glu Glu Gly Ile Val Ser Gly Trp Gln Asn Tyr Thr His
    130                 135                 140

Gly Pro Gly Ile Arg Tyr Pro Lys Tyr Phe Gly Trp Leu Trp Lys Leu
145                 150                 155                 160

Val Pro Val Glu Val Pro Ala Ala Thr Arg Glu Glu Glu Thr His
                165                 170                 175

Cys Leu Met His Pro Ala Gln Ile Ser Ser Trp Asp Asp Ile His Gly
            180                 185                 190

Glu Thr Leu Ile Trp Gln Phe Asp Ser Leu Leu Ala Tyr Asp Tyr Val
    195                 200                 205

Ala Phe Asn Arg Phe Pro Glu Glu Phe Gly Tyr Gln Ser Gly Leu Pro
210                 215                 220

Glu Glu Glu Trp Lys Ala Arg Leu Lys Ala Arg Gly Ile Pro Thr Asp
225                 230                 235                 240

<210> SEQ ID NO 291
<211> LENGTH: 223
<212> TYPE: PRT
<213> ORGANISM: Simian immunodeficiency virus -continued

<400> SEQUENCE: 291

Met Gly Ser Ser Asn Ser Lys Arg Gln Gln Gln Gly Leu Leu Lys Leu
1               5                   10                  15

Trp Arg Gly Leu Arg Gly Lys Pro Gly Ala Asp Trp Val Leu Leu Ser
            20                  25                  30

Asp Pro Leu Ile Gly Gln Ser Ser Thr Val Gln Glu Cys Gly Lys
        35                  40                  45

Ala Leu Lys Lys Ser Trp Gly Lys Gly Lys Met Thr Pro Asp Gly Arg
    50                  55                  60

Arg Leu Gln Glu Gly Asp Thr Phe Asp Glu Trp Asp Asp Glu Glu
65                  70                  75                  80

Glu Val Gly Phe Pro Val Gln Pro Arg Val Pro Leu Arg Gln Met Thr
                85                  90                  95

Tyr Lys Leu Ala Val Asp Phe Ser His Phe Leu Lys Ser Lys Gly Gly
            100                 105                 110

Leu Asp Gly Ile Tyr Tyr Ser Glu Arg Arg Glu Lys Ile Leu Asn Leu
        115                 120                 125

Tyr Ala Leu Asn Glu Trp Gly Ile Ile Asp Asp Trp Gln Ala Tyr Ser
    130                 135                 140

Pro Gly Pro Gly Ile Arg Tyr Pro Arg Val Phe Gly Phe Cys Phe Lys
145                 150                 155                 160

Leu Val Pro Val Asp Leu His Glu Glu Ala Arg Asn Cys Glu Arg His
                165                 170                 175

Cys Leu Met His Pro Ala Gln Met Gly Glu Asp Pro Asp Gly Ile Asp
            180                 185                 190

His Gly Glu Val Leu Val Trp Lys Phe Asp Pro Lys Leu Ala Val Glu
        195                 200                 205

Tyr Arg Pro Asp Met Phe Lys Asp Met His Glu His Ala Lys Arg
    210                 215                 220

<210> SEQ ID NO 292
<211> LENGTH: 230
<212> TYPE: PRT
<213> ORGANISM: Simian immunodeficiency virus

<400> SEQUENCE: 292

Met Gly Leu Gly Ser Ser Lys Pro Gln His Lys Lys Gln Leu Thr Ile
1               5                   10                  15

Trp Arg Ala Leu His Ala Thr Arg His Thr Arg Tyr Gly Leu Leu Ala
            20                  25                  30

Asp Pro Leu Ile Gly Gln Ser Ser Thr Leu Gln Glu Cys Asp Lys
        35                  40                  45

Gly Leu Arg Lys Ser Leu Ile Arg Lys Arg Asn Gly Asn Met Thr Pro
    50                  55                  60

Glu Gly Arg Arg Leu Gln Asp Gly Asp Gln Trp Asp Glu Trp Ser Asp
65                  70                  75                  80

Glu Glu Asp Glu Val Gly Phe Pro Val Pro Arg Val Pro Leu Arg
                85                  90                  95

Gln Ile Thr Tyr Lys Leu Ala Val Asp Phe Ser His Phe Leu Lys Glu
            100                 105                 110

Lys Gly Gly Leu Asp Gly Ile Tyr Tyr Ser Asp Arg Arg Asn Lys Ile
        115                 120                 125

Leu Asn Leu Tyr Ala Leu Asn Glu Trp Gly Ile Ile Asp Asp Trp Asn
    130                 135                 140

```
Ala Trp Ser Lys Gly Pro Gly Ile Arg Tyr Pro Arg Cys Phe Gly Phe
145                 150                 155                 160

Cys Phe Lys Leu Val Pro Val Ala Leu His Glu Glu Ala Glu Thr Cys
            165                 170                 175

Glu Arg His Cys Leu Val His Pro Ala Gln Leu His Glu Asp Pro Asp
            180                 185                 190

Gly Ile Asn His Gly Glu Ile Leu Ala Trp Lys Phe Asp Pro Met Leu
            195                 200                 205

Ala Val Gln Tyr Asp Pro Ser Arg Glu Tyr Phe Thr Asp Leu Tyr Ser
            210                 215                 220

Thr Val Gly Thr Gly Asn
225                 230

<210> SEQ ID NO 293
<211> LENGTH: 214
<212> TYPE: PRT
<213> ORGANISM: Simian immunodeficiency virus

<400> SEQUENCE: 293

Met Gly Ser Ser Gln Ser Lys Lys Arg Ser Glu Ala Trp Val Arg Tyr
1               5                   10                  15

Ser Ser Ala Leu Arg Gln Leu Val Gly Gly Pro Val Thr Pro Asp Gly
            20                  25                  30

Tyr Lys Gln Ile Glu Ser Ser Gln Gly Ala Glu Lys Gln Ser Leu Leu
            35                  40                  45

Arg Gly Arg Ala Tyr Gly Thr Tyr Ser Glu Gly Leu Asp Lys Val Gln
50                  55                  60

Asn Asp Pro Leu Thr Lys Asp Glu Lys Leu Asp Leu Thr Gln Gln Asp
65                  70                  75                  80

Pro Glu Glu Glu Glu Val Gly Phe Pro Val Cys Arg Gln Val Ser
                85                  90                  95

Leu Arg Val Pro Ser Tyr Lys Asp Leu Ile Asp Phe Ser His Phe Ile
            100                 105                 110

Lys Glu Lys Gly Gly Leu Gly Gly Ile Tyr Tyr Ser Arg Arg Arg Glu
            115                 120                 125

Glu Ile Leu Asp Leu Tyr Ala Glu Asn Glu Trp Gly Phe Glu Pro Gly
            130                 135                 140

Trp Gln Gln Tyr Thr Thr Gly Pro Gly Thr Arg Tyr Pro Lys Thr Phe
145                 150                 155                 160

Gly Phe Leu Phe Lys Leu Glu Pro Val Ser Arg Ala Ile Gly Asp Glu
            165                 170                 175

Tyr Ala Ala Asn Asn His Leu Leu His Ser Ser Gln Leu Cys Pro Gln
            180                 185                 190

Glu Asp Pro Glu Gly Glu Thr Leu Met Trp Ser Gly Thr Leu Ile Leu
            195                 200                 205

Pro Met Thr Leu Gln His
    210

<210> SEQ ID NO 294
<211> LENGTH: 48
<212> TYPE: PRT
```

-continued

```
<213> ORGANISM: Artificial sequence
<220> FEATURE:
<223> OTHER INFORMATION: 76-124 HIV-1 Nef Fragment

<400> SEQUENCE: 294

Leu Arg Pro Met Thr Tyr Lys Ala Ala Val Asp Leu Ser His Phe Leu
1               5                   10                  15

Lys Glu Lys Gly Gly Leu Glu Gly Leu Ile His Ser Gln Arg Arg Gln
            20                  25                  30

Asp Ile Leu Asp Leu Trp Ile Tyr His Thr Gln Gly Tyr Phe Pro Asp
        35                  40                  45
```

MUTATED HIV NEF FOR MODULATING IMMUNITY

The present invention relates to the use of the immunosuppressive function of an accessory protein of the human or simian immunodeficiency virus for the preparation of a vaccine. In particular, the present invention relates to vaccine compositions comprising a Nef protein.

Although more than 20 years of scientific research have been devoted to finding a vaccine against HIV (Human Immunodeficiency Virus), a convincing prophylactic means to fight HIV is still awaiting to be discovered. Thus, more than 20 clinical trials of anti-HIV vaccines have been launched, and as of today, none of them has shown sufficient efficacy in preventing infections.

Nef (negative regulatory factor), is a 27 to 35 kDa regulatory protein of HIV or SIV. Among its various functions, Nef is in particular involved in the down-regulation of the expression of Class I MHC (Major Histocompatibility Complex) molecules (MHC-I) of the A and B types in humans (HLA-A and HLA-B). This property of Nef has been shown to be sensitive to mutations, however, mutations of HIV-1 Nef at the amino acid position 93 have proved inefficient at modulating its MHC-I down-regulation properties (Ali et al. (2003) *J. Immunol.* 171:3999-4005). Nef is also involved in the down-regulation of CD4 molecules normally expressed at the surface of T helper cells. Furthermore, Nef also down-regulates the expression of mature Class II MHC molecules and up-regulates the expression of immature Class II MHC molecules. All these regulations are a consequence of Nef interference with normal cellular trafficking and in particular with the endocytosis-degradation pathway (Le Gall et al. (1998) *Immunity* 8:483-495).

Nef, as one of the antigens of HIV or SIV, has been included in several vaccine compositions, alone or in combination with other antigens, such as described, for example, in WO 01/00232 or in WO 03/011334. However, these approaches have not been demonstrated to be effective either. The lack of an effective immune response against HIV or SIV, as a result of Nef administration, might relate to an as yet unidentified function of Nef, whereas generation of an active vaccine against HIV or SIV most probably requires an effective immune response to be raised against Nef.

Thus, an object of the present invention is to relate immunosuppressive properties of HIV or SIV to the Nef protein.

Another object of the invention relates to the identification of an immunosuppressive domain in the Nef protein.

A further object of the invention is to provide pharmaceutical or vaccine compositions comprising a modified Nef protein.

The present invention relates to the use, in particular to the in vitro or to the ex vivo use, of a mutation of at least one amino acid in the immunosuppressive domain of a Nef protein, for modulating the immunosuppressive property of said protein.

In vivo, the Nef protein is in particular found in HIV (such as HIV-1 or HIV-2) infected individuals or in SIV infected apes.

As intended herein, a mutation either relates to the substitution, the insertion or the deletion of at least one amino acid purposely brought to a Nef protein, or to the naturally occurring substitution, insertion or deletion of at least one amino acid in a given Nef protein with respect to the majority of Nef proteins (i.e. at least about 80% of the identified Nef proteins).

According to the invention, a given protein is said to hold an immunosuppressive property, if it is liable to inhibit the immune system of an organism in which it is present. In particular, the immunosuppressive property of said given protein can be measured by following the general procedure described in Mangeney & Heidmann (1998) *Proc. Natl. Acad. Sci. U.S.A.* 95:14920-5 and Mangeney et al. (2001) *J. Gen. Virol.* 82:2515-8. That is, stable tumor cell lines expressing, or in particular excreting, said given protein in the intra- or extracellular space are established and engrafted onto mice, and the size of the tumors ($A_{protein}$) is compared, after several days, to the size of tumors ($A_{none}$) obtained from mice engrafted with tumor cell lines which do not express, or in particular excrete, said given protein. If the size of the tumors which express, or in particular excrete, the given protein is significantly greater than the size of the non-expressing, or in particular the non-excreting tumors, the given protein is said to be immunosuppressive. The immunosuppressive property of a given protein can also be characterized by its immunosuppression index [$(A_{protein}-A_{none})/A_{none}$]. If the immunosuppression index of a given protein is positive then the given protein is said to be immunosuppressive, and if its immunosuppression index is equal to zero or negative, the given protein is said to have essentially no immunosuppressive activity.

The present invention results from the relation which has been established by the Inventors between the immunosuppressive properties of HIV or SIV and the Nef protein. In other terms, the present invention results from the identification of the immunosuppressive function of the Nef protein, which is furthermore shown to be both an intra and an extracellular function. Further, the Inventors have shown that the immunosuppressive function of Nef is independent from the Nef-induced downregulation of CD4 or MHC-I.

Thus, in a preferred embodiment, the invention relates to the use of a mutation of at least one amino acid in the immunosuppressive domain of a Nef protein, for modulating the immunosuppressive property of said protein, provided that the resulting mutated protein presents substantially preserved CD4 and/or MHC-I down-regulation functions with respect to the non-mutated Nef protein.

As intended herein the expression "substantially preserved CD4 and/or MHC-I down-regulation functions" means that at least 60%, in particular at least 80% of the CD4 and/or MHC-I downregulation functions of a given Nef protein is preserved in the corresponding Nef protein carrying a mutation according to the invention.

The donwregulation of CD4 and MHC-I can be determined by measuring the fluorescence of CD4 or MHC-I expressing cells transformed with increasing amounts of nucleic acids encoding said given protein and contacted with fluorescent anti-CD4 or anti-MHC-I antibodies. Such methods are well known to the man skilled in the art and are in particular described in the following examples.

The immunosuppressive domain of an immunosuppressive protein is defined as being the region of said protein which is responsible for conferring its immunosuppressive activity to said protein and, in particular, it is constituted of all the amino acids, the mutation of which is liable to modulate the immunosuppressive property of said protein.

As intended herein, the expression "modulating the immunosuppressive property" of a given protein relates to an increase or a decrease in the immunosuppressive property of said protein.

In a preferred embodiment, the invention relates to the above defined use of a mutation of at least one amino acid in the immunosuppressive domain of a Nef protein, for inhibiting the immunosuppressive property of said protein. According to this embodiment the Nef protein presents an imunosuppressive property.

As intended in the present invention, the inhibiting of the immunosuppressive property of a given protein, yields a protein with substantially no immunosuppressive activity, that is having an immunosuppression index equal to zero or negative.

Nef proteins devoid of immunosuppressivity are particularly advantageous for the manufacture of anti-HIV or anti-SIV vaccines. Indeed, vaccine compositions containing Nef proteins devoid of immunosuppressivity according to the present invention are particularly effective at preventing HIV or SIV infections since they potently stimulate the immune response and in particular the production of antibodies directed against the Nef protein and the elicitation of a cellular immune response against infected cells which express the Nef protein. This stimulation of the immune response therefore prevents the subsequent immunosuppressive action of Nef when it is liberated in the organism or expressed by infected cells during the initial steps of HIV or SIV infection. Thus, the absence of immunosuppression conveyed by the Nef protein, which results from the immune response elicited against Nef, prevents the HIV or SIV precocious infectious cycles from being effective and favour the elimination of the virus by the immune system.

In particular, vaccine compositions according to the invention are more effective than Nef-containing compositions of the prior art to induce an anti-HIV or anti-SIV response from the immune system, since it is herein disclosed that non-mutated Nef is in itself an inhibitor of the immune system.

In another preferred embodiment, the invention relates to the above defined use, to obtain a Nef protein mutated in its immunosuppressive domain, or a fragment thereof, provided said fragment comprises the mutated immunosuppressive domain of said Nef protein, for the manufacture of a medicament or a vaccine intended for the prevention and/or the treatment of viral diseases.

As intended herein, viral diseases encompass all diseases or syndromes resulting from a viral infection, such as AIDS for instance. Besides, vaccines according to the invention are meant to be used prophylactically or therapeutically.

In yet another preferred embodiment, the invention relates to the above defined use, wherein the structure of the Nef protein is substantially preserved.

The substantial preservation of the structure of a Nef protein mutated in its immunosuppressive domain with respect to its natural counterpart can be for instance determined by comparing the circular dichroism spectra, the RMN spectra, the X-ray diffraction pattern, or any other physicochemical property of said mutated Nef protein with that of the natural Nef protein from which it derives, according to methods well known to the man skilled in the art. It is to be noted that, as intended herein, the natural Nef protein from which the mutated Nef protein is deriving presents an immunosuppressive activity.

In a further preferred embodiment, the invention relates to the above defined use, wherein the epitopes, in particular the conformational epitopes, of the Nef protein are substantially preserved. In particular, B-cell epitopes as well as T-cell epitopes are preserved.

More particularly, the invention relates to the above defined use, wherein the epitopes, in particular the conformational epitopes, located outside of the immunosuppressive domain of the Nef protein are substantially preserved.

The substantial preservation of the epitopes for a Nef protein mutated in its immunosuppressive domain, with respect to its natural counterpart, can be for instance determined by checking that antibodies known to bind to a natural Nef protein, also bind to the corresponding Nef mutant.

In another further preferred embodiment, the invention relates to the above defined use, wherein the intracellular functional properties of the Nef protein other than its immunosuppressive properties are substantially preserved.

More preferably, the invention relates to the above defined use, wherein the CD4 and/or MHC-I down-regulation functions of the Nef protein are substantially preserved.

The intracellular functional properties of the Nef protein other than its immunosuppressive properties relate to the non-immunosuppressive functions of the protein which are only operative when said protein is hosted inside a cell. Such functions notably comprise the down-regulation of CD4 and MHC-I expression.

The down-regulation of CD4 and MHC-I expression by a given protein can be determined by measuring the fluorescence of CD4 or MHC-I expressing cells transformed with increasing amounts of nucleic acids encoding said given protein and contacted with fluorescent anti-CD4 or anti-MHC-I antibodies. Such methods are well known to the man skilled in the art and are in particular described in the following examples.

The present invention also relates to a process for cancelling the immunosuppressive property of a Nef protein, comprising:
mutating the immunosuppressive domain of said Nef protein by deletion, substitution or insertion of at least one amino acid,
checking the cancelling of said immunosuppressive activity by an in vivo immunosupressivity assay, The in vivo immunosuppressivity assay corresponds to the above described assay.

A preferred embodiment of the above mentioned process comprises a further step of checking that the structure and/or the epitopes, in particular the epitopes located outside the immunosuppressive domain, of the Nef protein are substantially preserved.

Another preferred embodiment of the above mentioned process comprises a further step of checking that the structure and/or the epitopes, in particular the epitopes located outside the immunosuppressive domain, and/or the CD4 and/or MHC-I down-regulation functions, of the Nef protein are substantially preserved.

The substantial preservation of the structure and/or the epitopes, and/or the CD4 and/or MHC-I down-regulation functions, of the Nef protein can be determined as described above.

The present invention relates in particular to a pharmaceutical or vaccine composition, comprising as active substance, a protein or a polypeptide comprising or being constituted of a Nef protein or a fragment thereof, wherein
  the immunosuppressive domain of said Nef protein is mutated by deletion, substitution and/or insertion of at least one amino acid, provided that said Nef protein has substantially no immunosuppressive activity, and
  said fragment comprises the mutated immunosuppressive domain of said Nef protein and has substantially no immunosuppressive activity,
in association with a pharmaceutically acceptable carrier.

In particular, the sequences adjacent to the respective N-terminal and C-terminal ends of said fragment can be identical to the sequences adjacent to the respective N-terminal end and C-terminal end of said fragment in the Nef protein from which it derives.

In a particular embodiment of the above mentioned pharmaceutical or vaccine composition the protein or polypeptide comprising a fragment of Nef protein is such that the sequences adjacent to the respective N-terminal and/or C-terminal end of said fragment are different from the sequences adjacent to the respective N-terminal end and/or C-terminal end of said fragment in the Nef protein from which it derives.

More particularly, in another embodiment of the above mentioned pharmaceutical or vaccine composition, the protein or polypeptide comprising a fragment of Nef protein is such that:
- the sequence adjacent to the N-terminal end of said fragment is different from the sequences adjacent to the N-terminal end of said fragment in the Nef protein from which it derives, or
- the sequence adjacent to the C-terminal end of said fragment is different from the sequences adjacent to the C-terminal end of said fragment in the Nef protein from which it derives, or
- the sequence adjacent to the respective N-terminal and C-terminal ends of said fragment are different from the sequences adjacent to the respective N-terminal and C-terminal ends of said fragment in the Nef protein from which it derives.

The mutated Nef protein or fragment thereof according to the invention is said to be immunosuppressive deficient.

The present invention also relates to a pharmaceutical or vaccine composition, comprising as active substance, a protein or a polypeptide comprising or being constituted of a Nef protein or a fragment thereof, wherein
- the immunosuppressive domain of said Nef protein is mutated by deletion, substitution and/or insertion of at least one amino acid, provided that said Nef protein has substantially no immunosuppressive activity and that the CD4 and/or MHC-I down-regulation functions, of the Nef protein are substantially preserved, and
- said fragment comprises the mutated immunosuppressive domain of said Nef protein and has substantially no immunosuppressive activity, in association with a pharmaceutically acceptable carrier.

In a preferred embodiment of the above defined pharmaceutical or vaccine composition, the sequence of the mutated immunosuppressive domain of the Nef protein is comprised in the amino acid sequence extending from the N-terminus of the first α helix to the C-terminus of the second α helix of the Nef protein.

The structure of the Nef protein is in particular described in Arold et al. (1997) *Structure* 5:1361-72 and in Grzesiek et al. (1997) *Protein Science* 6:1248-63. The nomenclature of the secondary structure elements of the Nef protein, and in particular of its α helices, is based on the structural description of the core domain of the Nef protein, according to Arold et al. (1997) and Grzesiek et al. (1997).

In another preferred embodiment of the above defined pharmaceutical or vaccine composition, the sequence of the mutated immunosuppressive domain of the Nef protein is comprised in a sequence ranging from the amino acid at position 80 to the amino acid at position 150, particularly from the amino acid at position 81 to the amino acid at position 140, of the sequence of said Nef protein, and in particular:
- in a sequence ranging from the amino acid at position 80 to the amino acid at position 120, more particularly from the amino acid at position 81 to the amino acid at position 118, of the sequence of a HIV-1 Nef protein, or
- in a sequence ranging from the amino acid at position 104 to the amino acid at position 150, in particular from the amino acid at position 104 to the amino acid at position 140, of the sequence of a HIV-2 Nef protein.

Nef protein sequences can be easily accessed by the man skilled in the art. By way of example, several HIV-1, HIV-2 or SIV Nef protein sequences are presented in FIG. 4.

More preferably, in the above defined pharmaceutical or vaccine composition, the sequence of the mutated immunosuppressive domain of the HIV-1 Nef protein is comprised in a sequence ranging from the amino acid at position 90 to the amino acid at position 113, in particular from the amino acid at position 90 to the amino acid at position 112, of the sequence of said Nef protein.

In a particular embodiment of the above defined pharmaceutical or vaccine composition, the sequence of the mutated immunosuppressive domain of the Nef protein is comprised in a sequence which is homologous to the amino acid sequence ranging from the amino acid at position 80 to the amino acid at position 120 of SEQ ID NO: 1, in particular from the amino acid at position 81 to the amino acid at position 117 of SEQ ID NO: 1, more particularly from the amino acid at position 90 to the amino acid at position 112 of SEQ ID NO: 1.

SEQ ID NO: 1 corresponds to the amino acid sequence of the Nef protein described by Wain-Hobson et al. (1985) *Cell* 40:9-17 (HIV-1 strain LAI).

According to the invention, two sequences are said to be homologous if they can be aligned by using an algorithm such as defined in Altschul et al., *Nucleic Acids Res.* (1997) 25:3389 or by using the Clustal W software, well known from the man skilled in the art and described in Thompson et al., *Nucleic Acids Res.* (1994) 22:4673-4680, for instance.

In particular, two sequences are said to be homologous if the amino acid identity percentage between said two sequences is equal to or larger than about 35%.

By way of example, FIG. 4 represents a sequence alignment of several Nef proteins originating from HIV-1, HIV-2 or SIV, as obtained with the Clustal W software. Sequences homologous to the amino acid sequence ranging from the amino acid at position 81 to the amino acid at position 118 of SEQ ID NO: 1 are boxed.

In another particular embodiment of the above defined pharmaceutical or vaccine composition, the sequence of the mutated immunosuppressive domain of the Nef protein is comprised in a 26 or 27 amino acid-long sequence of said Nef protein, the N-terminal end of said 26 or 27 amino acid-long sequence being the pentapeptide $AX_1DX_2S$ and the C-terminal end of said 26 or 27 amino acid-long sequence being the amino acid L, in which $X_1$ represents any amino acid, and in particular I, V, L, F, or R, and $X_2$ represents any amino acid, and in particular M, L, or F.

Examples of such sequences are presented in FIG. 4.

In yet another particular embodiment of the invention, the above defined pharmaceutical or vaccine composition comprises as active substance a protein or polypeptide comprising or being constituted of a Nef protein or a fragment thereof comprising the following sequence:

$AX_1DX_2SX_3X_4X_5KX_6X_7GX_8LX_9G$ (SEQ ID NO: 3)

wherein
$X_1$ represents I, L, V, F, or R,
$X_2$ represents M, L, or F,
$X_3$ represents H, D, or F,
$X_4$ represents F or L,
$X_5$ represents I or L, $X_6$ represents any amino acid different from E, in particular R, $X_7$ represents K, Q, or R, $X_8$ represents G or no amino acid, $X_9$ represents E, D, or R.

SEQ ID NO: 3 comprises the immunosuppressive domain of Nef.

Examples of such sequences are presented in FIG. 4.

According to a particularly preferred embodiment of the invention, the above defined pharmaceutical or vaccine composition comprises as active substance a protein or polypeptide comprising or being constituted of a Nef protein or a fragment thereof, wherein the amino acid homologous to the amino acid at position 93 of SEQ ID NO: 1 is replaced by any amino acid different from E, in particular by W, F, M, Y, R, H or K, more particularly by R, H, or K, and preferably by R.

The amino acid homologous to the amino acid at position 93 of SEQ ID NO: 1 can be determined by aligning the sequence of the above mentioned protein or polypeptide with SEQ ID NO: 1 (for instance using the Clustal W software) and by selecting the amino acid which is aligned with the amino acid at position 93 of SEQ ID NO: 1. By way of example FIG. 4 represents the amino acid homologous to the amino acid at position 93 of SEQ ID NO: 1 for several Nef proteins originating from HIV-1, HIV-2 or SIV. Advantageously, the single substitution of the amino acid homologous to the amino acid at position 93 of SEQ ID NO: 1 amino acid yields Nef mutants substantially devoid of immunosuppressivity.

According to another particularly preferred embodiment of the invention, the above defined pharmaceutical or vaccine composition comprises as active substance, a protein or polypeptide comprising or being constituted of a HIV-1 Nef protein or a fragment thereof, wherein the amino acid at position 93 of the sequence of said HIV-1 Nef protein is replaced by any amino acid different from E, in particular by W, F, M, Y, R, H or K, more particularly by R, H, or K, and preferably by R.

According to yet another particularly preferred embodiment of the invention, the above defined pharmaceutical or vaccine composition comprises as active substance a Nef protein, wherein the amino acid homologous to the amino acid at position 93 of SEQ ID NO: 1 is replaced by any amino acid different from E, in particular by W, F, M, Y, R, H or K, more particularly by R, H, or K, and preferably by R.

By way of example, as depicted in FIG. 6B, the position homologous to the position 93 of HIV-1 Nef corresponds to position 125 in SIV strain mac239 Nef (SEQ ID NO: 22) and the substitution of the E at position 125 in SIV strain mac239 Nef by R yields an immunosuppressive-deficient Nef mutant (SEQ ID NO: 23).

According to a most preferred embodiment of the invention, the above defined pharmaceutical or vaccine composition comprises as active substance a mutated Nef protein corresponding to SEQ ID NO: 2.

In yet another preferred embodiment of the invention, the above defined pharmaceutical or vaccine composition is characterized in that when a Nef protein is comprised in said pharmaceutical or vaccine composition, the structure of the Nef protein is substantially preserved.

In a further preferred embodiment of the invention, the above defined pharmaceutical or vaccine composition is characterized in that when a Nef protein is comprised in said pharmaceutical or vaccine composition, the epitopes, such as B cell or T cell epitopes, in particular the conformational epitopes, of the Nef protein are substantially preserved.

More particularly, the invention relates to the above defined pharmaceutical or vaccine composition, wherein the epitopes, in particular the conformational epitopes, located outside of the imnmunosuppressive domain of the Nef protein are substantially preserved.

In another further preferred embodiment of the invention, the above defined pharmaceutical or vaccine composition is characterized in that when a Nef protein is comprised in said pharmaceutical or vaccine composition, the intracellular functional properties other than the immunosuppressive properties of the Nef protein are substantially preserved.

More preferably, the invention relates to the above defined pharmaceutical or vaccine composition, wherein the CD4 and/or MHC-I down-regulation functions of the Nef protein are substantially preserved.

The present invention also relates to the protein or polypeptide as defined in the above mentioned pharmaceutical or vaccine composition.

In particular, the present invention relates to a protein represented by SEQ ID NO: 2 or SEQ ID NO: 31.

The present invention also relates to a pharmaceutical or vaccine composition, comprising as active substance a nucleic acid encoding a protein or polypeptide such as defined above.

The present invention also relates to the nucleic acid sequences coding for the protein or the polypeptide as defined in the above mentioned pharmaceutical or vaccine composition.

In particular, the present invention relates to a nucleic acid sequence coding for a protein represented by SEQ ID NO: 2 or SEQ ID NO: 31.

The present invention also relates to the use of a protein or a polypeptide as defined above, or of a nucleic acid as defined above, for the manufacture of a medicament or a vaccine intended for the prevention and/or the treatment of viral diseases, such as HIV infections.

In a preferred embodiment of the invention, the above defined medicament, or the above defined pharmaceutical or vaccine composition comprising a protein or a polypeptide as defined above as active substance, also comprise at least one HIV protein or lipopeptide, or a fragment thereof, in particular selected from gp41, gp120, gp140, gp160, Env, Gag, Pol, Rev, RT, Vpu or Tat.

In a preferred embodiment of the invention, the above defined medicament, or the above defined pharmaceutical or vaccine composition comprising as active substance a nucleic acid encoding a protein or polypeptide such as defined above, also comprise at least one nucleic acid encoding a HIV protein, or a fragment thereof, in particular selected from a nucleic acid encoding gp120, gp140, gp160, Env, Gag, Pol, Rev, RT, Vpu or Tat.

In another preferred embodiment of the above defined medicament, or the above defined pharmaceutical or vaccine composition comprising as active substance a nucleic acid encoding a protein or polypeptide such as defined above, the nucleic acid is naked or comprised in a vector, in particular selected from a canarypox viral vector, an adenoviral vector, or a measles viral vector.

The present invention also relates to the use of a protein or a polypeptide as defined above, for the preparation of:

- polyclonal or monoclonal antibodies, or fragments thereof, such as Fab or $F(ab)'_2$ fragments, directed against said protein or polypeptide as defined above,
- scFv polypeptides directed against said protein or polypeptide as defined above,
- aptamers directed against said protein or polypeptide as defined above,
- binding peptides directed against said protein or polypeptide as defined above.

The procedures for the preparation of the above mentioned antibodies or fragments of antibodies, scFv polypeptides, aptamers, or binding peptides, are particularly well known to the man skilled in the art. As regards binding peptides, they can also be prepared according to methods well known to the man skilled in the art, such as ribosome or phage display methods.

The present invention also relates to antibodies or fragments thereof, scFv polypeptides, aptamers, or binding peptides, directed against the above defined proteins or polypeptides involved in the invention, provided that said antibodies or fragments thereof, scFv polypeptides, or aptamers do not bind to proteins or polypeptides different from the above defined proteins or polypeptides involved in the invention.

As intended herein, the above defined antibodies or fragments thereof, scFv polypeptides, aptamers, or binding peptides, bind specifically to the proteins or the polypeptides according to the invention, in other words they are specific ligands for the proteins or the polypeptides according to the invention. In particular, the specificity of these ligands is such that they bind to the proteins or polypeptides according to the invention, but not to the proteins from which said proteins or polypeptides according to the invention are derived by mutation.

The present invention also relates to a method for preparing mutants of a Nef protein, wherein:
in a first step, the sequence ranging from the amino acid at position 80 to the amino acid at position 150 of the sequence said Nef protein is mutated by deletion, insertion or substitution of at least one amino acid,
in a second step, the immunosuppressive properties of the mutated Nef protein obtained in the first step are checked and mutants lacking immunosuppressive properties are selected.

The mutants obtained according to this method are immunosuppressive-deficient mutants.

In a preferred embodiment of the above defined method for preparing mutants of a Nef protein, in a third step the CD4 and/or MHC-I downregulation functions of the mutated Nef protein obtained in the second step are checked and mutated Nef proteins having substantially preserved CD4 and/or MHC-I downregulation functions with respect to said Nef protein are selected.

In another preferred embodiment of the above defined method for preparing mutants of a Nef protein, the mutated sequence ranges:
from the amino acid at position 80 to the amino acid at position 120, more particularly from the amino acid at position 90 to the amino acid at position 112, of the sequence of a HIV-1 protein, or
from the amino acid at position 104 to the amino acid at position 150 of the sequence of a HIV-2 Nef protein.

In another preferred embodiment of the above defined method for preparing mutants of a Nef protein, the sequence of the Nef protein is mutated by directed mutagenesis of the nucleic acid sequence coding for said Nef protein.

In another preferred embodiment of the above defined method for preparing mutants of a Nef protein, the immunosuppressive properties of the mutated Nef protein are checked according to the general procedure described in Mangeney & Heidmann (1998) *Proc. Natl. Acad. Sci. U.S.A.* 95:14920-5 and Mangeney et al. (2001) *J. Gen. Virol.* 82:2515-8 as defined above, in particular the above-defined immunosuppression index is measured and mutated Nef protein having immunosuppression indexes equal to zero or negative are selected.

The down-regulation of CD4 and MHC-I expression by a given protein can be determined by measuring the fluorescence of CD4 or MHC-I expressing cells transformed with increasing amounts of nucleic acids encoding said given protein and contacted with fluorescent anti-CD4 or anti-MHC-I antibodies. Such methods are well known to the man skilled in the art and are in particular described in the following examples.

The present invention also relates to the mutants of a Nef protein liable to be prepared by the above defined method and to pharmaceutical compositions comprising said mutants of a Nef protein in association with a pharmaceutically acceptable carrier.

The present invention also relates to a new protein or polypeptide comprising or being constituted by the immunosuppressive domain of a Nef protein, provided that if present, the sequences adjacent to the respective N-terminal end and/or C-terminal end of the immunosuppressive domain in said protein or polypeptide are different from the sequences adjacent to the respective N-terminal end and/or C-terminal end of the immunosuppressive domain in the Nef protein from which it derives.

More particularly, in an embodiment of the above defined new protein or polypeptide:
the sequence adjacent to the N-terminal end of the immunosuppressive domain is different from the sequences adjacent to the N-terminal end of the immunosuppressive domain in the Nef protein from which it derives, or
the sequence adjacent to the C-terminal end of the immunosuppressive domain is different from the sequences adjacent to the C-terminal end of the immunosuppressive domain in the Nef protein from which it derives, or
the sequence adjacent to the respective N-terminal and C-terminal ends of the immunosuppressive domain are different from the sequences adjacent to the respective N-terminal and C-terminal ends of the immunosuppressive domain in the Nef protein from which it derives.

In a particular embodiment of the present invention, the new protein or polypeptide as defined above presents CD4 and/or MHC-I down-regulation functions.

The Nef immunosuppressive domain which constitutes or is comprised in the above defined new protein or polypeptide can be either mutated or not with respect to the immunosuppressive domain of naturally occurring Nef proteins.

Thus, the new protein or polypeptide as defined above can be immunosuppressive, in the general case, if the Nef immunosuppressive domain which it comprises or which it is constituted of, derives without mutations from a naturally occurring Nef protein, which generally presents immunosuppressive properties.

The new protein or polypeptide can also comprise or be constituted of a Nef immunosuppressive domain which is mutated with respect to its natural form. This mutation can either be silent as concerns the immunosuppressive properties of the Nef immunosuppressive domain, which means, in the general case, that it does not affect the immunosuppressive properties of the Nef immunosuppressive domain, or the mutation can render the immunosuppressive domain immunosuppressive-deficient, as is the case for the above-mentioned mutations affecting Nef immunosuppressive domain.

Further, in certain particular cases, the immunosuppressive domain can also derive from naturally occuring Nef variants devoid of immunosuppressive properties.

In a preferred embodiment of the above defined new protein or polypeptide, the sequence of the immunosuppressive domain of the Nef protein is comprised in the amino acid sequence extending from the N-terminus of the first α helix to the C-terminus of the second α helix of the Nef protein.

In another preferred embodiment of the above defined new protein or polypeptide, the sequence of the immunosuppressive domain of the Nef protein is comprised in a sequence ranging from the amino acid at position 80 to the amino acid at position 150, particularly from the amino acid at position 81 to the amino acid at position 140, of the sequence of said Nef protein, and in particular:

- in a sequence ranging from the amino acid at position 80 to the amino acid at position 120, more particularly from the amino acid at position 81 to the amino acid at position 118, of the sequence of a HIV-1 Nef protein
- in a sequence ranging from the amino acid at position 104 to the amino acid at position 150, in particular from the amino acid at position 104 to the amino acid at position 140, of the sequence of a HIV-2 Nef protein.

More preferably, in the above defined new protein or polypeptide, the sequence of the immunosuppressive domain of the HIV-1 Nef protein is comprised in a sequence ranging from the amino acid at position 90 to the amino acid at position 113, in particular from the amino acid at position 90 to the amino acid at position 112, of the sequence of said Nef protein.

In another preferred embodiment of the above defined new protein or polypeptide, the sequence of the immunosuppressive domain of the Nef protein is comprised in a sequence which is homologous to the amino acid sequence ranging from the amino acid at position 80 to the amino acid at position 120 of SEQ ID NO: 1, in particular from the amino acid at position 81 to the amino acid at position 117 of SEQ ID NO: 1, more particularly from the amino acid at position 90 to the amino acid at position 112 of SEQ ID NO: 1.

In a particularly preferred embodiment of the above defined new protein or polypeptide, the sequence of the immunosuppressive domain of the Nef protein is comprised in a 26 or 27 amino acid-long sequence, the N-terminal end of said Nef protein, the N-terminal end of said 26 or 27 amino acid-long sequence being the pentapeptide $AX_1DX_2S$ and the C-terminal end of said 26 or 27 amino acid-long sequence being the amino acid L, in which $X_1$ represents any amino acid, and in particular I, V, L, F, or R, and $X_2$ represents any amino acid, and in particular M, L, or F.

In a preferred embodiment of the present invention, the Nef immunosuppressive domain which constitutes or is comprised in the above defined new protein or polypeptide is not mutated, such a domain is said to be non-mutated, and is derived from a naturally immunosuppressive Nef protein. Advantageously, the new protein or polypeptide which comprises or is constituted of such a non-mutated domain is immunosuppressive.

In another preferred embodiment, the new protein or polypeptide is constituted of one of the following HIV-1 Nef fragments:

| | | |
|---|---|---|
| 80-120 | TYKAAVDLSHFLKEKGGLEGLIHSQR-RQDILDLWIYHTQGY | (SEQ ID NO: 32) |
| 81-120 | YKAAVDLSHFLKEKGGLEGLIHSQRRQDILDLWIYHTQGY | (SEQ ID NO: 33) |
| 82-120 | KAAVDLSHFLKEKGGLEGLIHSQRRQDILDLWIYHTQGY | (SEQ ID NO: 34) |
| 83-120 | AAVDLSHFLKEKGGLEGLIHSQRRQDILDLWIYHTQGY | (SEQ ID NO: 35) |
| 84-120 | AVDLSHFLKEKGGLEGLIHSQRRQDILDLWIYHTQGY | (SEQ ID NO: 36) |
| 85-120 | VDLSHFLKEKGGLEGLIHSQRRQDILDLWIYHTQGY | (SEQ ID NO: 37) |
| 86-120 | DLSHFLKEKGGLEGLIHSQRRQDILDLWIYHTQGY | (SEQ ID NO: 38) |
| 87-120 | LSHFLKEKGGLEGLIHSQRRQDILDLWIYHTQGY | (SEQ ID NO: 39) |
| 88-120 | SHFLKEKGGLEGLIHSQRRQDILDLWIYHTQGY | (SEQ ID NO: 40) |
| 89-120 | HFLKEKGGLEGLIHSQRRQDILDLWIYHTQGY | (SEQ ID NO: 41) |
| 90-120 | FLKEKGGLEGLIHSQRRQDILDLWIYHTQGY | (SEQ ID NO: 42) |
| 80-119 | TYKAAVDLSHFLKEKGGLEGLIHSQRRQDILDLWIYHTQG | (SEQ ID NO: 43) |
| 81-119 | YKAAVDLSHFLKEKGGLEGLIHSQRRQDILDLWIYHTQG | (SEQ ID NO: 44) |
| 82-119 | KAAVDLSHFLKEKGGLEGLIHSQRRQDILDLWIYHTQG | (SEQ ID NO: 45) |
| 83-119 | AAVDLSHFLKEKGGLEGLIHSQRRQDILDLWIYHTQG | (SEQ ID NO: 46) |
| 84-119 | AVDLSHFLKEKGGLEGLIHSQRRQDILDLWIYHTQG | (SEQ ID NO: 47) |
| 85-119 | VDLSHFLKEKGGLEGLIHSQRRQDILDLWIYHTQG | (SEQ ID NO: 48) |
| 86-119 | DLSHFLKEKGGLEGLIHSQRRQDILDLWIYHTQG | (SEQ ID NO: 49) |
| 87-119 | LSHFLKEKGGLEGLIHSQRRQDILDLWIYHTQG | (SEQ ID NO: 50) |
| 88-119 | SHFLKEKGGLEGLIHSQRRQDILDLWIYHTQG | (SEQ ID NO: 51) |
| 89-119 | HFLKEKGGLEGLIHSQRRQDILDLWIYHTQG | (SEQ ID NO: 52) |
| 90-119 | FLKEKGGLEGLIHSQRRQDILDLWIYHTQG | (SEQ ID NO: 53) |
| 80-118 | TYKAAVDLSHFLKEKGGLEGLIHSQRRQDILDLWIYHTQ | (SEQ ID NO: 54) |

```
81-118   YKAAVDLSHFLKEKGGLEGLIHSQRRQDILDLWIYHTQ    (SEQ ID NO: 55)
82-118   KAAVDLSHFLKEKGGLEGLIHSQRRQDILDLWIYHTQ     (SEQ ID NO: 56)
83-118   AAVDLSHFLKEKGGLEGLIHSQRRQDILDLWIYHTQ      (SEQ ID NO: 57)
84-118   AVDLSHFLKEKGGLEGLIHSQRRQDILDLWIYHTQ       (SEQ ID NO: 58)
85-118   VDLSHFLKEKGGLEGLIHSQRRQDILDLWIYHTQ        (SEQ ID NO: 59)
86-118   DLSHFLKEKGGLEGLIHSQRRQDILDLWIYHTQ         (SEQ ID NO: 60)
87-118   LSHFLKEKGGLEGLIHSQRRQDILDLWIYHTQ          (SEQ ID NO: 61)
88-118   SHFLKEKGGLEGLIHSQRRQDILDLWIYHTQ           (SEQ ID NO: 62)
89-118   HFLKEKGGLEGLIHSQRRQDILDLWIYHTQ            (SEQ ID NO: 63)
90-118   FLKEKGGLEGLIHSQRRQDILDLWIYHTQ             (SEQ ID NO: 64)
80-117   TYKAAVDLSHFLKEKGGLEGLIHSQRRQDILDLWIYHT    (SEQ ID NO: 65)
81-117   YKAAVDLSHFLKEKGGLEGLIHSQRRQDILDLWIYHT     (SEQ ID NO: 66)
82-117   KAAVDLSHFLKEKGGLEGLIHSQRRQDILDLWIYHT      (SEQ ID NO: 67)
83-117   AAVDLSHFLKEKGGLEGLIHSQRRQDILDLWIYHT       (SEQ ID NO: 68)
84-117   AVDLSHFLKEKGGLEGLIHSQRRQDILDLWIYHT        (SEQ ID NO: 69)
85-117   VDLSHFLKEKGGLEGLIHSQRRQDILDLWIYHT         (SEQ ID NO: 70)
86-117   DLSHFLKEKGGLEGLIHSQRRQDILDLWIYHT          (SEQ ID NO: 71)
87-117   LSHFLKEKGGLEGLIHSQRRQDILDLWIYHT           (SEQ ID NO: 72)
88-117   SHFLKEKGGLEGLIHSQRRQDILDLWIYHT            (SEQ ID NO: 73)
89-117   HFLKEKGGLEGLIHSQRRQDILDLWIYHT             (SEQ ID NO: 74)
90-117   FLKEKGGLEGLIHSQRRQDILDLWIYHT              (SEQ ID NO: 75)
80-116   TYKAAVDLSHFLKEKGGLEGLIHSQRRQDILDLWIYH     (SEQ ID NO: 76)
81-116   YKAAVDLSHFLKEKGGLEGLIHSQRRQDILDLWIYH      (SEQ ID NO: 77)
82-116   KAAVDLSHFLKEKGGLEGLIHSQRRQDILDLWIYH       (SEQ ID NO: 78)
83-116   AAVDLSHFLKEKGGLEGLIHSQRRQDILDLWIYH        (SEQ ID NO: 79)
84-116   AVDLSIWLKEKGGLEGLIHSQRRQDILDLWIYH         (SEQ ID NO: 80)
85-116   VDLSHFLKEKGGLEGLIHSQRRQDILDLWIYH          (SEQ ID NO: 81)
86-116   DLSHFLKEKGGLEGLIHSQRRQDILDLWIYH           (SEQ ID NO: 82)
87-116   LSHFLKEKGGLEGLIHSQRRQDILDLWIYH            (SEQ ID NO: 83)
88-116   SHFLKEKGGLEGLIHSQRRQDILDLWIYH             (SEQ ID NO: 84)
89-116   HFLKEKGGLEGLIHSQRRQDILDLWIYH              (SEQ ID NO: 85)
90-116   FLKEKGGLEGLIHSQRRQDILDLWIYH               (SEQ ID NO: 86)
80-115   TYKAAVDLSHFLKEKGGLEGLIHSQRRQDILDLWIY      (SEQ ID NO:87)
81-115   YKAAVDLSHFLKEKGGLEGLIHSQRRQDILDLWIY       (SEQ ID NO: 88)
82-115   KAAVDLSHFLKEKGGLEGLIHSQRRQDILDLWIY        (SEQ ID NO: 89)
83-115   AAVDLSHFLKEKGGLEGLIHSQRRQDILDLWIY         (SEQ ID NO: 90)
84-115   AVDLSHFLKEKGGLEGLIHSQRRQDILDLWIY          (SEQ ID NO: 91)
85-115   VDLSHFLKEKGGLEGLIHSQRRQDILDLWIY           (SEQ ID NO: 92)
86-115   DLSHFLKEKGGLEGLIHSQRRQDILDLWIY            (SEQ ID NO: 93)
87-115   LSHFLKEKGGLEGLIHSQRRQDILDLWIY             (SEQ ID NO: 94)
```

-continued

| | | |
|---|---|---|
| 88-115 | SHFLKEKGGLEGLIHSQRRQDILDLWIY | (SEQ ID NO: 95) |
| 89-115 | HFLKEKGGLEGLIHSQRRQDILDLWIY | (SEQ ID NO: 96) |
| 90-115 | FLKEKGGLEGLIHSQRRQDILDLWIY | (SEQ ID NO: 97) |
| 80-114 | TYKAAVDLSHFLKEKGGLEGLIHSQRRQDILDLWI | (SEQ ID NO: 98) |
| 81-114 | YKAAVDLSHFLKEKGGLEGLIHSQRRQDILDLWI | (SEQ ID NO:99) |
| 82-114 | KAAVDLSHFLKEKGGLEGLIHSQRRQDILDLWI | (SEQ ID NO: 100) |
| 83-114 | AAVDLSHFLKEKGGLEGLIHSQRRQDILDLWI | (SEQ ID NO: 101) |
| 84-114 | AVDLSHFLKEKGGLEGLIHSQRRQDILDLWI | (SEQ ID NO: 102) |
| 85-114 | VDLSHFLKEKGGLEGLIHSQRRQDILDLWI | (SEQ ID NO: 103) |
| 86-114 | DLSHFLKEKGGLEGLIHSQRRQDILDLWI | (SEQ ID NO: 104) |
| 87-114 | LSHFLKEKGGLEGLIHSQRRQDILDLWI | (SEQ ID NO: 105) |
| 88-114 | SHFLKEKGGLEGLIHSQRRQDILDLWI | (SEQ ID NO: 106) |
| 89-114 | HFLKEKGGLEGLIHSQRRQDILDLWI | (SEQ ID NO: 107) |
| 90-114 | FLKEKGGLEGLIHSQRRQDILDLWI | (SEQ ID NO: 108) |
| 80-113 | TYKAAVDLSKFLKEKGGLEGLIHSQRRQDILDLW | (SEQ ID NO: 109) |
| 81-113 | YKAAVDLSHFLKEKGGLEGLIHSQRRQDLLDLW | (SEQ ID NO: 110) |
| 82-113 | KAAVDLSHFLKEKGGLEGLIHSQRRQDILDLW | (SEQ ID NO: 111) |
| 83-113 | AAVDLSHFLKEKGGLEGLIHSQRRQDILDLW | (SEQ ID NO: 112) |
| 84-113 | AVDLSHFLKEKGGLEGLIHSQRRQDILDLW | (SEQ ID NO: 113) |
| 85-113 | VDLSHFLKEKGGLEGLIHSQRRQDILDLW | (SEQ ID NO: 114) |
| 86-113 | DLSHFLKEKGGLEGLIHSQRRQDILDLW | (SEQ ID NO: 115) |
| 87-113 | LSHFLKEKGGLEGLIHSQRRQDILDLW | (SEQ ID NO: 116) |
| 88-113 | SHFLKEKGGLEGLIHSQRRQDILDLW | (SEQ ID NO: 117) |
| 89-113 | HFLKEKGGLEGLIHSQRRQDILDLW | (SEQ ID NO: 118) |
| 90-113 | FLKEKGGLEGLIHSQRRQDILDLW | (SEQ ID NO: 119) |
| 80-112 | TYKAAVDLSHFLKEKGGLEGLIHSQRRQDILDL | (SEQ ID NO: 120) |
| 81-112 | YKAAVDLSHFLKEKGGLEGLIHSQRRQDILDL | (SEQ ID NO: 121) |
| 82-112 | KAAVDLSHFLKEKGGLEGLIHSQRRQDILDL | (SEQ ID NO: 122) |
| 83-112 | AAVDLSHFLKEKGGLEGLIHSQRRQDILDL | (SEQ ID NO: 123) |
| 84-112 | AVDLSHFLKEKGGLEGLIHSQRRQDILDL | (SEQ ID NO: 124) |
| 85-112 | VDLSHFLKEKGGLEGLIHSQRRQDILDL | (SEQ ID NO: 125) |
| 86-112 | DLSIWLKEKGGLEGLIHSQRRQDILDL | (SEQ ID NO: 126) |
| 87-112 | LSHFLKEKGGLEGLIHSQRRQDILDL | (SEQ ID NO: 127) |
| 88-112 | SHFLKEKGGLEGLIHSQRRQDILDL | (SEQ ID NO: 128) |
| 89-112 | HFLKEKGGLEGLIHSQRRQDILDL | (SEQ ID NO: 129) |
| 90-112 | FLKEKGGLEGLIHSQRRQDILDL | (SEQ ID NO: 130) | or of homologous peptide sequences presenting at least 80% sequence identity, preferably 90% identity, with said HIV-1 Nef fragments.

The present invention also relates to new proteins or polypeptides comprising said HIV-1 Nef fragments or homologous peptide sequences, provided that if present, the sequences adjacent to the respective N-terminal end and/or C-terminal end of the HIV-1 Nef fragments in said protein or polypeptide are different from the sequences adjacent to the respective N-terminal end and/or C-terminal end of the HIV-1 Nef fragments in the Nef proteins from which they derive.

In another preferred embodiment, the new protein or polypeptide is constituted of one of the following HIV-2 Nef fragments:

```
104-150  RVPLREMTYRLARDMSHLIKEKGGLEGLYYSDRRRRVLDIYLEKEEG  (SEQ ID NO: 131)

105-150  VPLREMTYRLARDMSHLIKEKGGLEGLYYSDRRRRVLDIYLEKEEG   (SEQ ID NO: 132)

106-150  PLREMTYRLARDMSHLIKEKGGLEGLYYSDRRRRVLDIYLEKEEG    (SEQ ID NO: 133)

107-150  LREMTYRLARDMSHLIKEKGGLEGLYYSDRRRRVLDIYLEKEEG     (SEQ ID NO: 134)

108-150  REMTYRLARDMSHLIKEKGGLEGLYYSDRRRRVLDIYLEKEEG      (SEQ ID NO: 135)

109-150  EMTYRLARDMSHLIKEKGGLEGLYYSDRRRRVLDIYLEKEEG       (SEQ ID NO: 136)

110-150  MTYRLARDMSHLIKEKGGLEGLYYSDRRRRVLDIYLEKEEG        (SEQ ID NO: 137)

111-150  TYRLARDMSHLIKEKGGLEGLYYSDRRRRVLDIYLEKEEG         (SEQ ID NO: 138)

112-150  YRLARDMSHLIKEKGGLEGLYYSDRRRRVLDIYLEKEEG          (SEQ ID NO: 139)

113-150  RLARDMSHLIKEKGGLEGLYYSDRRRRVLDIYLEKEEG           (SEQ ID NO: 140)

114-150  LARDMSHLIKEKGGLEGLYYSDRRRRVLDIYLEKEEG            (SEQ ID NO: 141)

115-150  ARDMSHLIKEKGGLEGLYYSDRRRRVLDIYLEKEEG             (SEQ ID NO: 142)

116-150  RDMSHLIKEKGGLEGLYYSDRRRRVLDIYLEKEEG              (SEQ ID NO: 143)

117-150  DMSHLIKEKGGLEGLYYSDRRRRVLDIYLEKEEG               (SEQ ID NO: 144)

118-150  MSHLIKEKGGLEGLYYSDRRRRVLDIYLEKEEG                (SEQ ID NO: 145)

119-150  SHLIKEKGGLEGLYYSDRRRRVLDIYLEKEEG                 (SEQ ID NO: 146)

120-150  HLIKEKGGLEGLYYSDRRRRVLDIYLEKEEG                  (SEQ ID NO: 147)

121-150  LIKEKGGLEGLYYSDRRRRVLDIYLEKEEG                   (SEQ ID NO: 148)

104-149  RVPLREMTYRLARDMSHLIKEKGGLEGLYYSDRRRRVLDIYLEKEE   (SEQ ID NO: 149)

105-149  VPLREMTYRLARDMSHLIKEKGGLEGLYYSDRRRRVLDIYLEKEE    (SEQ ID NO: 150)

106-149  PLREMTYRLARDMSHLIKEKGGLEGLYYSDRRRRVLDIYLEKEE     (SEQ ID NO: 151)

107-149  LREMTYRLARDMSHLIKEKGGLEGLYYSDRRRRVLDIYLEKEE      (SEQ ID NO: 152)

108-149  REMTYRLARDMSHLIKEKGGLEGLYYSDRRRRVLDIYLEKEE       (SEQ ID NO: 153)

109-149  EMTYRLARDMSHLIKEKGGLEGLYYSDRRRRVLDIYLEKEE        (SEQ ID NO: 154)

110-149  MTYRLARDMSHLIKEKGGLEGLYYSDRRRRVLDIYLEKEE         (SEQ ID NO: 155)

111-149  TYRLARDMSHLIKEKGGLEGLYYSDRRRRVLDIYLEKEE          (SEQ ID NO: 156)

112-149  YRLARDMSHLIKEKGGLEGLYYSDRRRRVLDIYLEKEE           (SEQ ID NO: 157)

113-149  RLARDMSHLIKEKGGLEGLYYSDRRRRVLDIYLEKEE            (SEQ ID NO: 158)

114-149  LARDMSHLIKEKGGLEGLYYSDRRRRVLDIYLEKEE             (SEQ ID NO: 159)

115-149  ARDMSHLIKEKGGLEGLYYSDRRRRVLDIYLEKEE              (SEQ ID NO: 160)

116-149  RDMSHLIKEKGGLEGLYYSDRRRRVLDIYLEKEE               (SEQ ID NO: 161)

117-149  DMSHLIKEKGGLEGLYYSDRRRRVLDIYLEKEE                (SEQ ID NO: 162)

118-149  MSHLIKEKGGLEGLYYSDRRRRVLDIYLEKEE                 (SEQ ID NO: 163)

119-149  SHLIKEKGGLEGLYYSDRRRRVLDIYLEKEE                  (SEQ ID NO: 164)

120-149  HLIKEKGGLEGLYYSDRRRRVLDIYLEKEE                   (SEQ ID NO: 165)

121-149  LIKEKGGLEGLYYSDRRRRVLDIYLEKEE                    (SEQ ID NO: 166)

104-148  RVPLREMTYRLARDMSHLIKEKGGLEGLYYSDRRRRVLDIYLEKE    (SEQ ID NO: 167)

105-148  VPLREMTYRLARDMSHLIKEKGGLEGLYYSDRRRRVLDIYLEKE     (SEQ ID NO: 168)

106-148  PLREMTYRLARDMSHLIKEKGGLEGLYYSDRRRRVLDIYLEKE      (SEQ ID NO: 169)

107-148  LREMTYRLARDMSHLIKEKGGLEGLYYSDRRRRVLDIYLEKE       (SEQ ID NO: 170)

108-148  REMTYRLARDMSHLIKEKGGLEGLYYSDRRRRVLDIYLEKE        (SEQ ID NO: 171)
```

```
109-148  EMTYRLARDMSHLIKEKGGLEGLYYSDRRRRVLDIYLEKE        (SEQ ID NO: 172)

110-148  MTYRLARDMSHLIKEKGGLEGLYYSDRRRRVLDIYLEKE         (SEQ ID NO: 173)

111-148  TYRLARDMSHLIKEKGGLEGLYYSDRRRRVLDIYLEKE          (SEQ ID NO: 174)

112-148  YRLARDMSHLIKEKGGLEGLYYSDRRRRVLDIYLEKE           (SEQ ID NO: 175)

113-148  RLARDMSHLIKEKGGLEGLYYSDRRRRVLDIYLEKE            (SEQ ID NO: 176)

114-148  LARDMSHLIKEKGGLEGLYYSDRRRRVLDIYLEKE             (SEQ ID NO: 177)

115-148  ARDMSHLIKEKGGLEGLYYSDRRRRVLDIYLEKE              (SEQ ID NO: 178)

116-148  RDMSHLIKEKGGLEGLYYSDRRRRVLDIYLEKE               (SEQ ID NO: 179)

117-148  DMSHLIKEKGGLEGLYYSDRRRRVLDIYLEKE                (SEQ ID NO: 180)

118-148  MSHLIKEKGGLEGLYYSDRRRRVLDIYLEKE                 (SEQ ID NO: 181)

119-148  SHLIKEKGGLBGLYYSDRRRRVLDIYLEKE                  (SEQ ID NO: 182)

120-148  HLIKEKGGLEGLYYSDRRRRVLDIYLEKE                   (SEQ ID NO: 183)

121-148  LIKEKGGLEGLYYSDRRRRVLDIYLEKE                    (SEQ ID NO: 184)

104-147  RVPLREMTYRLARDMSHLIKEKGGLEGLYYSDRRRRVLDIYLEK    (SEQ ID NO: 185)

105-147  VPLREMTYRLARDMSHLIKEKGGLEGLYYSDRRRRVLDIYLEK     (SEQ ID NO: 186)

106-147  PLREMTYRLARDMSHLIKEKGGLEGLYYSDRRRRVLDIYLEK      (SEQ ID NO: 187)

107-147  LREMTYRLARDMSHLIKEKGGLEGLYYSDRRRRVLDIYLEK       (SEQ ID NO: 188)

108-147  REMTYRLARDMSHLIKEKGGLEGLYYSDRRRRVLDIYLEK        (SEQ ID NO: 189)

109-147  EMTYRLARDMSHLIKEKGGLEGLYYSDRRRRVLDIYLEK         (SEQ ID NO: 190)

110-147  MTYRLARDMSHLIKEKGGLEGLYYSDRRRRVLDIYLEK          (SEQ ID NO: 191)

111-147  TYRLARDMSHLIKEKGGLEGLYYSDRRRRVLDIYLEK           (SEQ ID NO: 192)

112-147  YRLARDMSHLIKEKGGLEGLYYSDRRRRVLDIYLEK            (SEQ ID NO: 193)

113-147  RLARDMSHLIKEKGGLEGLYYSDRRRRVLDIYLEK             (SEQ ID NO: 194)

114-147  LARDMSHLIKEKGGLEGLYYSDRRRRVLDIYLEK              (SEQ ID NO: 195)

115-147  ARDMSHLIKEKGGLEGLYYSDRRRRVLDIYLEK               (SEQ ID NO: 196)

116-147  RDMSHLIKEKGGLEGLYYSDRRRRVLDIYLEK                (SEQ ID NO: 197)

117-147  DMSHLIKEKGGLEGLYYSDRRRRVLDIYLEK                 (SEQ ID NO: 198)

118-147  MSHLIKEKGGLEGLYYSDRRRRVLDIYLEK                  (SEQ ID NO: 199)

119-147  SHLIKEKGGLEGLYYSDRRRRVLDIYLEK                   (SEQ ID NO: 200)

120-147  HLIKEKGGLEGLYYSDRRRRVLDIYLEK                    (SEQ ID NO: 201)

121-147  LIKEKGGLEGLYYSDRRRRVLDIYLEK                     (SEQ ID NO: 202)

104-146  RVPLREMTYRLARDMSHLIKEKGGLEGLYYSDRRRRVLDIYLE     (SEQ ID NO: 203)

105-146  VPLREMTYRLARDMSHLIKEKGGLEGLYYSDRRRRVLDIYLE      (SEQ ID NO: 204)

106-146  PLREMTYRLARDMSHLIKEKGGLEGLYYSDRRRRVLDIYLE       (SEQ ID NO: 205)

107-146  LREMTYRLARDMSHLIKEKGGLEGLYYSDRRRRVLDIYLE        (SEQ ID NO: 206)

108-146  REMTYRLARDMSHLIKEKGGLEGLYYSDRRERVLDIYLE         (SEQ ID NO: 207)

109-146  EMTYRLARDMSHLIKEKGGLEGLYYSDRRRRVLDIYLE          (SEQ ID NO: 208)

110-146  MTYRLARDMSHLIKEKGGLEGLYYSDRRRRVLDIYLE           (SEQ ID NO: 209)

111-146  TYRLARDMSHLIKEKGGLEGLYYSDRRRRVLDIYLE            (SEQ ID NO: 210)

112-146  YRLARDMSHLIKEKGGLEGLYYSDRRRRVLDIYLE             (SEQ ID NO: 211)
```

-continued

| | | |
|---|---|---|
| 113-146 | RLARDMSHLIKEKGGLEGLYYSDRRRRVLDIYLE | (SEQ ID NO: 212) |
| 114-146 | LARDMSHLIKEKGGLEGLYYSDRRRRVLDIYLE | (SEQ ID NO: 213) |
| 115-146 | ARDMSHLIKEKGGLEGLYYSDRRRRVLDIYLE | (SEQ ID NO: 214) |
| 116-146 | RDMSHLIKEKGGLEGLYYSDRRRRVLDIYLE | (SEQ ID NO: 215) |
| 117-146 | DMSHLIKEKGGLEGLYYSDRRRRVLDIYLE | (SEQ ID NO: 216) |
| 118-146 | MSHLIKEKGGLEGLYYSDRRRRVLDIYLE | (SEQ ID NO: 217) |
| 119-146 | SHLIKEKGGLEGLYYSDRRRRVLDIYLE | (SEQ ID NO: 218) |
| 120-146 | HLIKEKGGLEGLYYSDRRRRVLDIYLE | (SEQ ID NO: 219) |
| 121-146 | LIKEKGGLEGLYYSDRRRRVLDIYLE | (SEQ ID NO: 220) |
| 104-145 | RVPLREMTYRLARDMSHLIKEKGGLEGLYYSDRRRRVLDIYL | (SEQ ID NO: 221) |
| 105-145 | VPLREMTYRLARDMSHLIKEKGGLEGLYYSDRRRRVLDIYL | (SEQ ID NO: 222) |
| 106-145 | PLREMTYRLARDMSHLIKEKGGLEGLYYSDRRRRVLDIYL | (SEQ ID NO: 223) |
| 107-145 | LREMTYRLARDMSHLIKEKGGLEGLYYSDRRRRVLDIYL | (SEQ ID NO: 224) |
| 108-145 | REMTYRLARDMSHLIKEKGGLEGLYYSDRRRRVLDIYL | (SEQ ID NO: 225) |
| 109-145 | EMTYRLARDMSHLIKEKGGLEGLYYSDRRRRVLDIYL | (SEQ ID NO: 226) |
| 110-145 | MTYRLARDMSHLIKEKGGLEGLYYSDRRRRVLDIYL | (SEQ ID NO: 227) |
| 111-145 | TYRLARDMSHLIKEKGGLEGLYYSDRRRRVLDIYL | (SEQ ID NO: 228) |
| 112-145 | YRLARDMSHLIKEKGGLEGLYYSDRRRRVLDIYL | (SEQ ID NO: 229) |
| 113-145 | RLARDMSHLIKEKGGLEGLYYSDRRRRVLDIYL | (SEQ ID NO: 230) |
| 114-145 | LARDMSHLIKEKGGLEGLYYSDRRRRVLDIYL | (SEQ ID NO: 231) |
| 115-145 | ARDMSHLIKEKGGLEGLYYSDRRRRVLDIYL | (SEQ ID NO: 232) |
| 116-145 | RDMSHLIKEKGGLEGLYYSDRRRRVLDIYL | (SEQ ID NO: 233) |
| 117-145 | DMSHLIKEKGGLEGLYYSDRRRRVLDIYL | (SEQ ID NO: 234) |
| 118-145 | MSHLIKEKGGLEGLYYSDRRRRVLDIYL | (SEQ ID NO: 235) |
| 119-145 | SHLIKEKGGLEGLYYSDRRRRVLDIYL | (SEQ ID NO: 236) |
| 120-145 | HLIKEKGGLEGLYYSDRRRRVLDIYL | (SEQ ID NO: 237) |
| 121-145 | LIKEKGGLEGLYYSDRRRRVLDIYL | (SEQ ID NO: 238) |
| 104-144 | RVPLREMTYRLARDMSHLIKEKGGLEGLYYSDRRRRVLDIY | (SEQ ID NO: 239) |
| 105-144 | VPLREMTYRLARDMSHLIKEKGGLEGLYYSDRRRRVLDIY | (SEQ ID NO: 240) |
| 106-144 | PLREMTYRLARDMSHLIKEKGGLEGLYYSDRRRRVLDIY | (SEQ ID NO: 241) |
| 107-144 | LREMTYRLARDMSHLIKEKGGLEGLYYSDRRRRVLDIY | (SEQ ID NO: 242) |
| 108-144 | REMTYRLARDMSHLIKEKGGLEGLYYSDRRRRVLDIY | (SEQ ID NO: 243) |
| 109-144 | EMTYRLARDMSHLIKEKGGLEGLYYSDRRRRVLDIY | (SEQ ID NO: 244) |
| 110-144 | MTYRLARDMSHLIKEKGGLEGLYYSDRRRRVLDIY | (SEQ ID NO: 245) |
| 111-144 | TYRLARDMSHLIKEKGGLEGLYYSDRRRRVLDIY | (SEQ ID NO: 246) |
| 112-144 | YRLARDMSHLIKEKGGLEGLYYSDRRRRVLDIY | (SEQ ID NO: 247) |
| 113-144 | RLARDMSHLIKEKGGLEGLYYSDRRRRVLDIY | (SEQ ID NO: 248) |
| 114-144 | LARDMSHLIKEKGGLEGLYYSDRRRRVLDIY | (SEQ ID NO: 249) |
| 115-144 | ARDMSHLIKEKGGLEGLYYSDRRRRVLDIY | (SEQ ID NO: 250) |
| 116-144 | RDMSHLIKEKGGLEGLYYSDRRRRVLDIY | (SEQ ID NO: 251) |
| 117-144 | DMSHLIKEKGGLEGLYYSDRRRRVLDIY | (SEQ ID NO: 252) |

-continued

| | | |
|---|---|---|
| 118-144 | MSHLIKEKGGLEGLYYSDRRRRVLDIY | (SEQ ID NO: 253) |
| 119-144 | SHLIKEKGGLEGLYYSDRRRRVLDIY | (SEQ ID NO: 254) |
| 120-144 | HLIKEKGGLEGLYYSDRRRRVLDIY | (SEQ ID NO: 255) |
| 121-144 | LIKEKGGLEGLYYSDRRRRVLDIY | (SEQ ID NO: 256) |
| 104-143 | RVPLREMTYRLARDMSHLIKEKGGLEGLYYSDRRRRVLDI | (SEQ ID NO: 257) |
| 105-143 | VPLREMTYRLARDMSHLIKEKGGLEGLYYSDRRRRVLDI | (SEQ ID NO: 258) |
| 106-143 | PLREMTYRLARDMSHLIKEKGGLEGLYYSDRRRRVLDI | (SEQ ID NO: 259) |
| 107-143 | LREMTYRLARDMSHLIKEKGGLEGLYYSDRRRRVLDI | (SEQ ID NO: 260) |
| 108-143 | REMTYRLARDMSHLIKEKGGLEGLYYSDRRRRVLDI | (SEQ ID NO: 261) |
| 109-143 | EMTYRLARDMSHLIKEKGGLEGLYYSDRRRRVLDI | (SEQ ID NO: 262) |
| 110-143 | MTYRLARDMSHLIKEKGGLEGLYYSDRRRRVLDI | (SEQ ID NO: 263) |
| 111-143 | TYRLARDMSHLIKEKGGLEGLYYSDRRRRVLDI | (SEQ ID NO: 264) |
| 112-143 | YRLARDMSHLIKEKGGLEGLYYSDRRRRVLDI | (SEQ ID NO: 265) |
| 113-143 | RLARDMSHLIKEKGGLEGLYYSDRRRRVLDI | (SEQ ID NO: 266) |
| 114-143 | LARDMSHLIKEKGGLEGLYYSDRRRRVLDI | (SEQ ID NO: 267) |
| 115-143 | ARDMSHLIKEKGGLEGLYYSDRRRRVLDI | (SEQ ID NO: 268) |
| 116-143 | RDMSHLIKEKGGLEGLYYSDRRRRVLDI | (SEQ ID NO: 269) |
| 117-143 | DMSHLIKEKGGLEGLYYSDRRRRVLDI | (SEQ ID NO: 270) |
| 118-143 | MSHLIKEKGGLEGLYYSDRRRRVLDI | (SEQ ID NO: 271) |
| 119-143 | SHLIKEKGGLEGLYYSDRRRRVLDI | (SEQ ID NO: 272) |
| 120-143 | HLIKEKGGLEGLYYSDRRRRVLDI | (SEQ ID NO: 273) |
| 121-143 | LIKEKGGLEGLYYSDRRRRVLDI | (SEQ ID NO: 274) | or of homologous peptide sequences presenting at least 80% sequence identity, preferably 90% identity, with said HIV-2 Nef fragments.

The present invention also relates to new proteins or polypeptides comprising said HIV-2 Nef fragments or homologous peptide sequences, provided that if present, the sequences adjacent to the respective N-terminal end and/or C-terminal end of the HIV-2 Nef fragments in said protein or polypeptide are different from the sequences adjacent to the respective N-terminal end and/or C-terminal end of the HIV-2 Nef fragments in the Nef proteins from which they derive.

In another particularly preferred embodiment of the above defined new protein or polypeptide, the immunosuppressive domain is mutated by deletion, substitution and/or insertion of at least one amino acid, and in particular the amino acid homologous to the amino acid at position 93 of SEQ ID NO: 1 is replaced by any amino acid different from E, in particular by W, F, M, Y, R, H or K, more particularly by R, H, or K, and preferably by R. Advantageously, such a new protein or polypeptide is devoid of immunosuppressive activity.

In yet another particularly preferred embodiment of the above defined new protein or polypeptide, the immunosuppressive domain of a HIV-1 Nef protein is mutated by the substitution of the anino acid at position 93 of the sequence of said HIV-1 Nef protein by any amino acid different from E, in particular by W, F, M, Y, R, H or K, more particularly by R, H, or K, and preferably by R.

The present invention also relates to a nucleic acid, characterized in that it codes for a new protein or polypeptide as defined above.

The present invention also relates to peptidomimetics of the new proteins or polypeptides as defined above.

The present invention also relates to antibodies or fragments thereof, scFv polypeptides, aptamers, or binding peptides, directed against a sequence ranging from the amino acid at position 80 to the amino acid at position 150 of a Nef protein, and in particular:

- against a sequence ranging from the amino acid at position 80 to the amino acid at position 120, more particularly from the amino acid at position 90 to the amino acid at position 120, of the sequence of a HIV-1 Nef protein
- against a sequence ranging from the amino acid at position 104 to the amino acid at position 150 of the sequence of a HIV-2 Nef protein.

The present invention also relates to antibodies or fragments thereof, scFv polypeptides, aptamers, or binding peptides, directed against the new proteins or polypeptides as defined above, provided that said antibodies or fragments thereof, scFv polypeptides, or aptamers do not bind to Nef proteins wherein the immunosuppressive domains corresponds to that of said new proteins or polypeptides as defined above.

As intended herein the above defined antibodies or fragments thereof, scFv polypeptides, aptamers, or binding peptides, are specific for the new proteins or polypeptides according to the invention (i.e. proteins or polypeptides comprising the immunosuppressive domain of the Nef protein according to the invention). In particular, these antibodies or fragments thereof, scFv polypeptides, or aptamers do not bind to the immunosuppressive domain of the Nef protein in its natural setting, that is, these antibodies or fragments thereof, scFv polypeptides, or aptamers do not bind to natural Nef proteins.

The present invention also relates to a pharmaceutical or vaccine composition, comprising as active substance an above defined new protein or polypeptide, or an above defined nucleic acid encoding said new protein or polypeptide, in association with a pharmaceutically acceptable carrier.

The present invention also relates to the use of a protein or a polypeptide comprising or being constituted of a Nef protein or fragments thereof, wherein said protein or polypeptide presents an immunosuppressive activity, for the manufacture of a medicament intended for the prevention or the treatment of pathologies requiring an inhibition of the immune system, such as allergies, autoimmune diseases or graft rejections.

In an advantageous embodiment, the invention relates to the above mentioned use of a new protein or polypeptide as defined above, wherein said new protein or polypeptide presents an immunosuppressive property, for the manufacture of a medicament intended for the prevention or the treatment of pathologies requiring an inhibition of the immune system, such as allergies, autoimmune diseases or graft rejections.

The present invention also relates to the use of a protein or a polypeptide comprising or being constituted of a Nef protein or fragments thereof, for screening compounds liable to inhibit the immunosuppressive activity of Nef proteins.

The present invention also relates to the use of a new protein or polypeptide as defined above, for screening compounds liable to inhibit the immunosuppressive activity of Nef proteins.

Advantageously, such compounds which are liable to inhibit the immunosuppressive activity of Nef proteins, can be used as anti-viral agents.

As intended herein the compounds to screen can be of any chemical nature. In particular, the compounds to screen are included in chemical compound libraries.

In a preferred embodiment of the above defined use of a new protein or polypeptide as defined above, the sequence of the immunosuppressive domain of the Nef protein corresponds to a non-mutated sequence.

The present invention also relates to compounds liable to inhibit the immunosuppressive activity of Nef proteins. Such compounds may be useful for the manufacture of pharmaceutical compositions, in particular intended for the prevention or the treatment of viral diseases, such as HIV or SIV infections.

The immunosuppressive-inhibitory activity of these compounds can be determined by measuring the immunosuppression index of a given Nef protein in the absence or in the presence of the compounds. A compound will be said to possess an immunosuppressive-inhibitory activity when the immunosuppression index of a given Nef protein in the presence of said compound is decreased with respect to the the immunosuppression index of the same Nef protein in the absence of said compound.

The present invention also relates to the use of ligands of the immunosuppressive domain of Nef proteins, such as antibodies or fragments thereof, scFv polypeptides, aptamers, or binding peptides, to screen for compounds liable to inhibit the immunosuppressive activity of Nef proteins.

The present invention also relates to a method to screen for compounds liable to inhibit the immunosuppressive activity of Nef proteins, comprising the following steps:

contacting a Nef protein, or a fragment thereof comprising the immunosuppressive domain of a Nef protein, or a new protein or polypeptide as defined above, with compounds to screen, selecting the compounds which bind to the immunosuppressive domain of the Nef protein, or of the fragment thereof comprising the immunosuppressive domain of said Nef protein, or of the new protein or polypeptide as defined above, optionally checking that the selected compounds inhibit the immunosuppressive activity of Nef proteins.

In a preferred embodiment of the invention, the above mentioned screening method comprises the following steps:

contacting a Nef protein, or a fragment thereof comprising the immunosuppressive domain of a Nef protein, or a new protein or polypeptide as defined above, with a compounds to screen and with a ligand of the immunosuppressive domain, such as an antibody, a scFv polypeptide, an aptamer, or a binding peptide, selecting the compounds which prevent the binding of the ligand to the Nef protein, or to the Nef fragment, or to a new protein or polypeptide as defined above and which do not bind to said ligand, optionally checking that the selected compounds inhibit the immunosuppressive activity of Nef proteins.

The present invention also relates to a screening method for compounds liable to inhibit the immunosuppressive activity of Nef proteins, wherein compounds which bind to a Nef protein or a fragment thereof are selected and it is checked that said selected compounds inhibit the immunosuppressive activity of said Nef protein.

The present invention also relates to the compounds which are selected according to the above defined screening method of the invention.

DESCRIPTION OF THE FIGURES

FIG. 1

FIG. 1 represents the immunosuppression index (vertical axis) of wild type Nef (white column) and of its E93R mutant (grey column).

FIG. 2

FIG. 2 represents the downregulation of CD4 expression (vertical axis, arbitrary units) by HeLa cells transformed with the indicated amount (horizontal axis, in μg) of wild type Nef expressing vectors (black circles, plain lines) or E93R Nef mutant expressing vectors (white circles, dotted lines).

FIG. 3

FIG. 3 represents the downregulation of MHC-I expression (vertical axis, arbitrary units, left for Nef, right for the E93R Nef mutant) by 293T cells transformed with the indicated amount (horizontal axis, in μg) of wild type Nef expressing vectors (black circles, plain lines) or E93R Nef mutant expressing vectors (white circles, dotted lines).

FIG. 4

FIG. 4 represents a sequence alignment generated by the Clustal W software of Nef amino acid sequences from independent HIV-1, HIV-2 and SIV isolates. The part of the sequences of the Nef proteins comprising the immunosuppressive domain is boxed. The amino acids corresponding or homologous to E93 of SEQ ID NO: 1 (NEF_HIVB1) are in bold. The stars represent positions for which amino acids are conserved; single points, positions for which amino acids are substantially conserved; and double points, positions for which amino acids possess similar physicochemical properties. (SEQ ID NOS 275-293 are disclosed respectively.)

FIG. 5

FIG. 5 represents the immunosuppression index of HIV-1 strain LAI Nef and of three of its fragments (1-89, 80-120 and 113-206). The partial sequence of HIV-1 strain LAI is presented on top of the figure with the position of several amino acids as well as the positions of the fragments. The presence (+) or absence (−) of an immunosuppressive activity for wild type Nef and for each fragment is indicated on the right (immunosuppression index). SEQ ID NO 294 is shown as fragment 76-124).

FIG. 6A and FIG. 6B

EXAMPLES

Example 1

Figure 1:
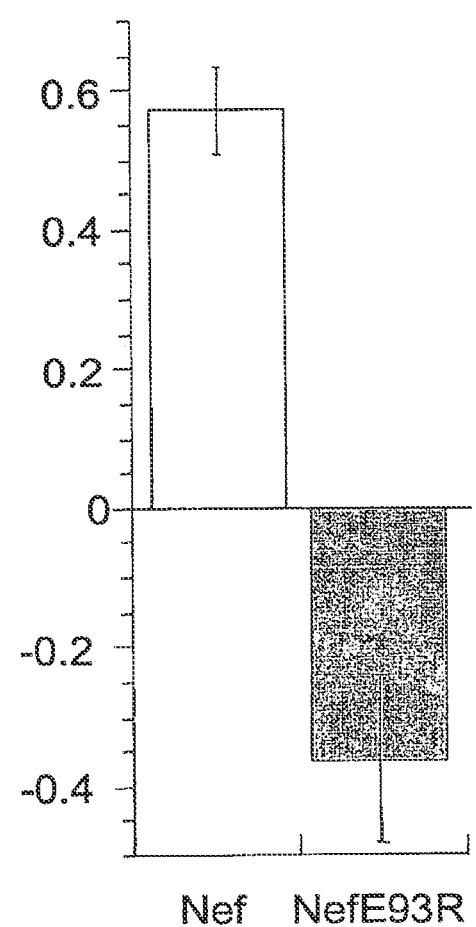

Cloning of the Genes Encoding Wild Type Nef and the E93R Nef Mutant

HIV-1 strain LAI Nef was retrieved from pCDNA3-Nef (Peden K., Emerman M. and Montagnier L. 1991, *Virology* 185(2):661-672) (gift from O. Schwartz, Institut Pasteur, France) by PCR with high-fidelity Pfx Platinum polymerase (Invitrogen) and the following primers:

(SEQ ID NO: 4)
5'-ATACATGGCCCAGCCGGCCGGTGGCAAGTGGTCAAAAAGTAGT-3'
and (SEQ ID NO: 5)
5'-ATACATGGATCCACGCGTTCAGCAGTTCTTGAAGTACTCCGG-3'.

The amplification product was digested with SfiI and BamHI and ligated in the pSecTag2A vector (Invitrogen) opened with the same enzymes. Nef preceded with the export signal sequence of the vector was then amplified with the following primers:

(SEQ ID NO: 6)
5'-ATACATACCGGTATGGAGACAGACACACTCCTGCTATG-3',
and (SEQ ID NO: 7)
5'-ATACATGGATCCACGCGTTCAGCAGTTCTTGAAGTACTCCGG-3'.

The product was digested with AgeI and MluI and ligated into the retroviral vector pDFG-MoTMtag (Mangeney & Heidmann (1998) *Proc. Natl. Acad. Sci. U.S.A.* 95:14920-5) digested with the same enzymes to obtain pDFG-expNef (SEQ ID NO: 16), expressing the exported version of HIV-Nef (SEQ ID NO: 17).

The mutation E93R was then introduced in pDFG-expNef by ligation of the three following fragments to yield pDFG-expNefE93R (SEQ ID NO: 18), expressing the exported version of E93R Nef (SEQ ID NO: 19):

1) the AgeI-MluI fragment of the vector;
2) a PCR product obtained with primers (SEQ ID NO: 8)
5'-ATACATACCGGTATGGAGACAGACACACTC-3'
and (SEQ ID NO: 9)
5'-ATACATCTTAAGAAAGTGGCTAAGATCTACAGCTGCC-3' and digested with AflII;
3) a PCR product obtained with primers (SEQ ID NO: 10)
5'-ATACATCTTAAGCGAAAGGGGGGACTGGAAGGG-3'
and (SEQ ID NO: 11)
5'-ATACATACGCGTTCAGCAGTTCTTGAA-3' digested with AflII and MluI.
Nef and its mutant E93R were then retrieved from the pDFG-expNef vectors with the following primers:

(SEQ ID NO: 12)
5'-ATACATGTCGACCCAACTAGAACCATGGGTGGCAAGTGGTCAAAAAG
TAG-3',
and (SEQ ID NO: 13)
5'-ATACATACGCGTTCAGCAGTTCTTGAA-3'.

The product was digested with SalI and MluI and ligated into phCMV-envT (Blaise et al. (2003) *Proc. Natl. Acad. Sci.* 100:13013-8) digested with XhoI and MluI, to yield respectively phCMV-Nef (SEQ ID NO: 20), expressing Nef (SEQ ID NO: 1), and phCMV-NefE93R (SEQ ID NO: 21), expressing E93R Nef (SEQ ID NO: 2).

Similarly, the sequences coding for Nef and the E93R Nef mutant with the export signal sequence were respectively extracted from pDFG-expNef and pDFG-expNefE93R and inserted into phCMV to yield phCMV-expNef (SEQ ID NO: 14) and phCMV-expNefE93R (SEQ ID NO: 15).

Example 2

Determination of the Immunosuppression Index of Wild Type Nef and of the E93R Nef Mutant The immunosuppression index of Nef and of its E93R mutant were measured following the general procedure described in Mangeney & Heidmann (1998) *Proc. Natl. Acad. Sci. U.S.A.* 95:14920-5 and Mangeney et al. (2001) *J. Gen. Virol.* 82:2515-8.

Briefly, MCA205 cells were stably transformed by plasmids pDFG-expNef and pDFG-expNefE93R, or optionally by plasmids phCMV-expNef and phCMV-expNefE93R, respectively. $10^6$ MCA cells expressing either wild type Nef, the E93R Nef mutant or no exogenous protein were then injected into Balb/c mice and tumor areas were measured every other day. After 7 to 8 days the immunosuppression index was determined.

The immunosuppression index of a protein was calculated as $(A_{protein} - A_{none})/A_{none}$, where $A_{protein}$ and $A_{none}$ are the peak tumor areas obtained with MCA cells expressing the proteins of interest (i.e. Nef or the E93R Nef mutant) and no exogenous protein, respectively.

The results are presented in FIG. 1. As can be seen, the immunosuppression index of Nef is approximately 0.6, which indicates that the size of the Nef expressing tumors is 1.6 times bigger than normal tumors, thus demonstrating that Nef is an immunosuppressive protein which inhibits the antitumor immune response. In contrast, the immunosuppressive index of the E93R Nef mutant is negative, thus demonstrating that this mutant has no immunosuppressive activity, and that tumors expressing this Nef mutant are more easily recognized and eliminated by the immune system than normal tumors.

Example 3

Down-Regulation of CD4 Expression by Nef and its E93R Mutant

Figure 2:
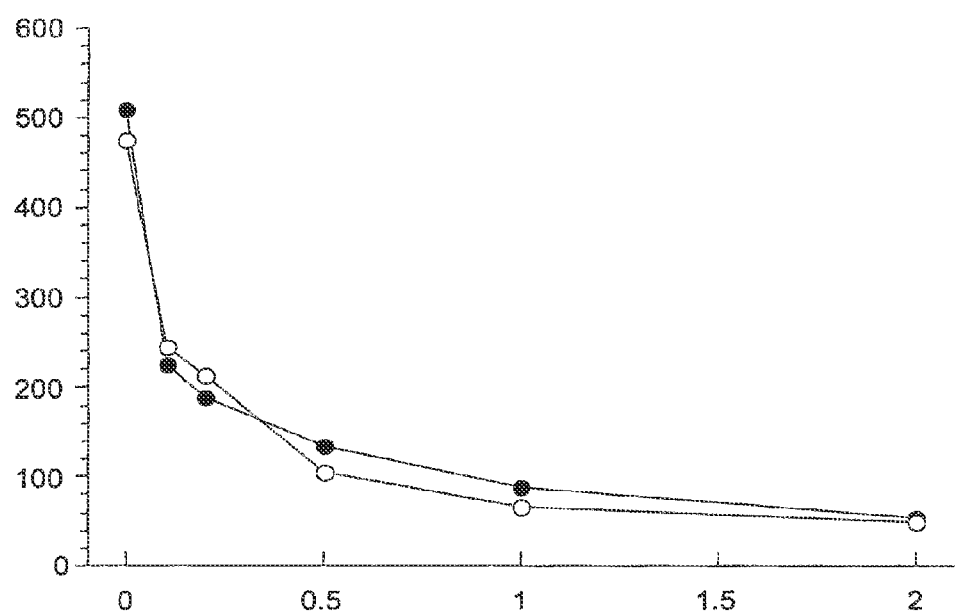

HeLa cells were cotransfected with 1 µg of CMV-CD4 (Janvier et al. (2001) *J. Virol.* 75:3971-6) and the indicated amount of phCMV-Nef or phCMV-NefE93R. CD4 expression was then measured by FACS using a PC5-coupled anti-human CD4 antibody (IM636, Immunotech). The results presented in FIG. 2 indicate that wild type Nef and the E93R Nef mutant downregulate CD4 expression to a similar extent. This implies that the structure of the E93R Nef mutant is unchanged with respect to that of wild type Nef.

Example 4

Down-Regulation of MHC-I Expression by Nef and its E93R Mutant 293T cells were cotransfected with 1 µg of CMV-HLA A2 (Le Gall et al. (2000) J. Virol. 74:9256-66) and the indicated amount of phCMV-Nef or phCMV-NefE93R. MHC-I expression was measured by FACS with PE-coupled anti human MHC-I antibody W6/32 (eBioscience).

Figure 3:
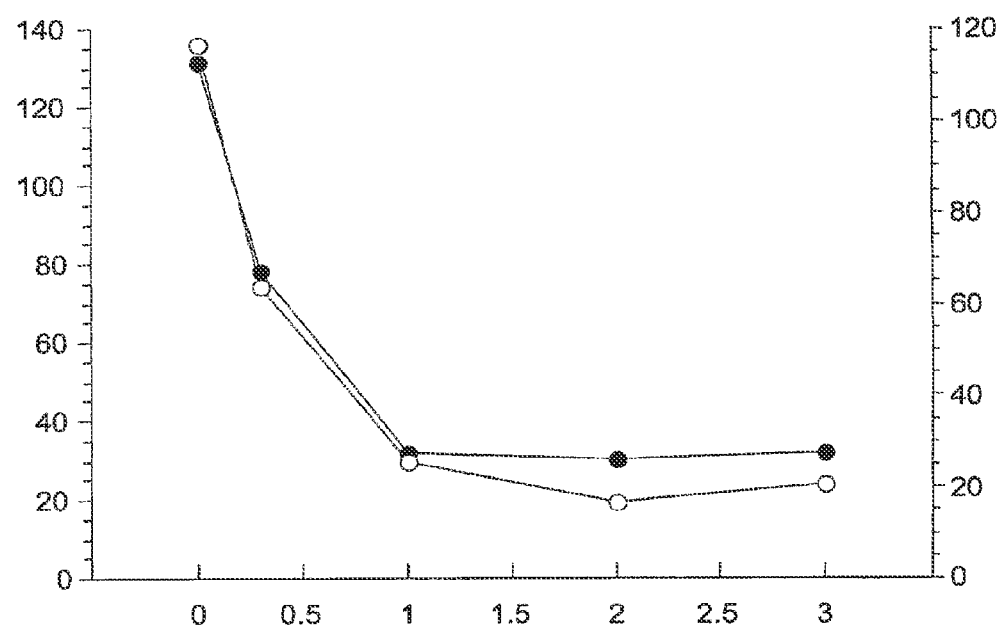

The results presented in FIG. 3 indicate that wild type Nef and the E93R Nef mutant downregulate MHC-I expression to a similar extent. This also implies that the structure of the E93R Nef mutant is unchanged with respect to that of wild type Nef.

Example 5

Determination of the Localization of the Immunosuppressive Domain of Wild Type Nef Based on the three-dimensional structure of Nef, three fragments of the Nef protein of HIV-1 strain LAI have been designed in order to determine the localization of the immunosuppressive domain of Nef.

1) a fragment extending from residue number 1 to residue number 89
2) a fragment extending from residue number 80 to residue number 120
3) a fragment extending from residue number 113 to residue number 206

Fragment 2 comprises the putative immunosuppressive domain, while fragments number 1 and 3 do not comprise this domain. Fragment 2 extents both ways from the putative immunosuppressive domain of Nef in order to include the whole two alpha-helical domains containing the putative immunosuppressive domain of Nef, according to the known core structure of the HIV-1 Nef protein (PBD entry IEFN).

The DNAs coding for those fragments were generated by PCR using the Nef gene cloned into the pCDNA3 vector (Peden K., Emerman M. and Montagnier L. 1991, *Virology* 185(2):661-672) as a template and the following primers pairs:

```
for fragment 1:
                                          (SEQ ID NO: 22)
atacatggcccagccggccggtggcaagtggtcaaaaagtagt (SEQ ID NO: 23)
atacatacgcgttcagtggctaagatctacagctgcctt for fragment 2:
                                          (SEQ ID NO: 24)
atacatggcccagccggccacttacaaggcagctgtagatcttagc (SEQ ID NO: 25)
atacatacgtcgttcagccttgtgtgtggtagatccac for fragment 3:
                                          (SEQ ID NO: 26)
atacatggcccagccggccgatatccttgatctgtggatctaccac (SEQ ID NO: 27)
atacataacgcgttcagcagttcttgaagtactccgg
```

The PCR products were digested with SfiI and MluI and cloned into pDFG-expNef opened with the same enzymes, resulting in the genetic fusion of the fragments with the extracellular exportation signal peptide of the human Igκ light chain. Thus, the obtained constructs expressed extracellularly localized fragments of HIV-1 Nef. They were used in an in vivo immunosuppression assay as described in Example 2. A positive index (+) indicates that the considered fragment has in vivo immunosuppressive properties, whereas an index inferior or equal to zero (−) indicates that the considered fragment is devoid of such properties.

Figure 5:
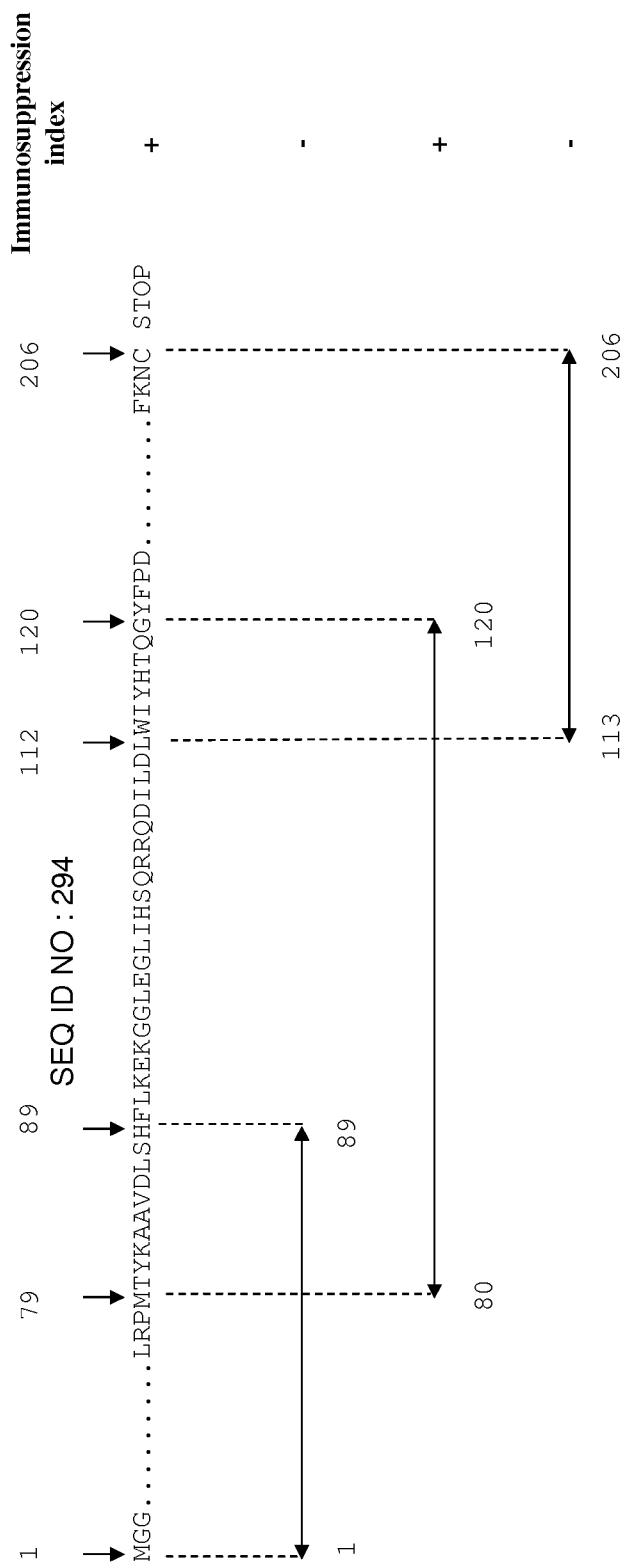

As illustrated in FIG. 5, the fragment extending from residue 90 to residue 120 of HIV-1 Nef protein displays an immunosuppressive property in vivo. This fragment thus comprises the immunosuppressive domain of Nef. Fragments 1 and 3 indicate that this immunosuppressive domain could be further reduced to amino acids 90 to 112.

Example 6

Determination of the Immunosuppression Index of Additional Wild Type Nef Proteins The immunosuppression index of Nef was determined as described in Example 2 for HIV-1 strain A1 Nef (SEQ ID NO: 28) and for HIV-2 strain ST Nef (SEQ ID NO: 29).

Figure 6A:
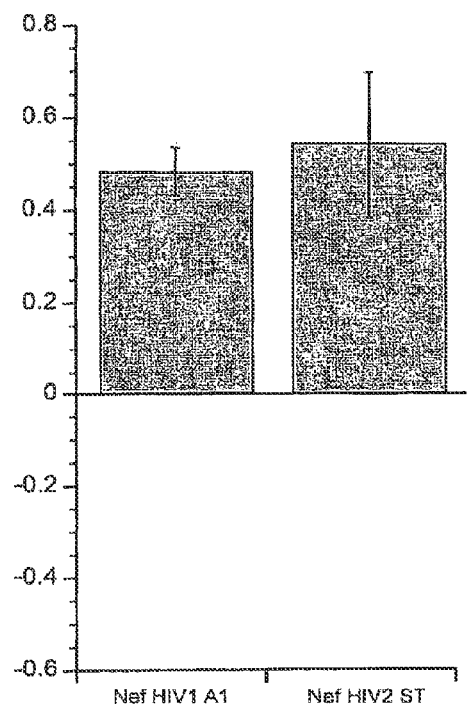
FIG. 6A represents the immunosuppression index (vertical axis) of HIV-1 strain A1 Nef (left column) and for HIV-2 strain ST Nef (right column).

As expected, the results indicate that these Nef proteins are also immunosuppressive (FIG. 6A).

Example 7

Determination of the Immunosuppression Index of a SIV Nef and of its E125R Mutant The immunosuppression index was determined for the SIV strain mac239 wild type Nef (SEQ ID NO: 30) and its E125R mutant (SEQ ID NO: 31) as described in Example 2. The E125R mutation in SIV mac239 Nef is homologous to the above defined E93R mutation of HIV-1 LAI and was introduced following a procedure similar to that described in Example 1.

Figure 6B:
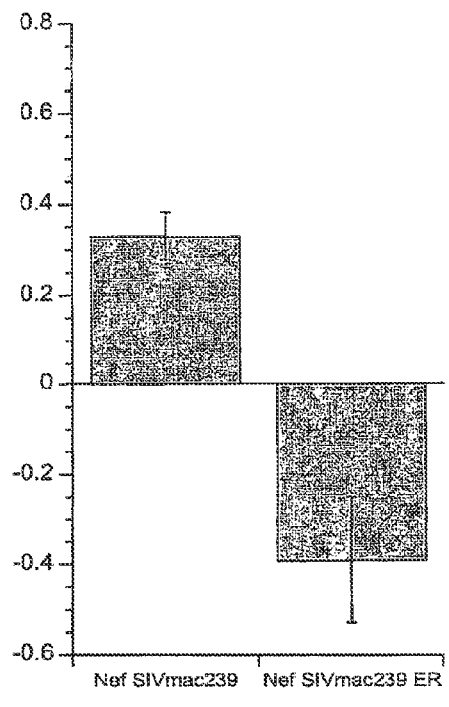
FIG. 6B represents the immunosuppression index (vertical axis) of SIV strain mac239 Nef (left column) and of the corresponding B125R mutant (right column).

The results indicate that the SIV Nef protein possesses an immunosuppressive activity while the E→R mutant is completely devoid of such an activity (FIG. 6B).

The invention claimed is:

1. A composition comprising a pharmaceutically acceptable carrier and a mutated Nef protein having substantially no immunosuppressive activity, said mutated Nef protein being obtained by substitution of one amino acid of the immunosuppressive domain of a wild type Nef protein having an immunosuppressive domain that differs from the immunosuppressive domain of a non-mutated wild type Nef protein by a substitution of one amino acid of the immunosuppressive domain of said wild type Nef protein, said wild type Nef protein being constituted by one of the amino acid sequences of the group consisting of SEQ ID NO: 1, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 285, SEQ ID NO: 286, SEQ ID NO: 287, SEQ ID NO: 288, SEQ ID NO: 289, or SEQ ID NO: 290, said mutated Nef protein having substantially preserved CD4 and/or MHC-I downregulation functions with respect to the non mutated Nef protein, wherein the one amino acid is selected from the group consisting of:

the amino acid at position 93 of one of SEQ ID NO: 1, SEQ ID NO: 275, SEQ ID NO: 277, SEQ ID NO: 278, SEQ ID NO: 279, the amino acid at position 94 of SEQ ID NO: 276, the amino acid at position 96 of SEQ ID NO: 281, the amino acid at position 103 of SEQ ID NO: 280, the amino acid at position 124 of SEQ ID NO: 287, and the amino acid at position 125 of one of SEQ ID NO: 285, SEQ ID NO: 286, SEQ ID NO: 288, SEQ ID NO: 289, and SEQ ID NO: 290;

the one amino acid is substituted by one of R, H and K; and said mutated NEF protein varies from said wild type NEF protein by said substitution of said one amino acid in said immunosuppressive domain.

2. The composition according to claim 1, wherein the one amino acid is substituted by R.

3. The composition according to claim 1, comprising as active substance a mutated Nef protein as set forth in SEQ ID NO: 2.

4. The composition according to claim 1, further comprising at least one HIV protein, or a fragment thereof, or one HIV lipopeptide, or a fragment thereof.

5. The composition according to claim 4, wherein said HIV protein is chosen among gp41, gp120, gp140, gp160, Env, Gag, Pol, Rev, RT, Vpu and Tat.

6. A protein comprising the sequence as set forth in SEQ ID NO: 2 or SEQ ID NO: 31.

7. A composition comprising a pharmaceutically acceptable carrier and a mutated Nef protein having substantially no immunosuppressive activity, said mutated Nef protein being obtained by substitution of one amino acid of the immunosuppressive domain of a wild type Nef protein, provided that the substitution substantially preserves CD4 and/or MHC-I downregulation functions with respect to said wild type Nef protein, said wild type Nef protein being constituted by one of the amino acid sequences of the group consisting of SEQ ID NO: 1, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 285, SEQ ID NO: 286, SEQ ID NO: 287, SEQ ID NO: 288, SEQ ID NO: 289, or SEQ ID NO: 290, wherein the one amino acid is selected from the group consisting of:

the amino acid at position 93 of one of SEQ ID NO: 1, SEQ ID NO: 275, SEQ ID NO: 277, SEQ ID NO: 278, SEQ ID NO: 279, the amino acid at position 94 of SEQ ID NO: 276, the amino acid at position 96 of SEQ ID NO: 281, the amino acid at position 103 of SEQ ID NO: 280, the amino acid at position 124 of SEQ ID NO: 287, and the amino acid at position 125 of one of SEQ ID NO: 285, SEQ ID NO: 286, SEQ ID NO: 288, SEQ ID NO: 289, and SEQ ID NO: 290;

the one amino acid is substituted by one of R, H and K; and said mutated NEF protein varies from said wild type NEF protein by said substitution of said one amino acid in said immunosuppressive domain.

* * * * *